(12) United States Patent
Wang et al.

(10) Patent No.: US 8,586,584 B2
(45) Date of Patent: *Nov. 19, 2013

(54) COMPOUNDS FOR THE TREATMENT OF HEPATITIS C

(75) Inventors: Tao Wang, Farmington, CT (US); Annapurna Pendri, South Glastonbury, CT (US); Zhongxing Zhang, Madison, CT (US); Weixu Zhai, Middletown, CT (US); Guo Li, Wallingford, CT (US); Samuel Gerritz, Guilford, CT (US); Paul Michael Scola, Glastonbury, CT (US); Li-Qiang Sun, Glastonbury, CT (US); Qian Zhao, Wallingford, CT (US); Eric Mull, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 157 days.

This patent is subject to a terminal disclaimer.

(21) Appl. No.: 12/904,264

(22) Filed: Oct. 14, 2010

(65) Prior Publication Data

US 2011/0086858 A1 Apr. 14, 2011

Related U.S. Application Data

(60) Provisional application No. 61/251,466, filed on Oct. 14, 2009.

(51) Int. Cl.
*A61K 31/53* (2006.01)
*C07D 251/72* (2006.01)
*C07D 487/00* (2006.01)

(52) U.S. Cl.
USPC ............ 514/245; 514/246; 540/472; 544/208

(58) Field of Classification Search
USPC ........... 514/245, 246; 540/474, 472; 544/205, 544/208
See application file for complete search history.

(56) References Cited

U.S. PATENT DOCUMENTS

| | | | |
|---|---|---|---|
| 4,816,064 A | 3/1989 | Konno et al. | |
| 7,163,943 B2 | 1/2007 | Timmer et al. | |
| 7,169,785 B2 | 1/2007 | Timmer et al. | |
| 2009/0286778 A1 | 11/2009 | Combs et al. | |
| 2012/0093766 A1* | 4/2012 | Wang et al. | 424/85.2 |

FOREIGN PATENT DOCUMENTS

| | | |
|---|---|---|
| KR | 2004/0033100 A | 4/2004 |
| WO | WO02/079187 A1 | 10/2002 |
| WO | WO 2004/026881 | 4/2004 |
| WO | WO 2004/089286 | 10/2004 |
| WO | WO 2008/057209 | 5/2008 |
| WO | WO 2009/091388 | 7/2009 |
| WO | WO 2009/132202 | 10/2009 |
| WO | WO2010/036896 A1 | 4/2010 |
| WO | WO 2010/118367 | 10/2010 |

OTHER PUBLICATIONS

U.S. Appl. No. 13/086,036, filed Apr. 13, 2011, Wang et al.
U.S. Appl. No. 13/086,704, filed Apr. 14, 2011, Wang et al.

* cited by examiner

*Primary Examiner* — Yong Chong
*Assistant Examiner* — Jason A Deck
(74) *Attorney, Agent, or Firm* — James Epperson

(57) ABSTRACT

The disclosure provides compounds of formula I, including pharmaceutically acceptable salts, as well as compositions and methods of using the compounds. The compounds have activity against hepatitis C virus (HCV) and may be useful in treating those infected with HCV.

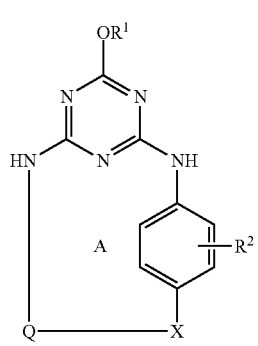

15 Claims, No Drawings

COMPOUNDS FOR THE TREATMENT OF HEPATITIS C

CROSS REFERENCE TO RELATED APPLICATIONS

This patent application claims the benefit of U.S. provisional patent application No. 61/251,466 filed Oct. 14, 2009.

BACKGROUND OF THE INVENTION

The disclosure generally relates to the novel compounds of formula I including pharmaceutically acceptable salts, which have activity against hepatitis C virus (HCV) and are useful in treating those infected with HCV. The disclosure also relates to compositions and methods of using these compounds.

Hepatitis C virus (HCV) chronically infects an estimated 170 million people worldwide, with 3 to 4 million infected individuals in the United States alone (Boyer, N. and Marcellin, P. *J. Hepatology.* 2000, 32:98-112; Alter, M. J., et al. *Engl. J. Med.* 1999, 341:556-562). Prior to the mid 1990s, transfusion with infected blood products was the main route of HCV transmission. Following the introduction of blood screening methods, transmission via injection drug use became the primary risk factor. Chronic infection often leads to the development of severe liver complications, including fibrosis, cirrhosis, and hepatocellular carcinoma. HCV infection is also the leading cause of orthotopic liver transplantation in the United States. The degree to which disease progression is related to viral and cellular factors is not completely understood.

Considerable heterogeneity is found within the nucleotide and encoded amino acid sequence of the HCV genome (Simmonds, P. *J. Gen. Virology.* 2004, 85:3173-3188). Based on this sequence diversity, six major genotypes and multiple associated subtypes have been described. The genotypes of HCV differ in their worldwide distribution, and the clinical significance of the genetic heterogeneity of HCV remains elusive despite numerous studies of the possible effect of genotypes on pathogenesis and therapy.

Medical treatment for HCV is limited by the lack of a vaccine or approved therapies that specifically target the virus. Currently, patients undergo treatment with a combination of parenterally administered pegylated alpha-interferon and oral ribavirin. Genotype 1 HCV is the most difficult to treat and elimination of the virus (sustained virologic response) is achieved for only approximately 50% of patients (Fried, M. W. et al. *N. Engl. J. Med.* 2002, 347:975-982; Zeumzem, S, *Nature Clinical Practice.* 2008, 5:610-622). This poor treatment response, combined with often severe side effects induced by therapy, highlight a need for improved antiviral drugs with better efficacy and safety profiles.

HCV is a member of the Flaviviridae family of viruses with a single-stranded positive-sense RNA genome. Following infection of host cells, the 9.6 Kb genome is translated into a polyprotein precursor of approximately 3,000 amino acids (reviewed in Lindenbach, B. D. and Rice, C. M. *Nature.* 2005, 436:933-938; Moradpour, D, Penin, F., and Rice, C. M. *Nature Reviews.* 2007, 5:453-463). Post-translational processing by both cellular and viral proteases results in the generation of at least 10 separate viral proteins. The structural proteins (which by definition are found in mature virions) include core, E1, E2, and possibly p7, and originate from the amino-terminal region of the polyprotein. The core protein assembles into the viral nucleocapsid. The E1 and E2 glycoproteins form heterodimers that are found within the lipid envelope surrounding the viral particles, and mediate host cell receptor binding and entry of the virus into cells. It is unclear if p7 is a structural protein, and its role in replication has yet to be defined. However p7 is believed to form an ion channel in cellular membranes, preventing acidification of intracellular compartments in which virions are assembled, and it has been shown to be essential for viral replication and assembly. The nonstructural proteins NS2, NS3, NS4A, NS4B, NS5A, and NS5B are produced through maturational cleavages of the carboxy-terminal region of the polyprotein. NS2 along with the amino terminus of NS3 form the NS2-3 metalloprotease which cleaves at the N52-NS3 junction. Additionally, NS2 is involved in assembly and egress of nascent virions. The NS3 protein contains both a serine protease in its amino-terminal region, and a nucleotide-dependent RNA helicase in its carboxy-terminal region. NS3 forms a heterodimer with the NS4A protein, constituting the active protease which mediates cleavages of the polyprotein downstream of NS3, both in cis, at the NS3-NS4A cleavage site, and in trans, for the remaining NS4A-NS4B, NS4B-NS5A, NS5A-NS5B sites. The complex formation of the NS3 protein with NS4A seems necessary to the processing events, enhancing the proteolytic efficiency at all of the sites. The NS3 protein also exhibits nucleoside triphosphatase and RNA helicase activities. The NS4B protein has been shown to be important for localization of HCV proteins into replication complexes in altered membranous structures within the cell. NS5B encodes an RNA-dependent RNA polymerase that is involved in the replication of HCV.

Subgenomic HCV replicons, containing the untranslated regions 5' and 3' to the coding sequence fused to the nonstructural proteins or the full-length polyprotein, are competent for translation, viral protein expression, and replication within cultured cells (Lohmann, V. et al. *Science.* 1999, 285:110-113; Moradpour, D, Penin, F., and Rice, C. M. *Nature Reviews.* 2007, 5:453-463). The replicon system has proven valuable for the identification of inhibitors targeting the nonstructural proteins associated with these functions. However, only limited subsets of HCV genotypes have been used to generate functional replicons.

Other systems have been used to study the biology of the HCV structural proteins that mediate the entry into host cells. For example, virus-like-particles made in recombinant baculovirus-infected cells with the HCV core, E1 and E2 proteins have also been used to study the function of the HCV E1 and E2 proteins (Barth, H., et al. *J. Biol. Chem.* 2003, 278:41003-41012). In addition, pseudotyping systems where the E1 and E2 glycoproteins are used to functionally replace the glycoproteins of retroviruses have been developed (Bartosch, B., Dubuisson, J. and Cosset, F.-L. *J. Exp. Med.* 2003, 197:633-642; Hsu, M. et al. *Proc. Natl. Acad. Sci. USA.* 2003, 100: 7271-7276). These systems yield HCV pseudoparticles that bind to and enter host cells in a manner which is believed to be analogous to the natural virus, thus making them a convenient tool to study the viral entry steps as well as to identify inhibitors block this process.

Recently, a full-length genotype 2a HCV clone, JFH1, was isolated and demonstrated the ability to replicate in vitro. Through repeated passage and adaptation in cell culture increased titers of infectious virus were produced (Lindenbach, B. D., et al. *Science.* 2005, 309:623-626; Wakita, T. et al. *Nature Med.* 2005, 11:791-796). In contrast to the HCV replicon or pseudotyping systems, the infectious virus is useful for studying the complete HCV replication cycle, including identifying inhibitors of not only the replication proteins, but those involved in early steps in virus infection (entry and uncoating) and production of progeny viruses (genome packaging, nucleocapsid assembly, virion envelopment and egress).

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I where
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
$R^2$ is cyano, hydrogen, halo, alkyl, haloalkyl, alkoxy, or haloalkoxy;
$R^3$ is hydrogen, alkyl, (amino)alkyl, (alkylamino)alkyl, (dialkylamino)alkyl((alkylcarbonyl)amino)alkyl, ((haloalkylcarbonyl)amino)alkyl, ((alkoxycarbonyl)amino)alkyl, ((benzyloxycarbonyl)amino)alkyl, alkylcarbonyl, alkoxycarbonyl, benzyloxycarbonyl, aminocarbonyl, alkylaminocarbonyl, or dialkyaminocarbonyl;
$R^4$ is hydrogen, alkyl, (amino)alkyl, (alkylamino)alkyl, or (dialkylamino)alkyl;
$R^5$ is hydrogen, alkyl, (amino)alkyl, (alkylamino)alkyl, or (dialkylamino)alkyl;
$R^6$ is pyrollidinyl, piperidinyl, or piperazinyl and is substituted with 0-3 substituents selected from alkyl, alkylcarbonyl, alkoxycarbonyl, and benzyloxycarbonyl;
Q is an alkylene or alkenylene chain containing 0-6 groups selected from the group consisting of O, $NR^3$, S, S(O), $S(O_2)$, C(O)O, C(O)$NR^4$, OC(O)$NR^4$, $NR^4$C(O)$NR^4$, and Z, provided that any O or S atom does not directly bond to another O or S atom, such that ring A is 13-24 membered; and where the alkylene or alkenylene chain is substituted with 0-6 substituents selected from the group consisting of alkyl, hydroxy, alkoxy, $R^6$, ($R^6$)alkyl, and phenyl where the phenyl substituent is further substituted with 0-4 cyano, halo, alkyl, haloalkyl, alkoxy, or haloalkoxy substituents;
X is O, $CH_2$, CO, $CO_2$, or C(O)$NR^5$; and
Z is $C_{3-7}$ cycloalkylene, phenylene, pyrrolidindiyl, piperidindiyl, or piperazindiyl;
or a pharmaceutically acceptable salt thereof.

Another aspect of the invention is a compound of formula I where:
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
$R^2$ is cyano, hydrogen, halo, alkyl, haloalkyl, alkoxy, or haloalkoxy;
$R^3$ is hydrogen, alkyl, alkylcarbonyl, alkoxycarbonyl, aminocarbonyl, alkylaminocarbonyl, or dialkyaminocarbonyl;
$R^4$ is hydrogen or alkyl;
$R^5$ is hydrogen, alkyl, (amino)alkyl, (alkylamino)alkyl, or (dialkylamino)alkyl;
Q is an alkylene or alkenylene chain containing 0-3 groups selected from the group consisting of O, $NR^3$, S, S(O), $S(O_2)$, C(O)O, C(O)$NR^4$, OC(O)$NR^4$, $NR^4$C(O)$NR^4$, and Z, provided that O, $NR^3$, S, S(O), $S(O_2)$, C(O)O, C(O)$NR^4$, OC(O)$NR^4$, and $NR^4$C(O)$NR^4$ do not directly bond to each other or to NH or X, such that ring A is 13-24 membered; and where the alkylene or alkenylene chain is substituted with 0-3 substituents selected from the group consisting of alkyl, hydroxy, alkoxy, and phenyl where the phenyl substituent is further substituted with 0-4 cyano, halo, alkyl, haloalkyl, alkoxy, or haloalkoxy substituents;
X is O, $CO_2$, or C(O)$NR^5$; and
Z is $C_{3-7}$ cycloalkylene or phenylene;
or a pharmaceutically acceptable salt thereof.

Another aspect of the invention is a compound of formula I where $R^1$ is haloalkyl; $R^2$ is hydrogen; $R^3$ is hydrogen or alkylcarbonyl; $R^5$ is hydrogen; Q is an alkylene or alkenylene chain containing 0-2 groups selected from the group consisting of O, $NR^3$, and Z, such that ring A is 16-23 membered; X is O or CONR$^5$; and Z is phenylene; or a pharmaceutically acceptable salt thereof.

Another aspect of the invention is a compound of formula I where $R^1$ is trifluoroethyl; $R^2$ is hydrogen; Q is (p-$C_6H_6$)OCH$_2$CH=CHCH$_2$, CH$_2$(p-$C_6H_6$)OCH$_2$CH$_2$CH$_2$, CH$_2$(p-$C_6H_6$)OCH$_2$CH$_2$CH$_2$CH$_2$, CH$_2$(p-$C_6H_6$)OCH$_2$CH$_2$CH$_2$CH$_2$CH$_2$, CH$_2$(p-$C_6H_6$)OCH$_2$CH=CHCH$_2$, CH$_2$CH$_2$CH$_2$CH$_2$CH$_2$CH$_2$CH$_2$CH$_2$, CH$_2$CH$_2$CH$_2$CH$_2$CH$_2$CH$_2$CH$_2$CH$_2$CH$_2$CH$_2$, CH$_2$CH$_2$CH$_2$OCH$_2$CH$_2$CH$_2$CH$_2$OCH$_2$CH$_2$CH$_2$, CH$_2$CH$_2$NHCH$_2$CH$_2$, CH$_2$CH$_2$N(Ac)CH$_2$CH$_2$, or

*—⟨⟩—CONHCH$_2$CH$_2$CH$_2$CH$_2$—;

and X is O or CONH; or a pharmaceutically acceptable salt thereof.

Another aspect of the invention is a compound of formula I where $R^1$ is trifluoroethyl.

Another aspect of the invention is a compound of formula I where Q is (p-$C_6H_6$)OCH$_2$CH=CHCH$_2$, CH$_2$(p-$C_6H_6$)OCH$_2$CH$_2$CH$_2$, CH$_2$(p-$C_6H_6$)OCH$_2$CH$_2$CH$_2$CH$_2$, CH$_2$(p-$C_6H_6$)OCH$_2$CH$_2$CH$_2$CH$_2$CH$_2$, CH$_2$(p-$C_6H_6$)OCH$_2$CH=CHCH$_2$, CH$_2$CH$_2$CH$_2$CH$_2$CH$_2$CH$_2$CH$_2$CH$_2$, CH$_2$CH$_2$CH$_2$CH$_2$CH$_2$CH$_2$CH$_2$CH$_2$CH$_2$CH$_2$, CH$_2$CH$_2$CH$_2$OCH$_2$CH$_2$CH$_2$CH$_2$OCH$_2$CH$_2$CH$_2$, CH$_2$CH$_2$NHCH$_2$CH$_2$, CH$_2$CH$_2$N(Ac)CH$_2$CH$_2$, or

*—⟨⟩—CONHCH$_2$CH$_2$CH$_2$CH$_2$—.

Another aspect of the invention is a compound of formula I where X is CONH.

Another aspect of the invention is a compound of formula I where X is O.

Another aspect of the invention is a compound of formula I where Z is phenylene.

Another aspect of the invention is a compound of formula I where Z is cyclopropanediyl or cyclohexanediyl.

Another aspect of the invention is a compound of formula I where Z is pyrrolidindiyl or piperazindiyl.

Any scope of any variable, including $R^1$, $R^2$, $R^3$, $R^4$, $R^5$, Q, X and Z, can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Alkylene" means a straight or branched divalent alkyl group composed of 1 to 6 carbons. "Alkenylene" means a straight or branched divalent alkyl group composed of 2 to 6 carbons with at least one double bond. "Cycloalkylene" means a divalent cycloalkane moiety composed of 3 to 7 carbons and includes gem-divalency (for example 1,1-cyclopropanediyl) as well as non-gem-divalency (for example, 1,4-cyclohexanediyl). Phenylene is a divalent benzene ring. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The substituents described above may be attached at any suitable point of attachment unless otherwise specified. However, it is understood that the compounds encompassed by the present invention are those that are chemically stable as understood by those skilled in the art. Additionally, the compounds encompassed by the present disclosure are those that are suitably stable for use as a pharmaceutical agent.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Infection assays. HCV pseudoparticles, produced using standardized methodology (Bartosch, B., Dubuisson, J. and Cosset, F.-L. *J. Exp. Med.* 2003, 197:633-642) were made via a liposome-based transfection procedure of 293T cells with plasmids expressing the murine leukemia virus capsid and polymerase proteins, an MLV genome encoding the luciferase reporter gene, and envelope glycoproteins from either HCV or vesicular stomatitis virus (VSV). The genotype 1a HCV E1 and E2 envelope coding sequences were derived from the H77C isolate (GenBank accession number AF009606). Media containing pseudoparticles was collected 3 days following transfection, filtered, and stored at −20° C. as a viral stock. Infections were performed in 384-well plates by mixing pseudovirus with $1 \times 10^4$ Huh7 cells/well in the presence or absence of test inhibitors, followed by incubation at 37° C. Luciferase activity, reflecting the degree of entry of the pseudoparticles into host cells, was measured 2 days after infection. The specificity of the compounds for inhibiting HCV was determined by evaluating inhibition of VSV pseudoparticle infection.

Compounds and data analysis. Test compounds were serially diluted 3-fold in dimethyl sulfoxide (DMSO) to give a final concentration range in the assay of 50.0 µM to 0.04 µM. Maximum activity (100% of control) and background were derived from control wells containing DMSO but no inhibitor or from uninfected wells, respectively. The individual signals in each of the compound test wells were then divided by the averaged control values after background subtraction and multiplied by 100% to determine percent activity. Assays were performed in duplicate and average $EC_{50}$ values (reflecting the concentration at which 50% inhibition of virus replication was achieved) were calculated. Compound $EC_{50}$ data is expressed as A: =0.5-100 nM; B=100-1000 nM; C=1000-5000 nM). Representative data for compounds are reported in Table 1.

TABLE 1

| Example | EC$_{50}$ (nM) 1a (H77C) | EC$_{50}$ (nM) 1a (H77C) |
|---|---|---|
| 0001 | C | 4201 |
| 0002 | A | |
| 0003 | B | 100.6 |
| 0004 | A | 48.36 |
| 0005 | C | |
| 0006 | C | |
| 0007 | A | 8.31 |
| 0008 | A | |
| 0009 | B | |
| 0010 | C | |
| 0011 | A | 62.78 |
| 0021 | B | |
| 0022 | B | |
| 0023 | B | |
| 0024 | C | 16290.00 |
| 0031 | B | |
| 0032 | B | |
| 0033 | B | |
| 0034 | C | |
| 0035 | C | |
| 0036 | C | |
| 0037 | B | |
| 0038 | B | 840.30 |
| 0039 | B | |
| 0041 | C | 21610.00 |
| 0042 | B | |
| 0051 | B | |
| 0052 | B | |
| 0053 | B | |
| 0054 | C | 5209.00 |
| 0055 | B | |
| 0056 | B | |
| 0057 | B | |
| 0058 | B | |
| 0059 | A | |
| 0060 | B | |
| 0061 | B | |
| 0062 | B | |
| 0063 | B | |
| 0064 | B | 407.40 |
| 0065 | B | |
| 0067 | B | |
| 0068 | B | |
| 0069 | A | 78.81 |
| 0070 | A | |
| 0071 | B | |
| 0072 | A | |
| 2001 | A | 2.30 |
| 2002 | A | |
| 2003 | A | |
| 2004 | A | |
| 2005 | A | |
| 2006 | A | |
| 2007 | A | |
| 2008 | A | |
| 2009 | B | 159.30 |
| 2010 | A | |
| 2011 | A | |
| 2012 | A | |
| 2013 | A | |
| 2014 | A | |
| 2015 | A | |
| 2016 | A | |
| 2017 | B | |
| 2018 | A | 33.60 |
| 2019 | A | |
| 2020 | A | |
| 2021 | B | 417.00 |
| 2022 | A | |
| 2023 | A | |
| 3001 | A | |
| 3002 | B | |
| 3003 | B | |
| 3004 | C | 2937.00 |
| 3005 | C | |
| 3006 | C | |
| 3007 | B | 556.80 |
| 3008 | B | |
| 3009 | B | |
| 3010 | A | 20.32 |
| 3012 | B | 275.20 |

Pharmaceutical Compositions and Methods of Treatment

The compounds demonstrate activity against HCV and can be useful in treating HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
| --- | --- | --- |
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |

TABLE 2-continued

| Brand Name | Type of Inhibitor or Target | Source Company |
|---|---|---|
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

For the section of compounds in the 0000 series all Liquid Chromatography (LC) data were recorded on a Shimadzu LC-10AS or LC-20AS liquid chromatograph using a SPD-10AV or SPD-20A UV-Vis detector and Mass Spectrometry (MS) data were determined with a Micromass Platform for LC in electrospray mode.

HPLC Method (i.e., compound isolation). Compounds purified by preparative HPLC were diluted in methanol (1.2 mL) and purified using a Shimadzu LC-8A or LC-10A automated preparative HPLC system.

Synthesis of intermediate methyl 4-(4-chloro-6-(2,2,2-trifluoroethoxy)-1,3,5-triazin-2-ylamino)benzoate

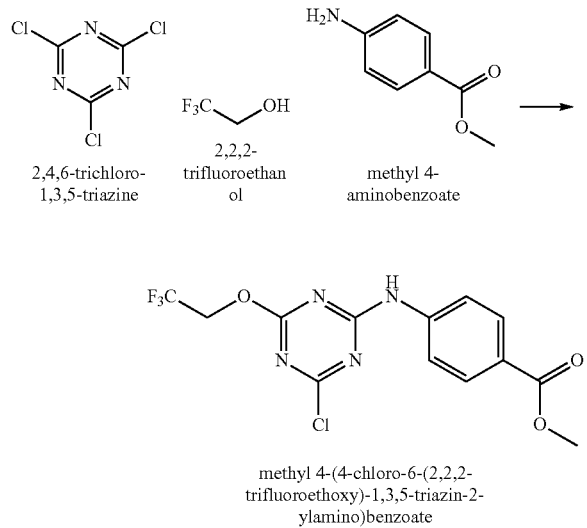 [SMILES: Clc1nc(Cl)nc(Cl)n1 ; OCC(F)(F)F ; COC(=O)c1ccc(N)cc1 ; COC(=O)c1ccc(Nc2nc(Cl)nc(OCC(F)(F)F)n2)cc1]

2,4,6-trichloro-1,3,5-triazine 2,2,2-trifluoroethanol methyl 4-aminobenzoate methyl 4-(4-chloro-6-(2,2,2-trifluoroethoxy)-1,3,5-triazin-2-ylamino)benzoate Step 1: To a soln. of 2,4,6-trichloro-1,3,5-triazine (10 g) in THF (200 mL) was added a mixture of 2,2,2-trifluoroethanol (5.42 g) and iPr$_2$NEt (20 mL) at room temperature. The resulting mixture was stirred at room temperature for 16 hours.

Step 2: Methyl 4-aminobenzoate (8.2 g) was added into the above solution and the reaction was carried out room temperature for 16 hours before adding water (200 mL). The aqueous layer was extracted with EtOAc (3×200 mL). The combined organic phase was dried over MgSO$_4$ and concentrated to give the crude product which was used in the further reactions without purification.

| Methyl 4-(4-chloro-6-(2,2,2-trifluoroethoxy)-1,3,5-triazin-2-ylamino)benzoate | |
|---|---|
| MS (M − H)$^+$ Calcd. | 361.0 |
| MS (M − H)$^+$ Observ. | 361.0 |
| Retention Time | 2.17 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 3 min |
| Flow Rate | 5 mL/min |
| Wavelength | 220 |
| Solvent Pair | ACN:Water:Ammonium Actetate |
| Column | Phenomenex Luna 4.6 × 50 mm S10 |

Synthesis of Compound 0001:

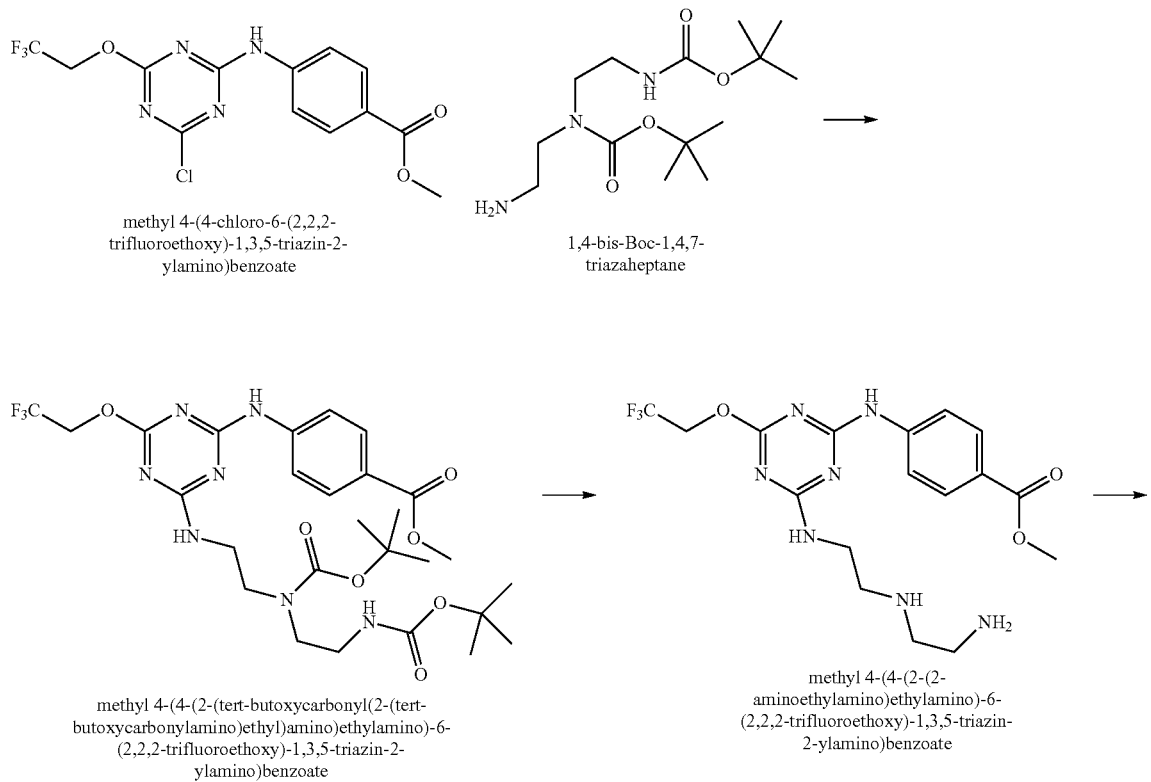

methyl 4-(4-chloro-6-(2,2,2-trifluoroethoxy)-1,3,5-triazin-2-ylamino)benzoate 1,4-bis-Boc-1,4,7-triazaheptane methyl 4-(4-(2-(tert-butoxycarbonyl(2-(tert-butoxycarbonylamino)ethyl)amino)ethylamino)-6-(2,2,2-trifluoroethoxy)-1,3,5-triazin-2-ylamino)benzoate methyl 4-(4-(2-(2-aminoethylamino)ethylamino)-6-(2,2,2-trifluoroethoxy)-1,3,5-triazin-2-ylamino)benzoate

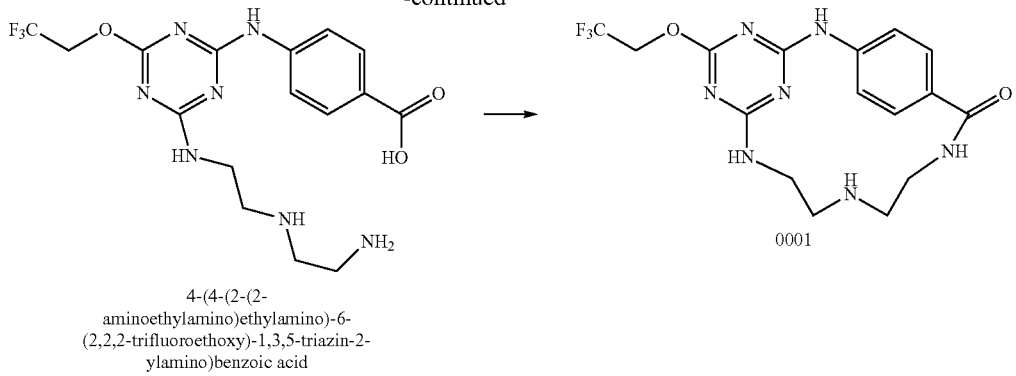

4-(4-(2-(2-aminoethylamino)ethylamino)-6-(2,2,2-trifluoroethoxy)-1,3,5-triazin-2-ylamino)benzoic acid Step 1: To a suspension of methyl 4-(4-chloro-6-(2,2,2-trifluoroethoxy)-1,3,5-triazin-2-ylamino)benzoate (600 mg) in THF (8 mL) was added 1,4-1,4-bis-Boc-1,4,7-triazaheptane (502 mg) and iPr$_2$NEt (0.578 mL). The mixture was heated at 70° C. for 16 hours. The solvent was removed under vacuum. The residue was purified via silica gel column (EtOAC/Hexanes=4:1) to give methyl 4-(4-(2-(tert-butoxycarbonyl(2-(tert-butoxycarbonylamino)ethyl)amino)ethylamino)-6-(2,2,2-trifluoroethoxy)-1,3,5-triazin-2-ylamino)benzoate (0.69 g).

| Methyl 4-(4-(2-(tert-butoxycarbonyl(2-(tert-butoxycarbonyl-amino)ethyl)amino)ethylamino)-6-(2,2,2-trifluoroethoxy)-1,3,5-triazin-2-ylamino)benzoate | |
|---|---|
| MS (M + H)$^+$ Calcd. | 630.3 |
| MS (M + H)$^+$ Observ. | 630.2 |
| Retention Time | 1.99 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: To a solution of methyl 4-(4-(2-(tert-butoxycarbonyl(2-(tert-butoxycarbonylamino)ethyl)amino)ethylamino)-6-(2,2,2-trifluoroethoxy)-1,3,5-triazin-2-ylamino)benzoate (200 mg) in dichloromethane (6 mL) was added TFA (0.734 mL). The mixture was stirred at r.t. for 4 hours. All solvents were removed under vacuum to afford the crude product which was used for next step without further purification.

| Methyl 4-(4-(2-(2-aminoethylamino)ethylamino)-6-(2,2,2-trifluoroethoxy)-1,3,5-triazin-2-ylamino)benzoate | |
|---|---|
| MS (M + H)$^+$ Calcd. | 430.2 |
| MS (M + H)$^+$ Observ. | 430.1 |
| Retention Time | 1.37 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: To a suspension of methyl 4-(4-(2-(2-aminoethylamino)ethylamino)-6-(2,2,2-trifluoroethoxy)-1,3,5-triazin-2-ylamino)benzoate (0.1 g) in acetone (6 mL) was added potassium carbonate (0.080 g) in water (6.00 mL). The mixture was heated to reflux for 16 hours. After cooling to room temperature, the reaction solution was acidified with 1N HCl to pH=3. All solvents were removed under vacuum. The residue was purified by prep. HPLC to give 4-(4-(2-(2-aminoethylamino)ethylamino)-6-(2,2,2-trifluoroethoxy)-1,3,5-triazin-2-ylamino)benzoic acid (40 mg).

| 4-(4-(2-(2-Aminoethylamino)ethylamino)-6-(2,2,2-trifluoroethoxy)-1,3,5-triazin-2-ylamino)benzoic acid | |
|---|---|
| MS (M + H)$^+$ Calcd. | 416.2 |
| MS (M + H)$^+$ Observ. | 416.1 |
| Retention Time | 1.17 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 4: To a solution of 4-(4-(2-(2-aminoethylamino)ethylamino)-6-(2,2,2-trifluoroethoxy)-1,3,5-triazin-2-ylamino)benzoic acid (20 mg) in DMF (8 mL) was added 2-(1H-benzotriazol-1-yl)-1,1,3,3-tetramethyluronium tetrafluoroborate (TBTU) (17.01 mg) and iPr₂NEt (0.067 mL). The mixture was stirred at room temperature for 16 hours before all solvents were removed under vacuum. The residue was purified by prep. HPLC to give compound 0001.

| Compound 0001 | |
|---|---|
| MS (M + H)⁺ Calcd. | 398.2 |
| MS (M + H)⁺ Observ. | 398.1 |
| Retention Time | 1.20 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |
| NMR | |
| ¹H (500 MHz, DMSO-D6) δ ppm | 2.45 (m, 2H), 2.64 (m, 2H), 2.92 (m, 2H), 3.06 (m, 2H), 4.91 (q, J = 10.0 Hz, 2H), 7.27 (d, J = 5.0 Hz, 2H), 7.42 (d, J = 5.0 Hz, 2H), 7.66 (t, J = 5.0 Hz, 1H), 7.86 (t, J = 5.0 Hz, 1H), 8.41 (b, 1H), 9.68 (s, 1H) |

Synthesis of Compound 0002:

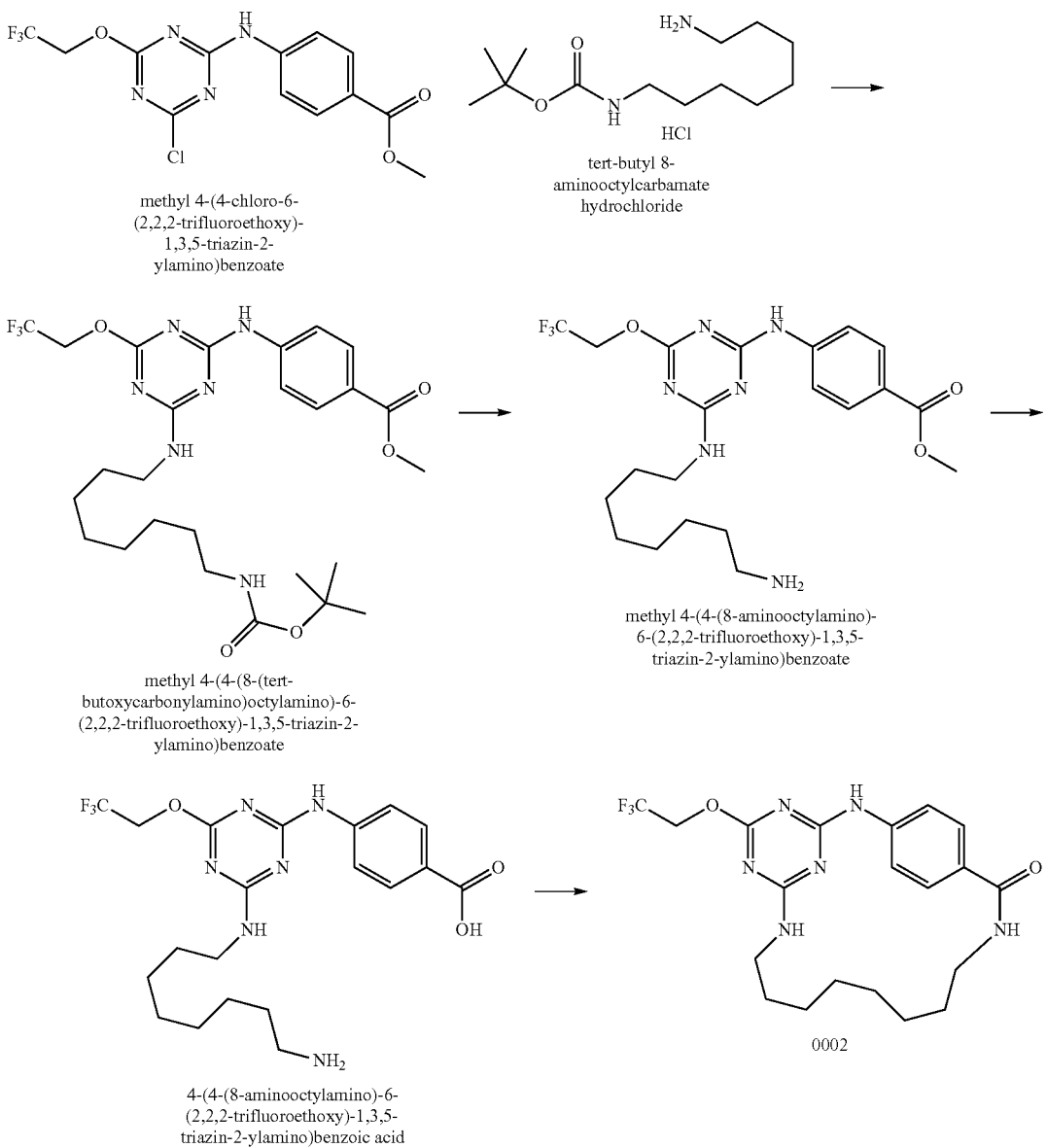

Step 1: To a suspension of methyl 4-(4-chloro-6-(2,2,2-trifluoroethoxy)-1,3,5-triazin-2-ylamino)benzoate (600 mg) in THF (20 mL) was added tert-butyl 8-aminooctylcarbamate hydrochloride (465 mg) and iPr$_2$NEt (0.578 mL). The mixture was heated at 70° C. for 16 hours. The solvent was removed under vacuum. The residue was purified by silica gel column (EtOAC/Hexanes=4:1) to give methyl 4-(4-(8-(tert-butoxycarbonylamino)octylamino)-6-(2,2,2-trifluoroethoxy)-1,3,5-triazin-2-ylamino)benzoate (0.57 g).

| Methyl 4-(4-(8-(tert-butoxycarbonylamino)octylamino)-6-(2,2,2-trifluoroethoxy)-1,3,5-triazin-2-ylamino)benzoate | |
|---|---|
| MS (M + H)$^+$ Calcd. | 571.3 |
| MS (M + H)$^+$ Observ. | 571.2 |
| Retention Time | 2.14 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: To a solution of methyl 4-(4-(8-(tert-butoxycarbonylamino)octylamino)-6-(2,2,2-trifluoroethoxy)-1,3,5-triazin-2-ylamino)benzoate (200 mg) in dichloromethane (6 mL) was added TFA (0.405 mL). The mixture was stirred at r.t. for 4 hours. All solvents were removed under vacuum. The crude product was used for next step without further purification.

| Methyl 4-(4-(8-aminooctylamino)-6-(2,2,2-trifluoroethoxy)-1,3,5-triazin-2-ylamino)benzoate | |
|---|---|
| MS (M + H)$^+$ Calcd. | 471.2 |
| MS (M + H)$^+$ Observ. | 471.2 |
| Retention Time | 1.59 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: To a suspension of methyl 4-(4-(8-aminooctylamino)-6-(2,2,2-trifluoroethoxy)-1,3,5-triazin-2-ylamino)benzoate (0.1 g) in acetone (6 mL) was added potassium carbonate (0.073 g) in water (6.00 mL). The mixture was heated to reflux overnight. After cooling to r.t., the reaction solution was acidified with 1N HCl to pH=3. All solvents were removed under vacuum. The residue was purified by prep. HPLC to give 4-(4-(8-aminooctylamino)-6-(2,2,2-trifluoroethoxy)-1,3,5-triazin-2-ylamino)benzoic acid (38 mg).

| 4-(4-(8-Aminooctylamino)-6-(2,2,2-trifluoroethoxy)-1,3,5-triazin-2-ylamino)benzoic acid | |
|---|---|
| MS (M + H)$^+$ Calcd. | 457.2 |
| MS (M + H)$^+$ Observ. | 457.2 |
| Retention Time | 1.32 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 4: To a solution of 4-(4-(8-aminooctylamino)-6-(2,2,2-trifluoroethoxy)-1,3,5-triazin-2-ylamino)benzoic acid (20 mg) in DMF (8 mL) was added TBTU (15.48 mg) and iPr$_2$NEt (0.061 mL). The mixture was stirred at r.t. for 16 hours. All solvents were removed under vacuum. The residue was purified via prep. HPLC to give compound 0002.

| Compound 0002 | |
|---|---|
| MS (M + H)$^+$ Calcd. | 439.2 |
| MS (M + H)$^+$ Observ. | 439.1 |
| Retention Time | 1.64 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Synthesis of Compound 0003:

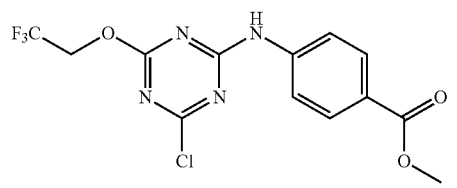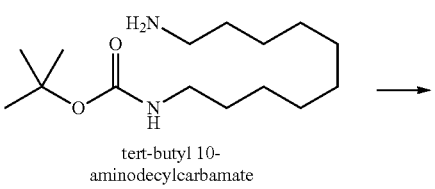

methyl 4-(4-chloro-6-(2,2,2-trifluoroethoxy)-1,3,5-triazin-2-ylamino)benzoate tert-butyl 10-aminodecylcarbamate

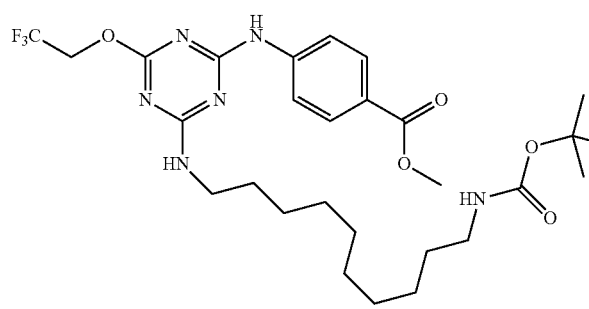

methyl 4-(4-(10-(tert-butoxycarbonylamino)decylamino)-6-(2,2,2-trifluoroethoxy)-1,3,5-triazin-2-ylamino)benzoate

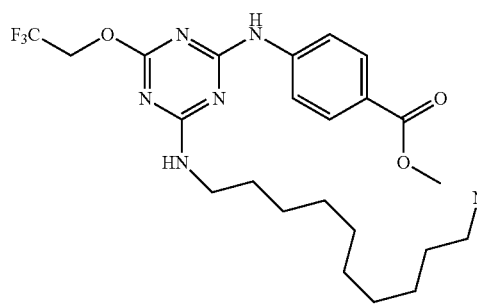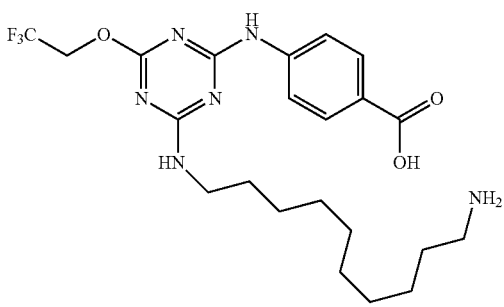

methyl 4-(4-(10-aminodecylamino)-6-(2,2,2-trifluoroethoxy)-1,3,5-triazin-2-ylamino)benzoate 4-(4-(10-aminodecylamino)-6-(2,2,2-trifluoroethoxy)-1,3,5-triazin-2-ylamino)benzoic acid

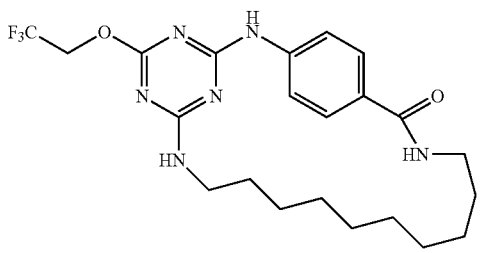

0003

Step 1: To a suspension of methyl 4-(4-chloro-6-(2,2,2-trifluoroethoxy)-1,3,5-triazin-2-ylamino)benzoate (600 mg) in THF (20 mL) was added tert-butyl 10-aminodecylcarbamate (451 mg) and iPr$_2$NEt (0.578 mL). The mixture was heated at 70° C. for 16 hours. The solvent was removed under vacuum. The residue was purified by silica gel column (EtOAC/Hexanes=4:1) to give methyl 4-(4-(10-(tert-butoxycarbonylamino)decylamino)-6-(2,2,2-trifluoroethoxy)-1,3,5-triazin-2-ylamino)benzoate (0.67 g).

| Methyl 4-(4-(10-(tert-butoxycarbonylamino)decylamino)-6-(2,2,2-trifluoroethoxy)-1,3,5-triazin-2-ylamino)benzoate | |
|---|---|
| MS (M + H)$^+$ Calcd. | 599.3 |
| MS (M + H)$^+$ Observ. | 599.3 |
| Retention Time | 2.26 min |
| LC Condition | |
| Solvent A | 5% ACN:95% Water:10 mm Ammonium Actetate |

| Methyl 4-(4-(10-(tert-butoxycarbonylamino)decylamino)-6-(2,2,2-trifluoroethoxy)-1,3,5-triazin-2-ylamino)benzoate | |
|---|---|
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: To a solution of methyl 4-(4-(10-(tert-butoxycarbonylamino)decylamino)-6-(2,2,2-trifluoroethoxy)-1,3,5-triazin-2-ylamino)benzoate (200 mg) in dichloromethane (6 mL) was added TFA (0.386 mL). The mixture was stirred at r.t. for 4 hours before all solvents were removed under vacuum. The crude product was used for next step without further purification.

| Methyl 4-(4-(10-aminodecylamino)-6-(2,2,2-trifluoroethoxy)-1,3,5-triazin-2-ylamino)benzoate | |
|---|---|
| MS (M + H)$^+$ Calcd. | 499.3 |
| MS (M + H)$^+$ Observ. | 499.2 |
| Retention Time | 1.70 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: To a suspension of methyl 4-(4-(10-aminodecylamino)-6-(2,2,2-trifluoroethoxy)-1,3,5-triazin-2-ylamino)benzoate (0.1 g) in acetone (6 mL) was added potassium carbonate in water (6.00 mL). The mixture was heated to reflux overnight. After cooling to r.t., the reaction solution was acidified with 1N HCl to pH=3. All solvens were removed under vacuum. The residue was purified by prep. HPLC to give 4-(4-(10-aminodecylamino)-6-(2,2,2-trifluoroethoxy)-1,3,5-triazin-2-ylamino)benzoic acid (25 mg).

| 4-(4-(10-Aminodecylamino)-6-(2,2,2-trifluoroethoxy)-1,3,5-triazin-2-ylamino)benzoic acid | |
|---|---|
| MS (M + H)$^+$ Calcd. | 485.3 |
| MS (M + H)$^+$ Observ. | 485.1 |
| Retention Time | 1.39 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 4: To a solution of 4-(4-(10-aminodecylamino)-6-(2,2,2-trifluoroethoxy)-1,3,5-triazin-2-ylamino)benzoic acid (15 mg) in DMF (8 mL) was added TBTU (10.93 mg) and iPr2NEt (0.043 mL). The mixture was stirred at r.t. for 16 hours before all the solvents were removed under vacuum. The residue was purified via prep. HPLC to give compound 0003.

| Compound 0003 | |
|---|---|
| MS (M + H)$^+$ Calcd. | 467.2 |
| MS (M + H)$^+$ Observ. | 467.2 |
| Retention Time | 1.82 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |
| NMR | |
| $^1$H (500 MHz, DMSO-D6) δ ppm | 1.18-1.26 (m, 10H), 1.37 (m, 2H), 1.51 (m, 4H), 3.16 (m, 2H), 3.25 (m, 2H), 4.93 (q, J = 10.0 Hz, 2H), 7.69 (d, J = 5.0 Hz, 2H), 7.76 (d, J = 5.0 Hz, 2H), 7.92 (t, J = 5.0 Hz, 1H), 8.30 (t, J = 5.0 Hz, 1H), 9.88 (s, 1H) |

Synthesis of Compound 0004:

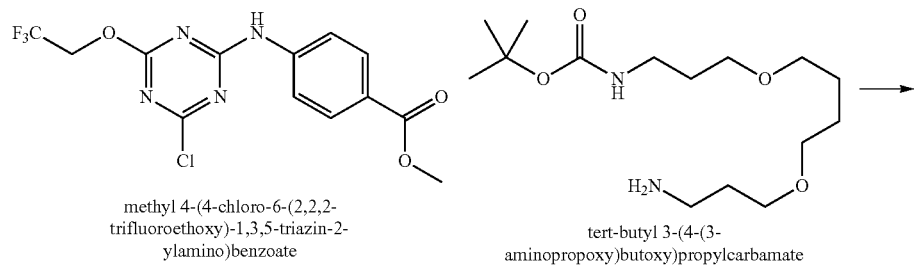

methyl 4-(4-chloro-6-(2,2,2-trifluoroethoxy)-1,3,5-triazin-2-ylamino)benzoate tert-butyl 3-(4-(3-aminopropoxy)butoxy)propylcarbamate

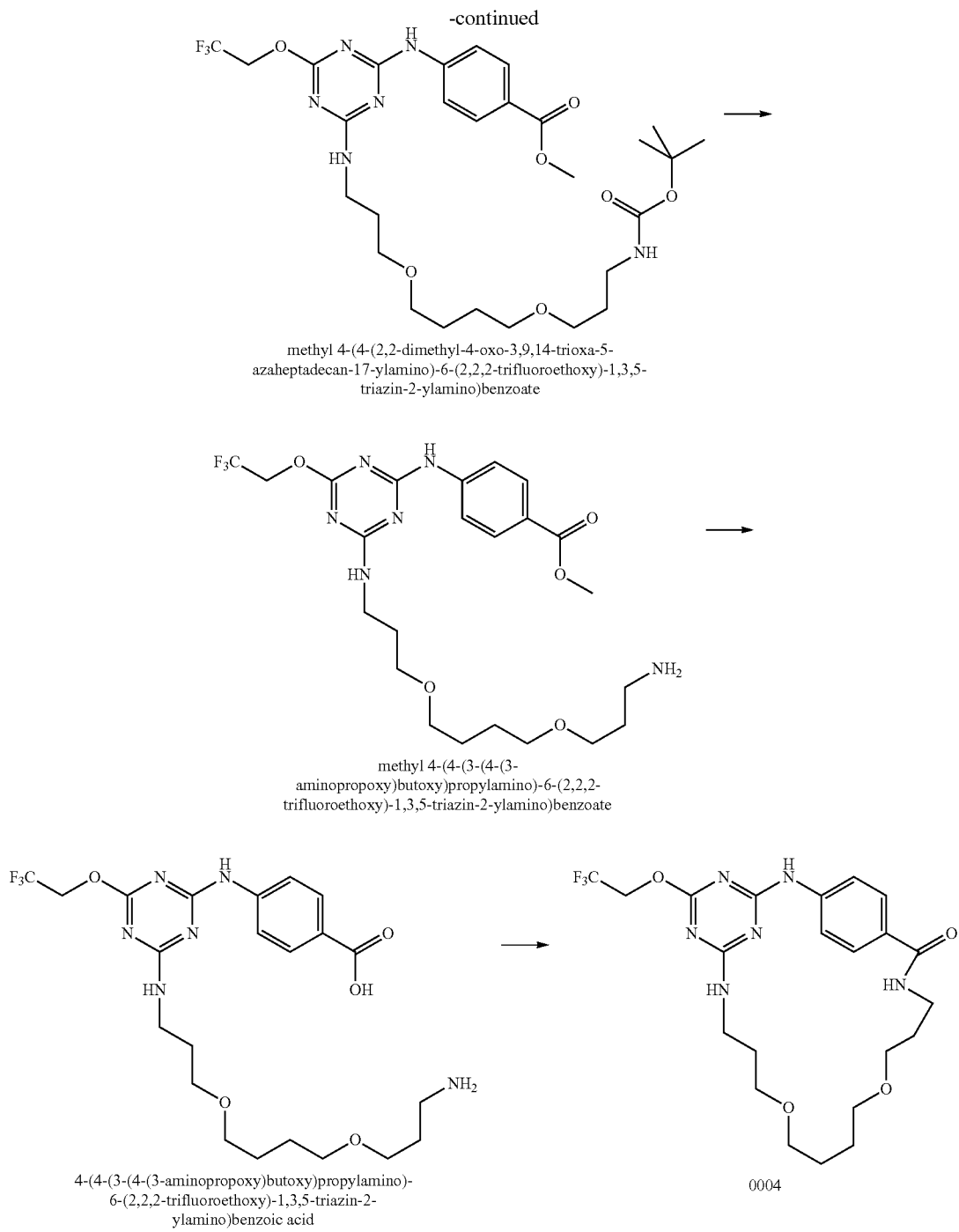

methyl 4-(4-(2,2-dimethyl-4-oxo-3,9,14-trioxa-5-azaheptadecan-17-ylamino)-6-(2,2,2-trifluoroethoxy)-1,3,5-triazin-2-ylamino)benzoate methyl 4-(4-(3-(4-(3-aminopropoxy)butoxy)propylamino)-6-(2,2,2-trifluoroethoxy)-1,3,5-triazin-2-ylamino)benzoate 4-(4-(3-(4-(3-aminopropoxy)butoxy)propylamino)-6-(2,2,2-trifluoroethoxy)-1,3,5-triazin-2-ylamino)benzoic acid

0004

Step 1: To a suspension of methyl 4-(4-chloro-6-(2,2,2-trifluoroethoxy)-1,3,5-triazin-2-ylamino)benzoate (600 mg) in THF (20 mL) was added tert-butyl 34443-aminopropoxy)butoxy)propylcarbamate (504 mg) and iPr$_2$NEt (0.578 mL). The mixture was heated at 70° C. for 16 hours. The solvent was removed under vacuum. The residue was purified by silica gel column (EtOAC/Hexanes=4:1) to give methyl 4-(4-(2,2-dimethyl-4-oxo-3,9,14-trioxa-5-azaheptadecan-17-ylamino)-6-(2,2,2-trifluoroethoxy)-1,3,5-triazin-2-ylamino)benzoate (601 mg).

| Methyl 4-(4-(2,2-dimethyl-4-oxo-3,9,14-trioxa-5-azaheptadecan-17-ylamino)-6-(2,2,2-trifluoroethoxy)-1,3,5-triazin-2-ylamino)benzoate | |
|---|---|
| MS (M + H)$^+$ Calcd. | 631.3 |
| MS (M + H)$^+$ Observ. | 631.2 |
| Retention Time | 3.61 min |
| LC Condition | |
| Solvent A | 90% Water -10% Methanol-0.1% TFA |
| Solvent B | 10% Water -90% Methanol-0.1% TFA |

| Methyl 4-(4-(2,2-dimethyl-4-oxo-3,9,14-trioxa-5-azaheptadecan-17-ylamino)-6-(2,2,2-trifluoroethoxy)-1,3,5-triazin-2-ylamino)benzoate | |
|---|---|
| Start % B | 0 |
| Final % B | 100 |
| Gradient Time | 4 min |
| Flow Rate | 5 mL/min |
| Wavelength | 220 |
| Solvent Pair | Water - Methanol- TFA |
| Column | PHENOMENEX-LUNA 3.0 × 50 mm S10 |

Step 2: To a solution of methyl 4-(4-(2,2-dimethyl-4-oxo-3,9,14-trioxa-5-azaheptadecan-17-ylamino)-6-(2,2,2-trifluoroethoxy)-1,3,5-triazin-2-ylamino)benzoate (200 mg) in dichloromethane (6 mL) was added TFA (0.366 mL). The mixture was stirred at r.t. for 4 hours before all solvents were removed under vacuum. The crude product was used for next step without further purification.

| Methyl 4-(4-(3-(4-(3-aminopropoxy)butoxy)propylamino)-6-(2,2,2-trifluoroethoxy)-1,3,5-triazin-2-ylamino)benzoate | |
|---|---|
| MS (M + H)+ Calcd. | 531.3 |
| MS (M + H)+ Observ. | 531.2 |
| Retention Time | 1.55 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: To a suspension of methyl 4-(4-(3-(4-(3-aminopropoxy)butoxy)propylamino)-6-(2,2,2-trifluoroethoxy)-1,3,5-triazin-2-ylamino)benzoate (0.1 g) in acetone (6 mL) was added potassium carbonate in water (6.00 mL). The mixture was heated to reflux for 16 hours. After cooling to r.t., the reaction solution was acidified with 1N HCl to pH=3. All the solvents were removed under vacuum. The residue was purified by prep. HPLC to give 4-(4-(3-(4-(3-aminopropoxy)butoxy)propylamino)-6-(2,2,2-trifluoroethoxy)-1,3,5-triazin-2-ylamino)benzoic acid (28 mg, 0.054 mmol).

| 4-(4-(3-(4-(3-Aminopropoxy)butoxy)propylamino)-6-(2,2,2-trifluoroethoxy)-1,3,5-triazin-2-ylamino)benzoic acid | |
|---|---|
| MS (M + H)+ Calcd. | 517.2 |
| MS (M + H)+ Observ. | 517.2 |
| Retention Time | 1.23 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |

| 4-(4-(3-(4-(3-Aminopropoxy)butoxy)propylamino)-6-(2,2,2-trifluoroethoxy)-1,3,5-triazin-2-ylamino)benzoic acid | |
|---|---|
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 4: To a solution of 4-(4-(3-(4-(3-aminopropoxy)butoxy)propylamino)-6-(2,2,2-trifluoroethoxy)-1,3,5-triazin-2-ylamino)benzoic acid (30 mg) in DMF (8 mL) was added TBTU (20.51 mg) and iPr$_2$NEt (0.081 mL). The mixture was stirred at r.t. for 16 hours before all solvents were removed under vacuum. The residue was purified via prep. HPLC to give compound 0004.

| Compound 0004 | |
|---|---|
| MS (M + H)+ Calcd. | 499.2 |
| MS (M + H)+ Observ. | 499.2 |
| Retention Time | 1.71 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Synthesis of Compound 0005:

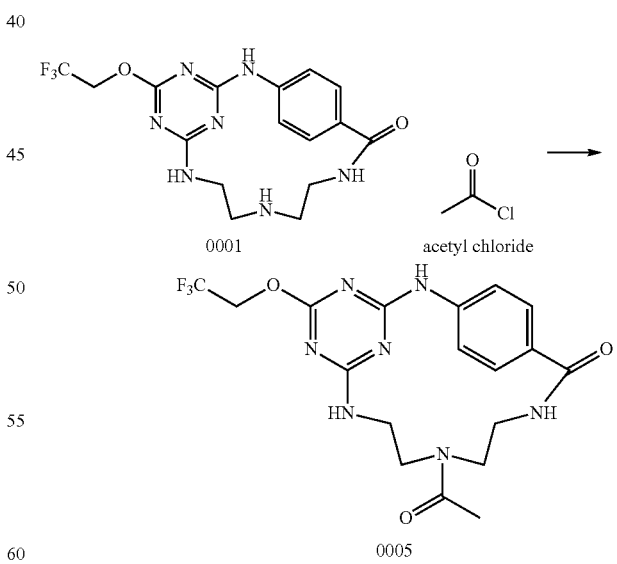

Acetyl chloride (0.02 g) and iPr2Net (0.033 g) were added into the solution of compound 0001 (0.05 g) in THF (2 mL). The mixture was stirred at r.t. for 2 hours before all the solvents were removed under vacuum. The residue was purified via prep. HPLC to give compound 0005 (0.003 g).

| Compound 0005 | |
|---|---|
| MS (M + H)⁺ Calcd. | 440.2 |
| MS (M + H)⁺ Observ. | 440.2 |
| Retention Time | 1.75 min |
| LC Condition | |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water - Methanol- TFA |
| Column | PHENOMENEX-LUNA 4.6 × 50 mm S10 |

Synthesis of Compound 0006:

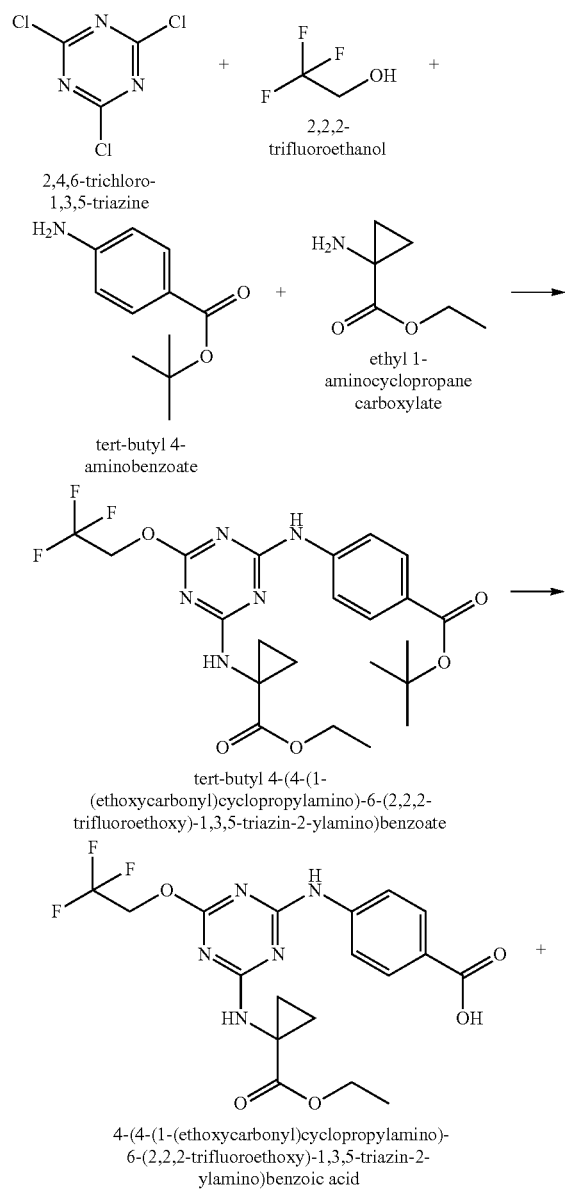

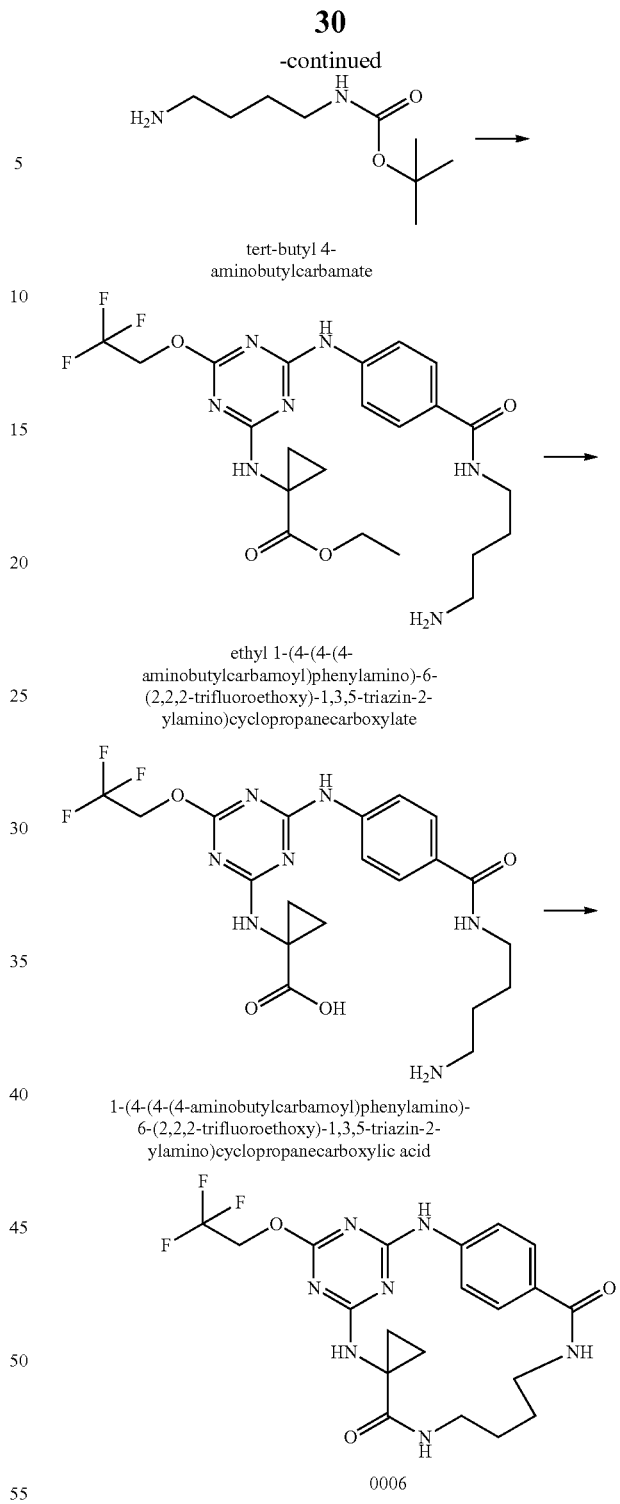

Step 1: iPr2NEt (10 mL) was added into the solution of 2,4,6-trichloro-1,3,5-triazine (2.5 g) and 2,2,2-trifluoroethanol (1.36 g) in THF (100 mL). The reaction was stirred at room temperature for 16 hours before tert-butyl 4-aminobenzoate (2.62 g) was added. The resulting mixture was stirred at room temperature for 40 hours. Then, ethyl 1-aminocyclopropanecarboxylate hydrochloride (2.25 g) was added into the mixture. The reaction was carried out at r.t. for 16 hours, then 115° C. for 16 hours. The reaction was quenched with water. The aqueous layer was extracted with EtOAc (3×100 mL). The combined organic layer was dried over Mg₂SO₄ and concentrated to offer a residue which will be purified by silica gel chromatography.

| tert-Butyl 4-(4-(1-(ethoxycarbonyl)cyclopropylamino)-6-(2,2,2-trifluoroethoxy)-1,3,5-triazin-2-ylamino)benzoate | |
|---|---|
| MS (M + H)⁺ Calcd. | 498.2 |
| MS (M + H)⁺ Observ. | 498.3 |
| Retention Time | 2.05 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: To a suspension of tert-butyl 4-(4-(1-(ethoxycarbonyl)cyclopropylamino)-6-(2,2,2-trifluoroethoxy)-1,3,5-triazin-2-ylamino)benzoate (1.6 g) in dichloromethane (15 mL) was added TFA (4.96 mL). The mixture was stirred at r.t. for 16 hours. All solvents were removed under vacuum to give product 4-(4-(1-(ethoxycarbonyl)cyclopropylamino)-6-(2,2,2-trifluoroethoxy)-1,3,5-triazin-2-ylamino)benzoic acid (1.35 g).

| 4-(4-(1-(Ethoxycarbonyl)cyclopropylamino)-6-(2,2,2-trifluoroethoxy)-1,3,5-triazin-2-ylamino)benzoic acid | |
|---|---|
| MS (M + H)⁺ Calcd. | 442.1 |
| MS (M + H)⁺ Observ. | 442.3 |
| Retention Time | 1.29 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: To a solution of 4-(4-(1-(ethoxycarbonyl)cyclopropylamino)-6-(2,2,2-trifluoroethoxy)-1,3,5-triazin-2-ylamino)benzoic acid (100 mg) in DMF (5 mL) was added tert-butyl 4-aminobutylcarbamate (64.0 mg), 2-(1H-benzotriazol-1-yl)-1,1,3,3-tetramethyluronium tetrafluoroborate (109 mg) and iPr₂NEt (0.119 mL). The mixture was stirred at r.t. for 16 hours before all the solvents were removed under vacuum. The residue was dissolved in dichloromethane (5.00 mL) and 2 mL of TFA. The mixture was stirred at r.t. for 3 hours. All solvents were removed under vacuum and the residue was purified by prep. HPLC to give ethyl 1-(4-(4-(4-aminobutylcarbamoyl)phenylamino)-6-(2,2,2-trifluoroethoxy)-1,3,5-triazin-2-ylamino)cyclopropanecarboxylate (80 mg).

| Ethyl 1-(4-(4-(4-aminobutylcarbamoyl)phenylamino)-6-(2,2,2-trifluoroethoxy)-1,3,5-triazin-2-ylamino)cyclopropanecarboxylate | |
|---|---|
| MS (M + H)⁺ Calcd. | 512.2 |
| MS (M + H)⁺ Observ. | 512.1 |
| Retention Time | 2.18 min |
| LC Condition | |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water - Methanol- TFA |
| Column | PHENOMENEX-LUNA 3.0 × 50 mm S10 |

Step 4: Ethyl 1-(4-(4-(4-aminobutylcarbamoyl)phenylamino)-6-(2,2,2-trifluoroethoxy)-1,3,5-triazin-2-ylamino)cyclopropanecarboxylate (80 mg) and potassium carbonate (64.8 mg) were dissolved in acetone (3 mL)/water (2 mL). After stirring at r.t. for 16 hours and then heated to 90° C. for 2 hours, the mixture was acidified with 1N HCl to pH=3. All the solvents were then removed under vacuum. The residue was purified by perp. HPLC to give 1-(4-(4-(4-aminobutylcarbamoyl)phenylamino)-6-(2,2,2-trifluoroethoxy)-1,3,5-triazin-2-ylamino)cyclopropanecarboxylic acid (20 mg).

| 1-(4-(4-(4-Aminobutylcarbamoyl)phenylamino)-6-(2,2,2-trifluoroethoxy)-1,3,5-triazin-2-ylamino)cyclopropanecarboxylic acid | |
|---|---|
| MS (M + H)⁺ Calcd. | 484.2 |
| MS (M + H)⁺ Observ. | 484.3 |
| Retention Time | 1.21 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 5: To a solution of 1-(4-(4-(4-aminobutylcarbamoyl)phenylamino)-6-(2,2,2-trifluoroethoxy)-1,3,5-triazin-2-ylamino)cyclopropanecarboxylic acid (20 mg) in THF (80 mL) was added TBTU (19.92 mg) and iPr₂NEt (0.022 mL). The mixture was stirred at r.t. for 16 hours before all the solvents were removed under vacuum. All solvents were removed under vacuum and the residue was purified by prep. HPLC to give compound 0006 (5.8 mg).

Compound 0006

| | |
|---|---|
| MS (M + H)+ Calcd. | 466.2 |
| MS (M + H)+ Observ. | 466.2 |
| Retention Time | 2.94 min |

LC Condition

| | |
|---|---|
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water - Methanol- TFA |
| Column | PHENOMENEX-LUNA 3.0 × 50 mm S10 |

Syntheses of Compounds 0007:

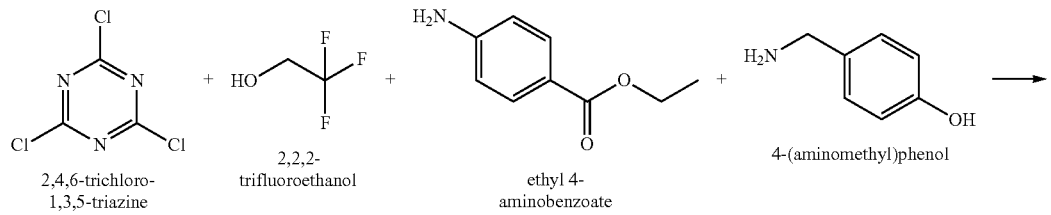

2,4,6-trichloro-1,3,5-triazine + 2,2,2-trifluoroethanol + ethyl 4-aminobenzoate + 4-(aminomethyl)phenol →

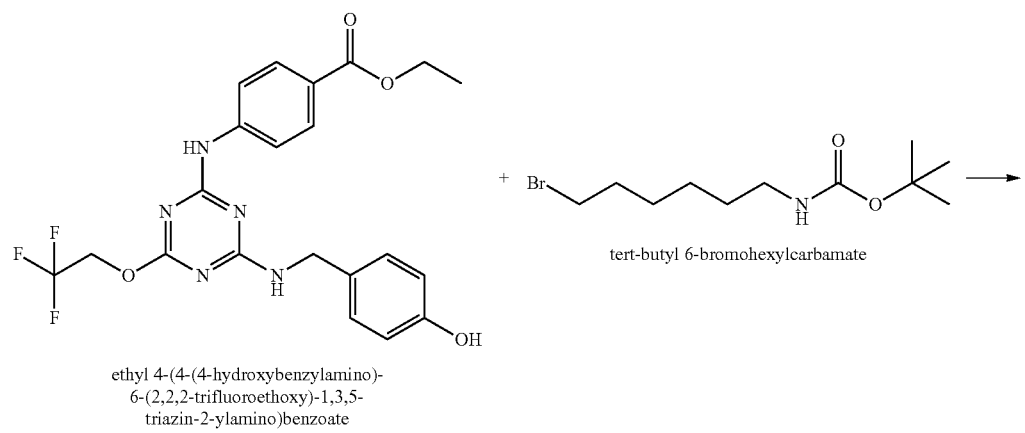

ethyl 4-(4-(4-hydroxybenzylamino)-6-(2,2,2-trifluoroethoxy)-1,3,5-triazin-2-ylamino)benzoate + tert-butyl 6-bromohexylcarbamate →

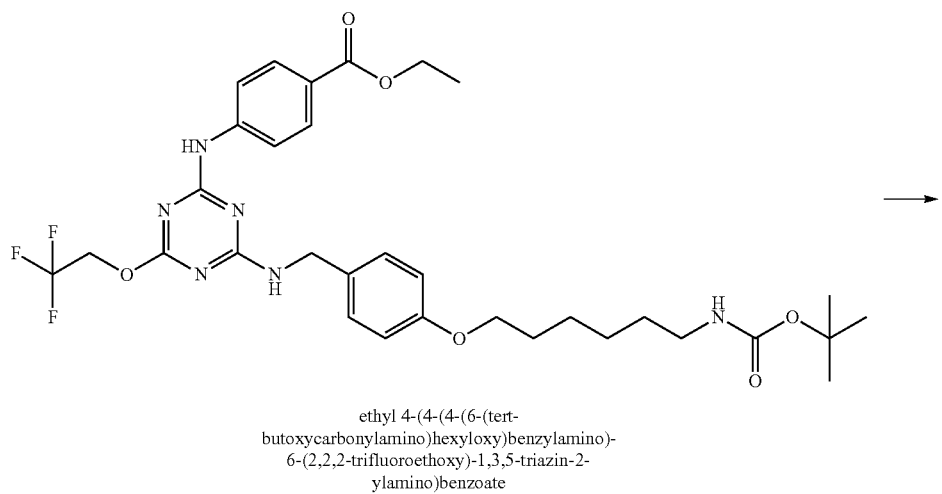

ethyl 4-(4-(4-(6-(tert-butoxycarbonylamino)hexyloxy)benzylamino)-6-(2,2,2-trifluoroethoxy)-1,3,5-triazin-2-ylamino)benzoate -continued
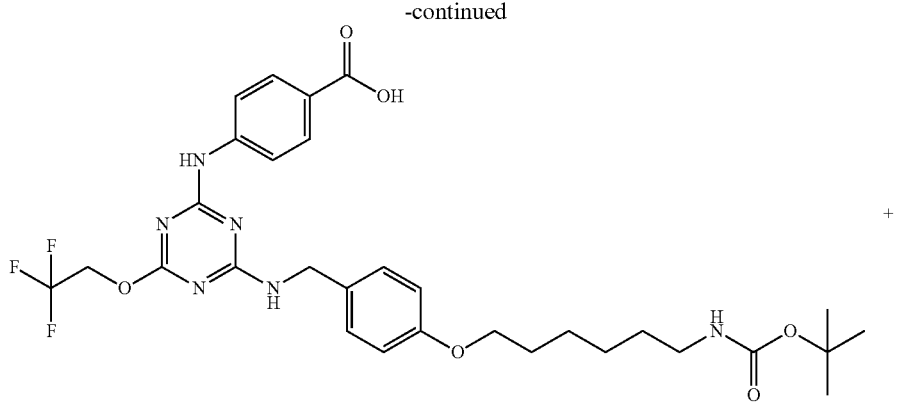
4-(4-(4-(6-(tert-butoxycarbonylamino)hexyloxy)benzylamino)-6-(2,2,2-trifluorethoxy)-1,3,5-triazin-2-ylamino)benzoic acid
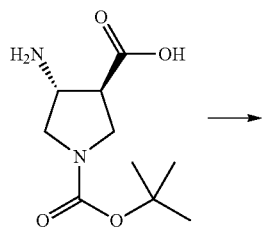
trans-4-amino-1-(tert-butoxycarbonyl)pyrrolidine-3-carboxylic acid
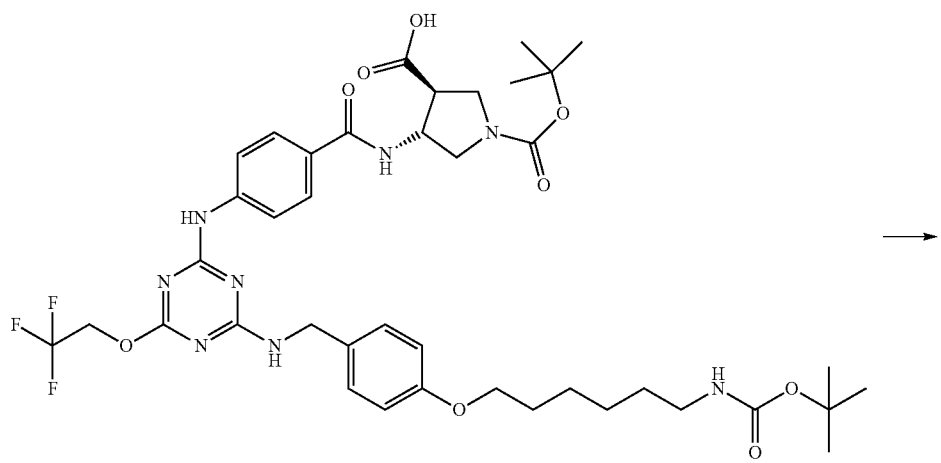
trans-1-(tert-butoxycarbonyl)-4-(4-(4-(4-(6-(tert-butoxycarbonylamino)hexyloxy)benzylamino)-6-(2,2,2-trifluoroethoxy)-1,3,5-triazin-2-ylamino)benzamido)pyrrolidine-3-carboxylic acid -continued

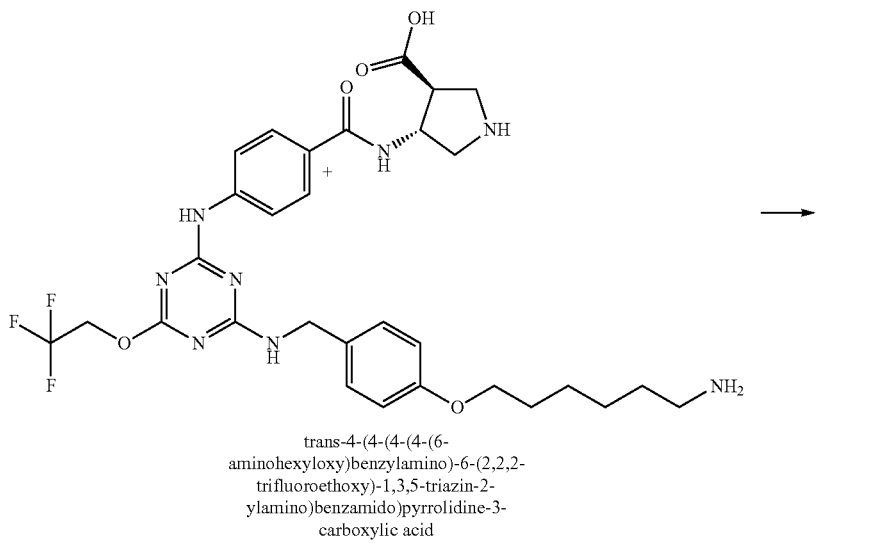

trans-4-(4-(4-(4-(6-aminohexyloxy)benzylamino)-6-(2,2,2-trifluoroethoxy)-1,3,5-triazin-2-ylamino)benzamido)pyrrolidine-3-carboxylic acid

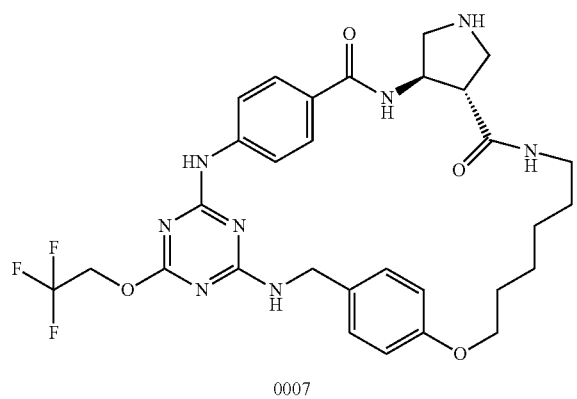

0007

Step 1: To a solution of 2,4,6-trichloro-1,3,5-triazine (10 g) in acetone (210 mL) was added a solution of 2,2,2-trifluoroethanol (5.97 g) and 2,4,6-collidine (7.88 mL) in acetone (210 mL) dropwise over 1 hour. The resulting mixture was stirred at room temperature for 16 hours. All the solvents were removed under vacuum to give a residue which was diluted with NMP (100 mL) and ethyl 4-aminobenzoate (9.85 g), iPr₂NEt (28.4 mL) were added. After stirring at room temperature for 6 hours, 4-(aminomethyl)phenol (7.35 g) was added. The resulting mixture was stirred for 16 hours at room temperature. The mixture was diluted with 300 mL of water and extracted with EtOAc (2×500 mL). The organic layers were combined, washed with brine (300 mL), dried over MgSO₄ and concentrated. The residue was purified by recrystallization in MeOH to give ethyl 4-(4-(4-hydroxybenzylamino)-6-(2,2,2-trifluoroethoxy)-1,3,5-triazin-2-ylamino)benzoate (13.6 g).

| ethyl 4-(4-(4-hydroxybenzylamino)-6-(2,2,2-trifluoroethoxy)-1,3,5-triazin-2-ylamino)benzoate | |
|---|---|
| MS (M + H)⁺ Calcd. | 464.1 |
| MS (M + H)⁺ Observ. | 464.3 |
| Retention Time | 1.75 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: To a solution of ethyl 4-(4-(4-hydroxybenzylamino)-6-(2,2,2-trifluoroethoxy)-1,3,5-triazin-2-ylamino) benzoate (1.5 g) in DMF (8 mL) was added tert-butyl 6-bromohexylcarbamate (1.1 g) and $K_2CO_3$ (0.9 g). The mixture was heated to 65° C. for 16 hours. After cooling to room temperature, the mixture was diluted with EtOAc (250 mL) and washed with water (50 mL) and brine (50 mL). The organic layer was dried over $MgSO_4$ and concentrated. The residue was purified by recrystallization in MeOH to give ethyl 4-(4-(4-(6-(tert-butoxycarbonylamino)hexyloxy)benzylamino)-6-(2,2,2-trifluoroethoxy)-1,3,5-triazin-2-ylamino)benzoate (1.2 g).

| ethyl 4-(4-(4-(6-(tert-butoxycarbonylamino)hexyloxy)benzylamino)-6-(2,2,2-trifluoroethoxy)-1,3,5-triazin-2-ylamino)benzoate | |
|---|---|
| MS (M + H)$^+$ Calcd. | 663.3 |
| MS (M + H)$^+$ Observ. | 663.2 |
| Retention Time | 3.98 min |
| LC Condition | |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water - Methanol- TFA |
| Column | PHENOMENEX-LUNA 3.0 × 50 mm S10 |

Step 3: A mixture of ethyl 4-(4-(4-(6-(tert-butoxycarbonylamino)hexyloxy)benzylamino)-6-(2,2,2-trifluoroethoxy)-1,3,5-triazin-2-ylamino)benzoate (1.0 g) and $K_2CO_3$ (1.25 g) in acetone (12 mL)/water (12 mL) was heated at 110° C. for 24 hours. After cooling to room temperature, the mixture was acidified with 1N HCl to pH=3. The white precipitate was collected, washed with water (20 mL) and dried under vacuum to give 4-(4-(4-(6-(tert-butoxycarbonylamino)hexyloxy)benzylamino)-6-(2,2,2-trifluoroethoxy)-1,3,5-triazin-2-ylamino)benzoic acid (0.72 g).

| 4-(4-(4-(6-(tert-butoxycarbonylamino)hexyloxy)benzylamino)-6-(2,2,2-trifluoroethoxy)-1,3,5-triazin-2-ylamino)benzoic acid | |
|---|---|
| MS (M + H)$^+$ Calcd. | 635.3 |
| MS (M + H)$^+$ Observ. | 635.1 |
| Retention Time | 3.73 min |
| LC Condition | |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water - Methanol- TFA |
| Column | PHENOMENEX-LUNA 3.0 × 50 mm S10 |

Step 4: To a solution of 4-(4-(4-(6-(tert-butoxycarbonylamino)hexyloxy)benzylamino)-6-(2,2,2-trifluoroethoxy)-1,3,5-triazin-2-ylamino)benzoic acid (200 mg), trans-4-amino-1-Boc-pyrrolidine-3-carboxylic acid (72.6 mg) and O-benzotriazol-1-yl-N,N,N',N'-tetra-methyluronium tetrafluoroborate (121 mg) was added iPr$_2$NEt (0.22 mL). The mixture was stirred at room temperature for 4 hours. The mixture was purified by preparative HPLC to give trans-1-(tert-butoxycarbonyl)-4-(4-(4-(4-(6-(tert-butoxycarbonylamino)hexyloxy)benzylamino)-6-(2,2,2-trifluoroethoxy)-1,3,5-triazin-2-ylamino)benzamido)pyrrolidine-3-carboxylic acid (32 mg).

| trans-1-(tert-butoxycarbonyl)-4-(4-(4-(6-(tert-butoxycarbonylamino)hexyloxy)benzylamino)-6-(2,2,2-trifluoroethoxy)-1,3,5-triazin-2-ylamino)benzamido)pyrrolidine-3-carboxylic acid | |
|---|---|
| MS (M + H)$^+$ Calcd. | 847.4 |
| MS (M + H)$^+$ Observ. | 847.4 |
| Retention Time | 1.70 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 5: To a suspension of trans-1-(tert-butoxycarbonyl)-4-(4-(4-(4-(6-(tert-butoxycarbonylamino)hexyloxy)benzylamino)-6-(2,2,2-trifluoroethoxy)-1,3,5-triazin-2-ylamino)benzamido)pyrrolidine-3-carboxylic acid (32 mg) was added TFA (0.2 mL). The mixture was heated at 60° C. for 3 hours. All solvents were removed under vacuum. The residue was used for next step reaction without further purification.

| trans-4-(4-(4-(4-(6-aminohexyloxy)benzylamino)-6-(2,2,2-trifluoroethoxy)-1,3,5-triazin-2-ylamino)benzamido)pyrrolidine-3-carboxylic acid | |
|---|---|
| MS (M + H)$^+$ Calcd. | 647.3 |
| MS (M + H)$^+$ Observ. | 647.4 |
| Retention Time | 1.21 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 6: To a solution of trans-4-(4-(4-(4-(6-aminohexyloxy)benzylamino)-6-(2,2,2-trifluoroethoxy)-1,3,5-triazin-2-ylamino)benzamido)pyrrolidine-3-carboxylic acid (23 mg) and O-benzotriazol-1-yl-N,N,N',N'-tetra-methyluronium tetrafluoroborate (13.7 mg) was added iPr₂NEt (0.012 mL). The mixture was stirred at room temperature for 2 hours. DMF was removed under vacuum. The residue was purified by preparative HPLC to give Compound 0007 (6.3 mg).

| Compound 0007 | |
| --- | --- |
| MS (M + H)⁺ Calcd. | 629.3 |
| MS (M + H)⁺ Observ. | 629.4 |
| Retention Time | 1.43 min |

| Compound 0007 | |
| --- | --- |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Syntheses of Compounds 0008:

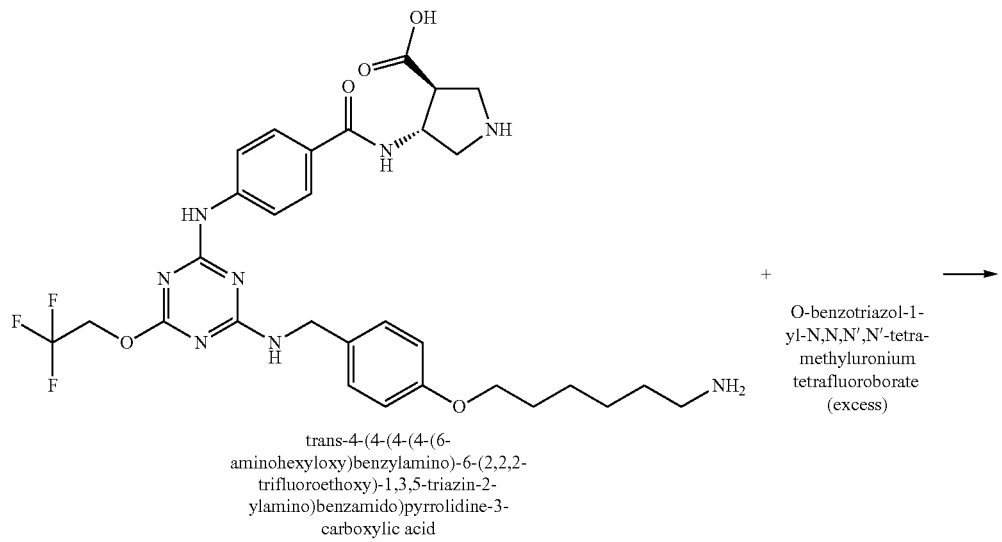

trans-4-(4-(4-(4-(6-aminohexyloxy)benzylamino)-6-(2,2,2-trifluoroethoxy)-1,3,5-triazin-2-ylamino)benzamido)pyrrolidine-3-carboxylic acid + O-benzotriazol-1-yl-N,N,N',N'-tetra-methyluronium tetrafluoroborate (excess) →

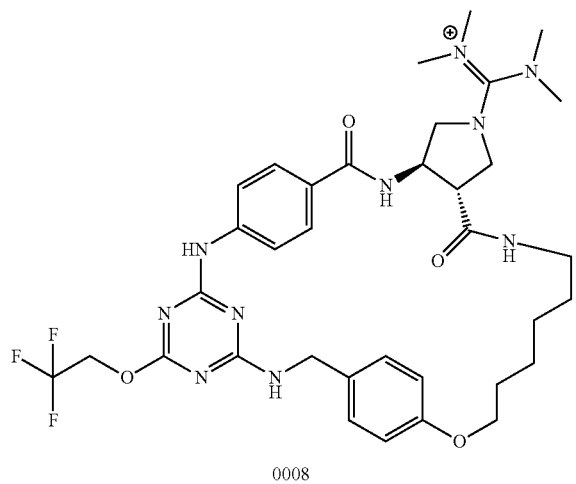

0008

To a solution of 4-(4-(4-(4-(6-aminohexyloxy)benzylamino)-6-(2,2,2-trifluoroethoxy)-1,3,5-triazin-2-ylamino)benzamido)pyrrolidine-3-carboxylic acid (83 mg) in DMF (5 mL) was added O-benzotriazol-1-yl-N,N,N',N'-tetra-methyluronium tetrafluoroborate (103 mg) and iPr$_2$NEt (0.067 mL). After stirring at room temperature for 4 hours, the mixture was purified by preparative HPLC to give Compound 0008 (15 mg).

| Compound 0008 | |
|---|---|
| MS M⁺ Calcd. | 727.4 |
| MS M⁺ Observ. | 727.5 |
| Retention Time | 1.62 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Syntheses of Compounds 0009 and 0010:

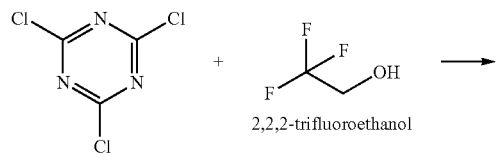

2,4,6-trichloro-1,3,5-triazine + 2,2,2-trifluoroethanol

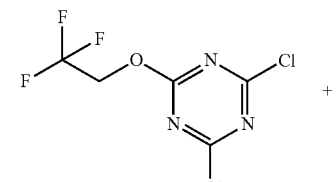

2,4-dichloro-(2,2,2-trifluoroethoxy)-1,3,5-triazine

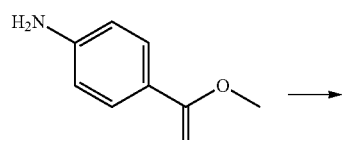

methyl 4-aminobenzoate

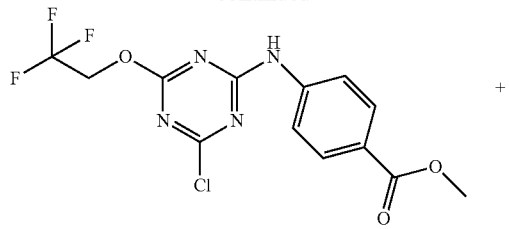

methyl 4-(4-chloro-6-(2,2,2-trifluoroethoxy)-1,3,5-triazin-2-ylamino)benzoate

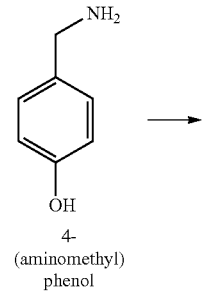

4-(aminomethyl)phenol

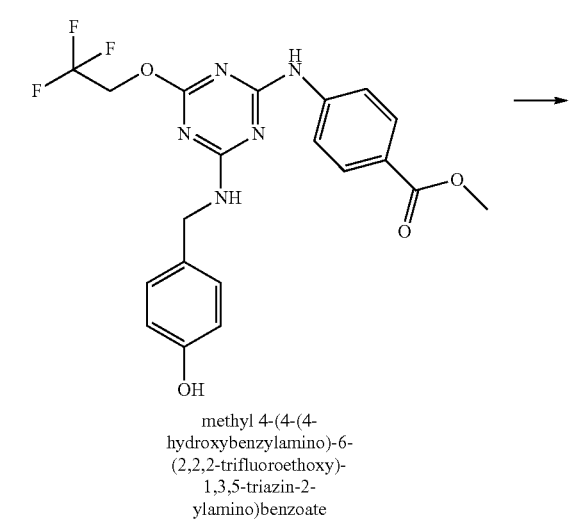

methyl 4-(4-(4-hydroxybenzylamino)-6-(2,2,2-trifluoroethoxy)-1,3,5-triazin-2-ylamino)benzoate

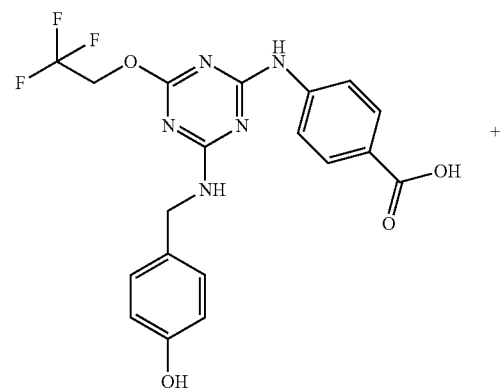

4-(4-(4-hydroxybenzylamino)-6-(2,2,2-trifluoroethoxy)-1,3,5-triazin-2-ylamino)benzoic acid -continued

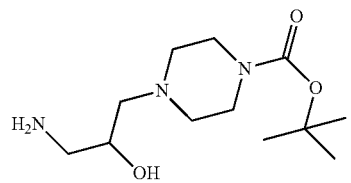

tert-butyl 4-(3-amino-2-hydroxypropyl)piperazine-1-carboxylate

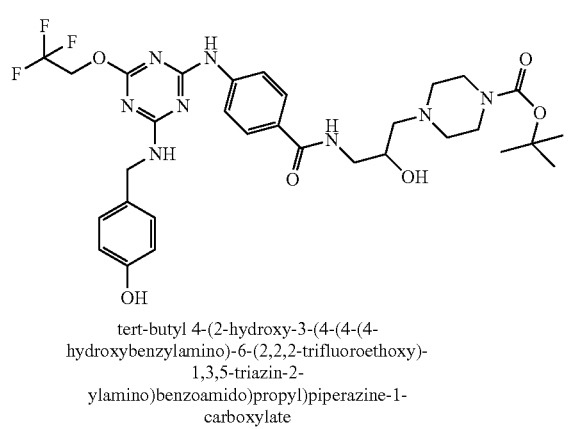

tert-butyl 4-(2-hydroxy-3-(4-(4-(4-hydroxybenzylamino)-6-(2,2,2-trifluoroethoxy)-1,3,5-triazin-2-ylamino)benzoamido)propyl)piperazine-1-carboxylate

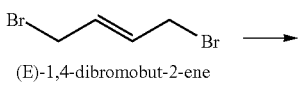

(E)-1,4-dibromobut-2-ene

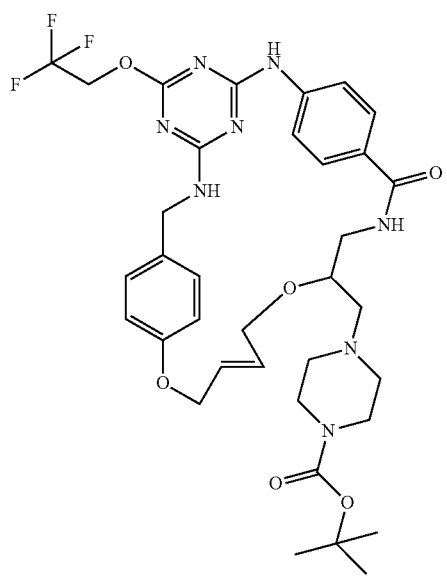

0009

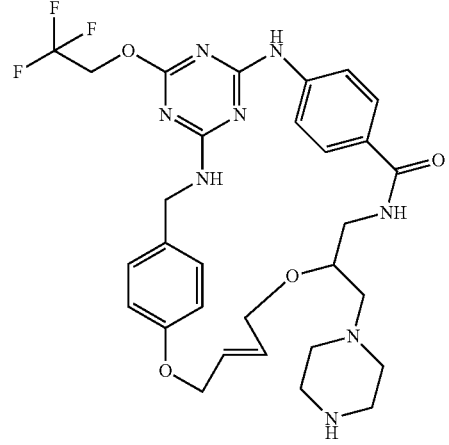

0010

Step 1: 2,2,2-Trifluoroethanol (4.9 g) and iPr₂NEt (6.3 g) were added into a solution of 2,4,6-trichloro-1,3,5-triazine (9.0 g) in THF (500 mL). The mixture was stirred at room temperature for 16 hours before being carried to the Step 2 directly.

Step 2: Methyl 4-aminobenzoate (7.26 g) and iPr₂NEt (6.20 g) were added into the reaction mixture from Step 1. The reaction was stirred at room temperature for 16 hours before solvents were removed under vacuum. The residue was partitioned with 25 mL of water and 100 mL of EtOAc, and the suspension mixture was stirred at room temperature for 16 hours. Filtration offered 12.0 g of methyl 4-(4-chloro-6-(2,2,2-trifluoroethoxy)-1,3,5-triazin-2-ylamino)benzoate as white solid.

| methyl 4-(4-chloro-6-(2,2,2-trifluoroethoxy)-1,3,5-triazin-2-ylamino)benzoate | |
|---|---|
| MS (M + H)⁺ Calcd. | 363.0 |
| MS (M + H)⁺ Observ. | 363.1 |
| Retention Time | 3.05 min |
| LC Condition | |
| Solvent A | 5% ACN:95% Water:10 mm Ammonium Actetate |
| Solvent B | 95% ACN:5% Water:10 mm Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Step 3: 4-(aminomethyl)phenol (2.4 g) white solid and iPr₂NEt (5.0 g) were added into a solution of methyl 4-(4-chloro-6-(2,2,2-trifluoroethoxy)-1,3,5-triazin-2-ylamino)benzoate (7.0 g) in THF (150 mL). The mixture was heated at 70° C. for 16 hours. After cooling, the mixture was charged with 250 mL of EtOAc. The resulting solution was washed with water (2×50 mL) and brine (30 mL). The organic layer was dried over MgSO₄ and concentrated under vacuum to give a residue which was recrystallized in EtOAc to give 6.54 g of methyl 4-(4-(4-hydroxybenzylamino)-6-(2,2,2-trifluoroethoxy)-1,3,5-triazin-2-ylamino)benzoate.

| methyl 4-(4-(4-hydroxybenzylamino)-6-(2,2,2-trifluoroethoxy)-1,3,5-triazin-2-ylamino)benzoate | |
|---|---|
| MS (M + H)+ Calcd. | 450.1 |
| MS (M + H)+ Observ. | 450.3 |
| Retention Time | 2.86 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Step 4: A solution of methyl 4-(4-(4-hydroxybenzylamino)-6-(2,2,2-trifluoroethoxy)-1,3,5-triazin-2-ylamino)benzoate (0.5 g) and potassium carbonate (0.461 g) in dioxane (9 mL) and water (9 mL) in sealed tube was heated at 105° C. for 16 hours. After cooling, the mixture was charged with 1N HCl solution to pH=1. Solvents were removed under vacuum to give a residue which was washed with water (2 mL). White solid, 4-(4-(4-hydroxybenzylamino)-6-(2,2,2-trifluoroethoxy)-1,3,5-triazin-2-ylamino)benzoic acid, was collected and dried at 78° C. under vacuum for 16 hours to weigh 0.35 g.

| 4-(4-(4-hydroxybenzylamino)-6-(2,2,2-trifluoroethoxy)-1,3,5-triazin-2-ylamino)benzoic acid | |
|---|---|
| MS (M + H)+ Calcd. | 436.1 |
| MS (M + H)+ Observ. | 436.0 |
| Retention Time | 1.69 min |
| | LC Condition |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water - Methanol- TFA |
| Column | PHENOMENEX-LUNA 4.6 × 50 mm S10 |

Step 5: N,N-diisopropylethylamine (0.30 g) and O-benzotriazol-1-yl-N,N,N',N'-tetra-methyluronium tetrafluoroborate (0.44 g) were added into a solution of 4-(4-(4-hydroxybenzylamino)-6-(2,2,2-trifluoroethoxy)-1,3,5-triazin-2-ylamino)benzoic acid (0.5 g) and tert-butyl 4-(3-amino-2-hydroxypropyl)piperazine-1-carboxylate (0.33 g) in DMF (2 mL). The mixture was stirred at room temperature for 16 hours. Then, 50 mL of EtOAc was added into the reaction mixture which was sequentially washed with water (2×20 mL) and brine (15 mL). The organic layer was dried over MgSO4 and concentrated under vacuum to give a residue which was purified by silica gel chromatography to provide tert-butyl 4-(2-hydroxy-3-(4-(4-(4-hydroxybenzylamino)-6-(2,2,2-trifluoroethoxy)-1,3,5-triazin-2-ylamino)benzamido)propyl)piperazine-1-carboxylate (0.20 g).

| tert-butyl 4-(2-hydroxy-3-(4-(4-(4-hydroxybenzylamino)-6-(2,2,2-trifluoroethoxy)-1,3,5-triazin-2-ylamino)benzamido)propyl)piperazine-1-carboxylate | |
|---|---|
| MS (M + H)+ Calcd. | 677.3 |
| MS (M + H)+ Observ. | 677.2 |
| Retention Time | 1.53 min |
| | LC Condition |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water - Methanol- TFA |
| Column | PHENOMENEX-LUNA 4.6 × 50 mm S10 |

Step 6: (E)-1,4-dibromobut-2-ene (25 mg) and potassium carbonate (49 mg) were added into a solution of tert-butyl 4-(2-hydroxy-3-(4-(4-(4-hydroxybenzylamino)-6-(2,2,2-trifluoroethoxy)-1,3,5-triazin-2-ylamino)benzamido)propyl)piperazine-1-carboxylate (80 mg) in DMF (3 mL). The mixture was stirred at room temperature for 16 hours. The Compound 0009 (10 mg) was isolated by preparative HPLC as white solid.

| Compound 0009 | |
|---|---|
| MS (M + H)+ Calcd. | 729.3 |
| MS (M + H)+ Observ. | 729.7 |
| Retention Time | 3.76 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Step 7: TFA (6.34 µL) was added into a solution of Compound 0009 (4 mg) in dichloromethane (1 mL). The mixture was stirred at room temperature for 16 hours. Removal of solvents under vacuum offered a residue which was purified by preparative HPLC to give Compound 0010 (3 mg).

| Compound 0010 | |
|---|---|
| MS (M + H)+ Calcd. | 629.3 |
| MS (M + H)+ Observ. | 629.3 |
| Retention Time | 3.66 min |
| | LC Condition |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water - Methanol- TFA |
| Column | PHENOMENEX-LUNA 2.0 × 50 mm 3 um |

Syntheses of Compounds 0011:

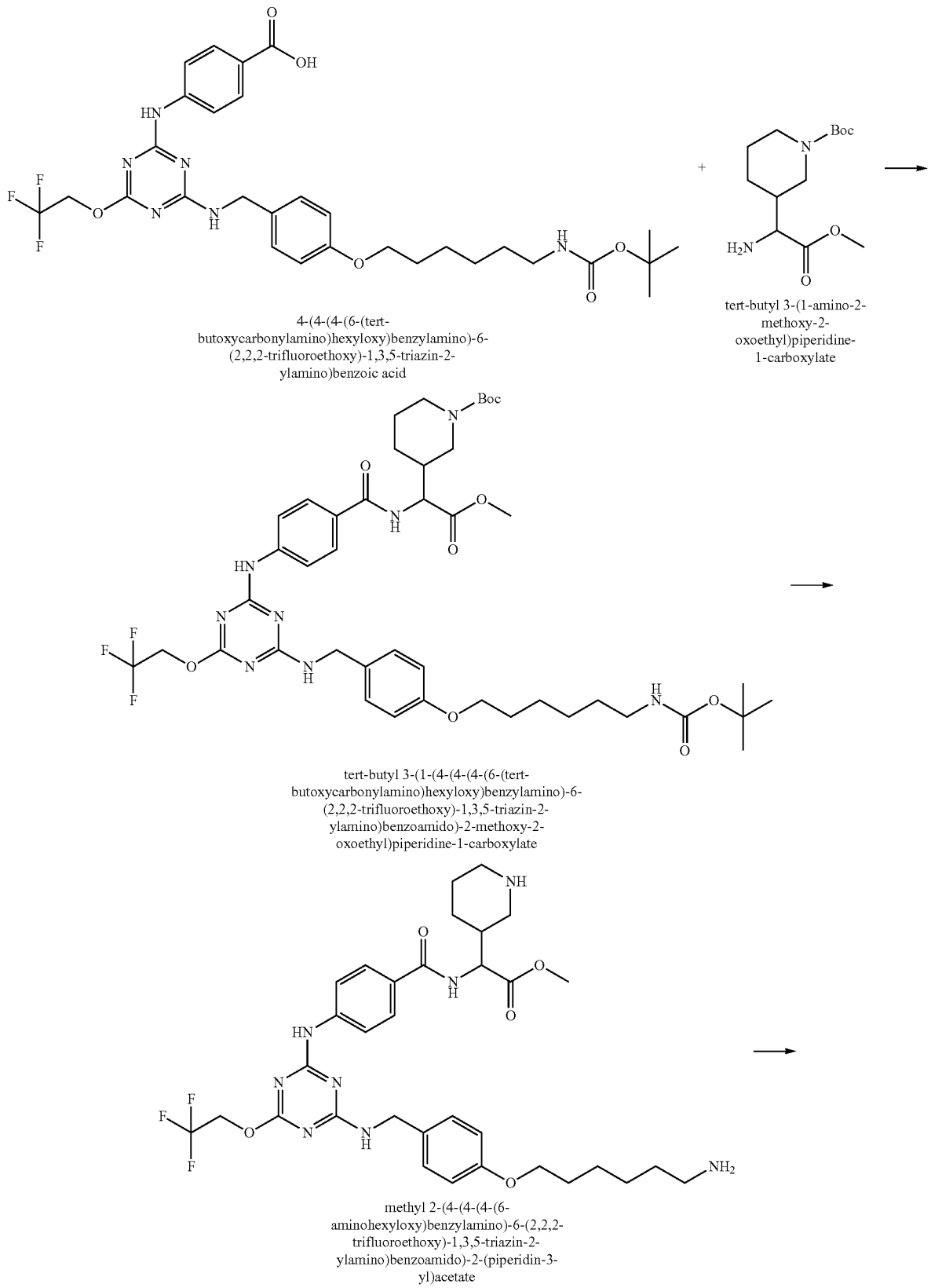

4-(4-(4-(6-(tert-butoxycarbonylamino)hexyloxy)benzylamino)-6-(2,2,2-trifluoroethoxy)-1,3,5-triazin-2-ylamino)benzoic acid tert-butyl 3-(1-amino-2-methoxy-2-oxoethyl)piperidine-1-carboxylate tert-butyl 3-(1-(4-(4-(6-(tert-butoxycarbonylamino)hexyloxy)benzylamino)-6-(2,2,2-trifluoroethoxy)-1,3,5-triazin-2-ylamino)benzoamido)-2-methoxy-2-oxoethyl)piperidine-1-carboxylate methyl 2-(4-(4-(4-(6-aminohexyloxy)benzylamino)-6-(2,2,2-trifluoroethoxy)-1,3,5-triazin-2-ylamino)benzoamido)-2-(piperidin-3-yl)acetate

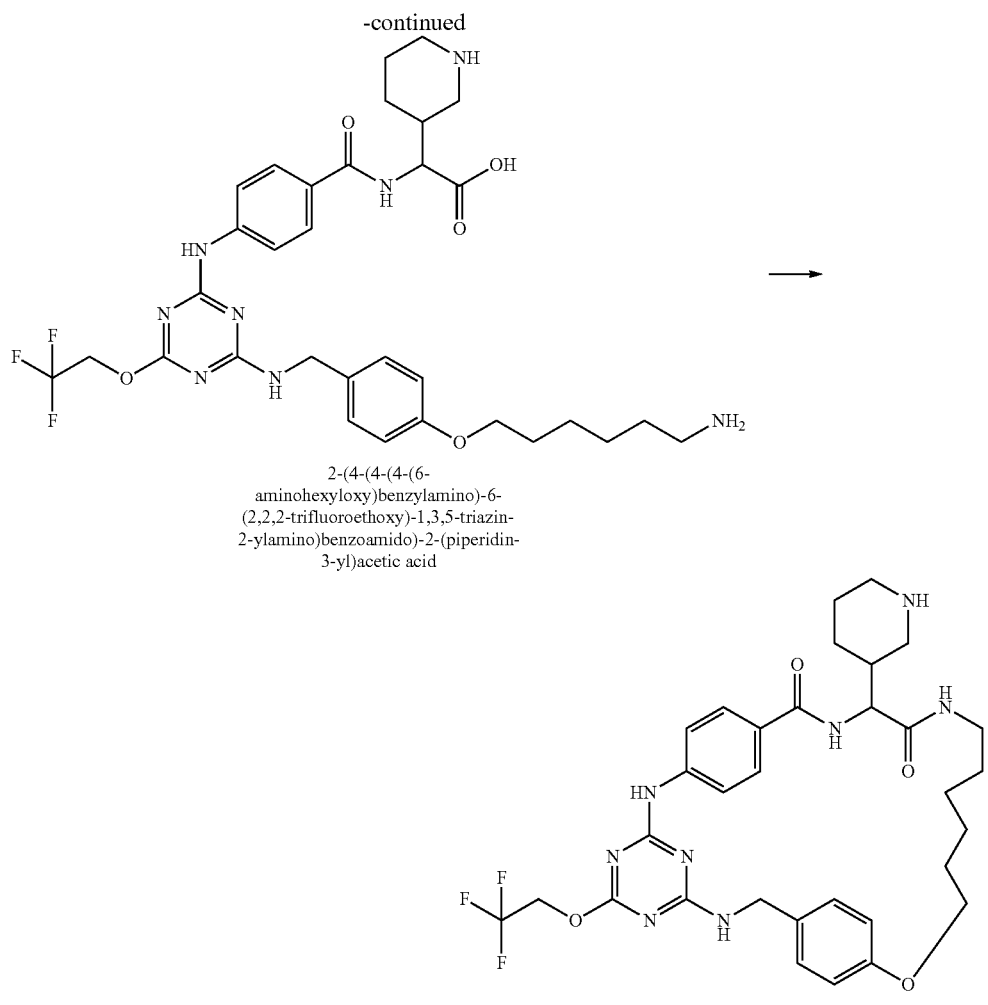

2-(4-(4-(4-(6-aminohexyloxy)benzylamino)-6-(2,2,2-trifluoroethoxy)-1,3,5-triazin-2-ylamino)benzoamido)-2-(piperidin-3-yl)acetic acid

0011

Step 1: To a solution of 4-(4-(4-(6-(tert-butoxycarbonylamino)hexyloxy)benzylamino)-6-(2,2,2-trifluoroethoxy)-1,3,5-triazin-2-ylamino)benzoic acid (100 mg), tert-butyl 3-(1-amino-2-methoxy-2-oxoethyl)piperidine-1-carboxylate (51.5 mg) and O-benzotriazol-1-yl-N,N,N',N'-tetra-methyluronium tetrafluoroborate (60.7 mg) was added iPr$_2$NEt (0.055 mL). The mixture was stirred at room temperature for 4 hours. The mixture was purified by preparative HPLC to give tert-butyl 3-(1-(4-(4-(4-(6-(tert-butoxycarbonylamino)hexyloxy)benzylamino)-6-(2,2,2-trifluoroethoxy)-1,3,5-triazin-2-ylamino)benzamido)-2-methoxy-2-oxoethyl)piperidine-1-carboxylate (80 mg).

| tert-butyl 3-(1-(4-(4-(4-(6-(tert-butoxycarbonylamino)hexyloxy)benzylamino)-6-(2,2,2-trifluoroethoxy)-1,3,5-triazin-2-ylamino)benzamido)-2-methoxy-2-oxoethyl)piperidine-1-carboxylate | |
|---|---|
| MS (M + H)$^+$ Calcd. | 889.4 |
| MS (M + H)$^+$ Observ. | 889.5 |
| Retention Time | 2.16 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Step 2: To a solution of tert-butyl 3-(1-(4-(4-(4-(6-(tert-butoxycarbonylamino)hexyloxy)benzylamino)-6-(2,2,2-trifluoroethoxy)-1,3,5-triazin-2-ylamino)benzamido)-2-methoxy-2-oxoethyl)piperidine-1-carboxylate (80 mg) in CH$_2$Cl$_2$ (2 mL) was added TFA (0.4 mL). The mixture was stirred at room temperature for 3 hours. All the solvents were removed under vacuum. The residue was used for next step reaction without further purification.

| methyl 2-(4-(4-(4-(6-aminohexyloxy)benzylamino)-6-(2,2,2-trifluoroethoxy)-1,3,5-triazin-2-ylamino)benzamido)-2-(piperidin-3-yl)acetate | |
|---|---|
| MS (M + H)⁺ Calcd. | 689.3 |
| MS (M + H)⁺ Observ. | 689.5 |
| Retention Time | 2.45 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Step 3: A mixture of methyl 2-(4-(4-(4-(6-aminohexyloxy)benzylamino)-6-(2,2,2-trifluoroethoxy)-1,3,5-triazin-2-ylamino)benzamido)-2-(piperidin-3-yl)acetate (50 mg) and $K_2CO_3$ (50.2 mg) in acetone (2 mL)/water (2 mL) was heated at 85° C. for 4 hours. After cooling to room temperature, the mixture was acidified with 1N HCl to pH=3. All the solvents were removed under vacuum. The residue was purified by preparative HPLC to give 2-(4-(4-(4-(6-aminohexyloxy)benzylamino)-6-(2,2,2-trifluoroethoxy)-1,3,5-triazin-2-ylamino)benzamido)-2-(piperidin-3-yl)acetic acid (40 mg).

| 2-(4-(4-(4-(6-aminohexyloxy)benzylamino)-6-(2,2,2-trifluoroethoxy)-1,3,5-triazin-2-ylamino)benzamido)-2-(piperidin-3-yl)acetic acid | |
|---|---|
| MS (M + H)⁺ Calcd. | 675.3 |
| MS (M + H)⁺ Observ. | 675.5 |
| Retention Time | 1.33 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Step 4: To a solution of 2-(4-(4-(4-(6-aminohexyloxy)benzylamino)-6-(2,2,2-trifluoroethoxy)-1,3,5-triazin-2-ylamino)benzamido)-2-(piperidin-3-yl)acetic acid (35 mg) in DMF (5 mL) was added TBTU (20.0 mg) and $iPr_2NEt$ (0.027 mL). After stirring at room temperature for 4 hours, the mixture was directly purified by preparative HPLC to give Compound 0011 (7.8 mg).

| Compound 0011 | |
|---|---|
| MS (M + H)⁺ Calcd. | 657.3 |
| MS (M + H)⁺ Observ. | 657.4 |
| Retention Time | 1.53 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Synthesis Compounds 0021-0024:

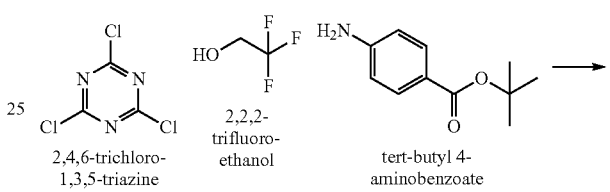

2,4,6-trichloro-1,3,5-triazine 2,2,2-trifluoro-ethanol tert-butyl 4-aminobenzoate

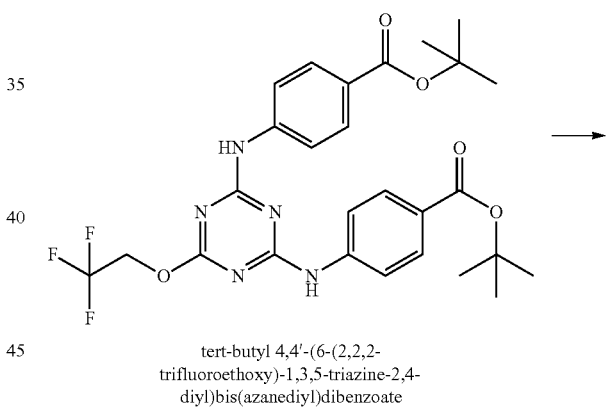

tert-butyl 4,4'-(6-(2,2,2-trifluoroethoxy)-1,3,5-triazine-2,4-diyl)bis(azanediyl)dibenzoate

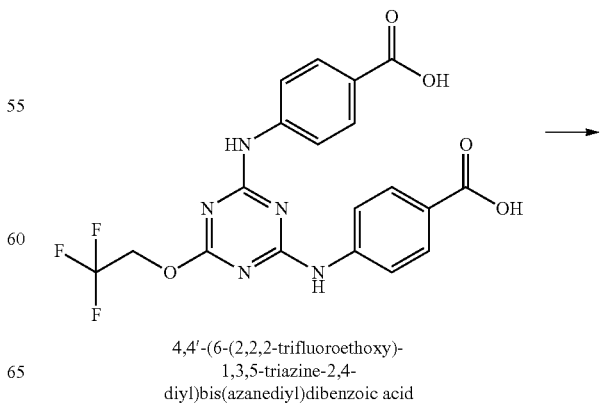

4,4'-(6-(2,2,2-trifluoroethoxy)-1,3,5-triazine-2,4-diyl)bis(azanediyl)dibenzoic acid -continued

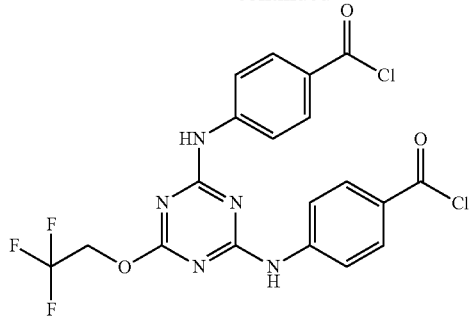

4,4'-(6-(2,2,2-trifluoroethoxy)-1,3,5-triazine-2,4-diyl)bis(azanediyl)dibenzoyl chloride

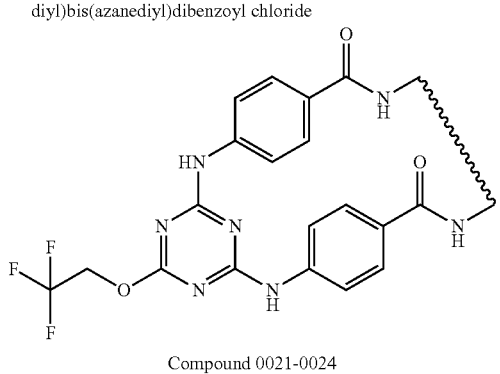

Compound 0021-0024

Step 1: To a solution of 2,4,6-trichloro-1,3,5-triazine (1.2 g) in acetone (30 mL) was added a solution of 2,2,2-trifluoroethanol (0.716 g) and 2,4,6-collidine (0.946 mL) in acetone (30.0 mL) dropwise over 15 minutes. The resulting mixture was stirred at room temperature for 16 hours. All solvents were removed under vacuum to give a residue which was diluted with NMP (10 mL) and tert-butyl 4-aminobenzoate (2.77 g), iPr$_2$NEt (3.41 mL) were added. The resulting mixture was stirred for 16 hours at room temperature and 16 hours at 65° C. The mixture was diluted with 100 mL of water and extracted with EtOAc (2×150 mL). The organic layers were combined, washed with brine (100 mL), dried over MgSO$_4$ and concentrated under vacuum to give the crude tert-butyl 4,4'-(6-(2,2,2-trifluoroethoxy)-1,3,5-triazine-2,4-diyl)bis(azanediyl)dibenzoate which was used in Step 2 without purification.

| tert-butyl 4,4'-(6-(2,2,2-trifluoroethoxy)-1,3,5-triazine-2,4-diyl)bis(azanediyl)dibenzoate | |
|---|---|
| MS (M + H)$^+$ Calcd. | 562.2 |
| MS (M + H)$^+$ Observ. | 562.1 |
| Retention Time | 4.17 min |
| LC Condition | |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water - Methanol- TFA |
| Column | PHENOMENEX-LUNA 3.0 × 50 mm S10 |

Step 2: To a solution of crude tert-butyl 4,4'-(6-(2,2,2-trifluoroethoxy)-1,3,5-triazine-2,4-diyl)bis(azanediyl) dibenzoate (562 mg) in CH$_2$Cl$_2$ (10 mL) was added TFA (3 mL). The mixture was stirred at room temperature for 16 hours. All solvents were removed under vacuum. The residue was purified by preparative HPLC to give 4,4'-(6-(2,2,2-trifluoroethoxy)-1,3,5-triazine-2,4-diyl)bis(azanediyl)dibenzoic acid (110 mg).

| 4,4'-(6-(2,2,2-trifluoroethoxy)-1,3,5-triazine-2,4-diyl)bis(azanediyl)dibenzoic acid | |
|---|---|
| MS (M + H)$^+$ Calcd. | 450.1 |
| MS (M + H)$^+$ Observ. | 449.9 |
| Retention Time | 3.19 min |
| LC Condition | |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water - Methanol- TFA |
| Column | PHENOMENEX-LUNA 3.0 × 50 mm S10 |

Step 3: To a suspension of 4,4'-(6-(2,2,2-trifluoroethoxy)-1,3,5-triazine-2,4-diyl)bis(azanediyl)dibenzoic acid (100 mg) in CH$_2$Cl$_2$ (4 mL) was added thionyl chloride (2 mL). The mixture was heated at 80° C. for 1 hour. All solvents were removed under vacuum. The residue, crude 4,4'-(6-(2,2,2-trifluoroethoxy)-1,3,5-triazine-2,4-diyl)bis(azanediyl) dibenzoyl chloride, was used in Step 4 without further purification.

Step 4: To a solution of 4,4'-(6-(2,2,2-trifluoroethoxy)-1,3,5-triazine-2,4-diyl)bis(azanediyl)dibenzoyl chloride (1. eq.) in CH$_2$Cl$_2$ was added a mixture of diamine (1 eq.) and iPr$_2$NEt (10 eq.) in CH$_2$Cl$_2$ dropwise. The mixture was stirred at room temperature for 1 hour. All solvents were removed and the residue was purified by preparative HPLC to give compounds 0021-0024.

LC-MS Condition

| LC Condition | |
|---|---|
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water - Methanol- TFA |
| Column | PHENOMENEX-LUNA 3.0 × 50 mm S10 |

| Compd. Number | Structure | MS (M + H)+ Calcd. | MS (M + H)+ Observ. | Rt (min) |
|---|---|---|---|---|
| 0021 | 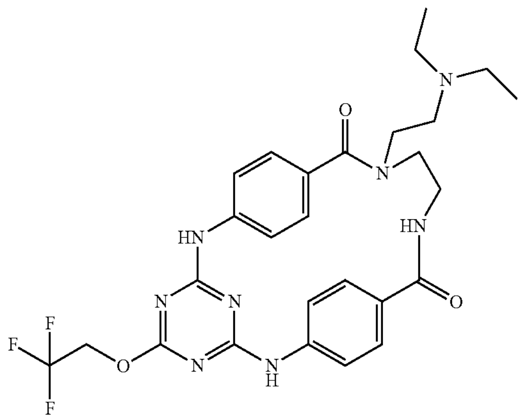 [SMILES: CCN(CC)CCN1CCNC(=O)c2ccc(cc2)Nc2nc(nc(OCC(F)(F)F)n2)Nc2ccc(cc2)C1=O] | 573.2 | 573.2 | 2.21 |
| 0022 | 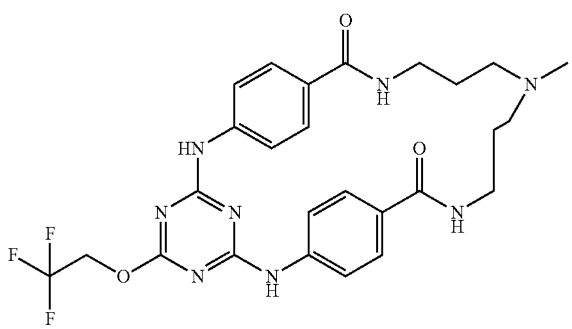 [SMILES: CN1CCCNC(=O)c2ccc(cc2)Nc2nc(nc(OCC(F)(F)F)n2)Nc2ccc(cc2)C(=O)NCCC1] | 559.2 | 559.2 | 2.29 |
| 0023 | 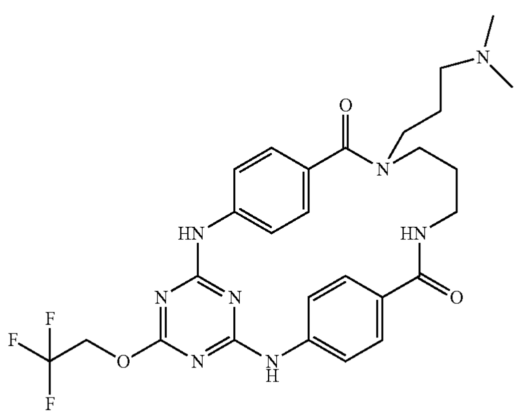 [SMILES: CN(C)CCCN1CCCNC(=O)c2ccc(cc2)Nc2nc(nc(OCC(F)(F)F)n2)Nc2ccc(cc2)C1=O] | 573.2 | 573.2 | 1.91 |

| Compd. Number | Structure | MS (M + H)+ Calcd. | MS (M + H)+ Observ. | Rt (min) |
|---|---|---|---|---|
| 0024 | 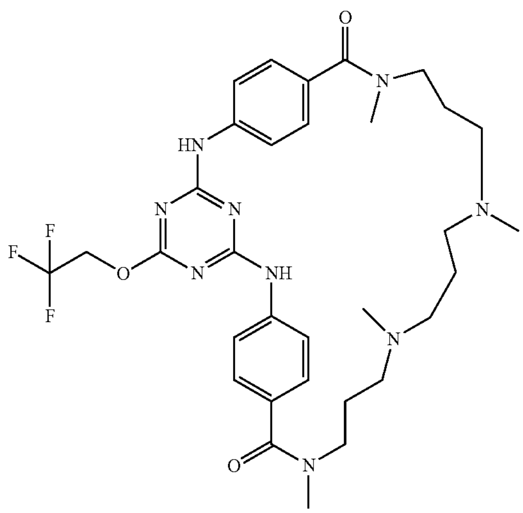 [SMILES: CN1CCCN(C)CCCN(C)C(=O)c2ccc(cc2)Nc2nc(nc(OCC(F)(F)F)n2)Nc2ccc(cc2)C(=O)N(C)CCC1] | 658.3 | 658.3 | 2.00 |
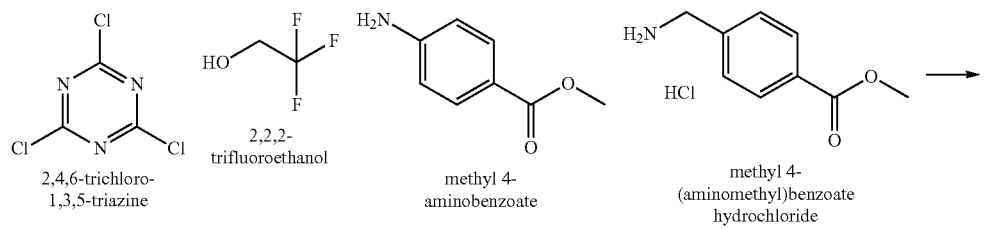
Synthesis Compounds 0031-0042:
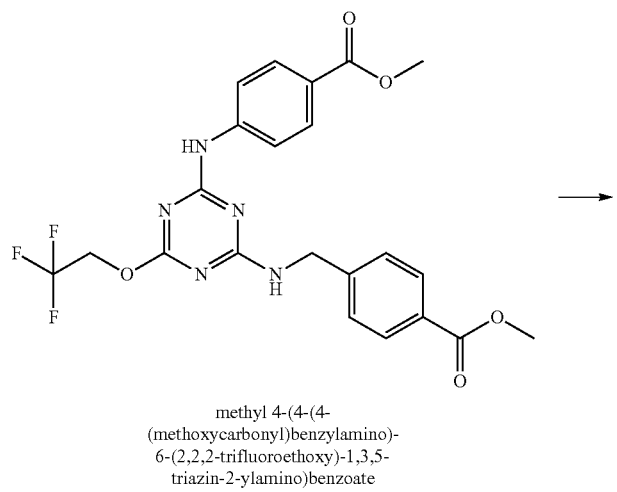
methyl 4-(4-(4-(methoxycarbonyl)benzylamino)-6-(2,2,2-trifluoroethoxy)-1,3,5-triazin-2-ylamino)benzoate

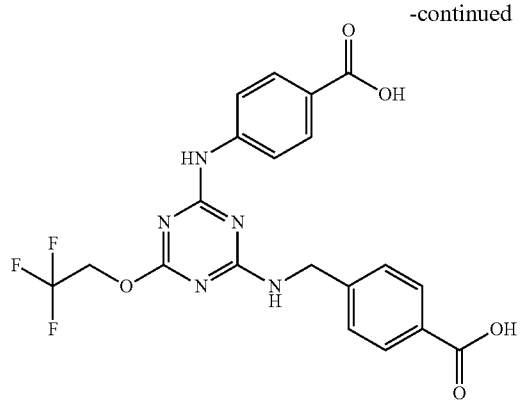

4-(4-(4-(carboxybenzylamino)-
6-(2,2,2-trifluoroethoxy)-1,3,5-
triazin-2-ylamino)benzoic acid

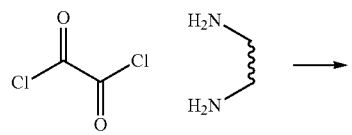

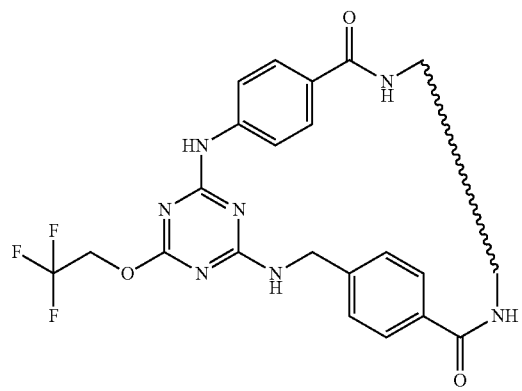

Compound 0031-0043

Step 1: To a solution of 2,4,6-trichloro-1,3,5-triazine (3 g) in acetone (70 mL) was added 2,2,2-trifluoroethanol (1.79 g) and 2,4,6-collidine (2.365 mL) in acetone (70.0 mL) dropwise over 1 hour. The resulting mixture was stirred at room temperature for 16 hours. All solvents were removed under vacuum to give a residue which was diluted with NMP (25 mL) and combined with methyl 4-aminobenzoate (2.71 g) and iPr$_2$NEt (8.52 mL). After stirring at room temperature for 6 hours, methyl 4-(aminomethyl)benzoate hydrochloride (3.28 g) was added and the resulting mixture was stirred at room temperature for 16 hours. The mixture was diluted with water (300 mL) and extracted with EtOAc (2×400 mL). The organic layers were combined, washed with water (200 mL), brine (300 mL), dried over MgSO$_4$ and concentrated. The residue was purified by recrystallization with MeOH to give methyl 4-(4-(4-(methoxycarbonyl)benzylamino)-6-(2,2,2-trifluoroethoxy)-1,3,5-triazin-2-ylamino)benzoate (5 g).

| methyl 4-(4-(4-(methoxycarbonyl)benzylamino)-6-(2,2,2-trifluoroethoxy)-1,3,5-triazin-2-ylamino)benzoate | |
|---|---|
| MS (M + H)$^+$ Calcd. | 492.1 |
| MS (M + H)$^+$ Observ. | 492.2 |
| Retention Time | 1.76 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Step 2: A mixture of methyl 4-(4-(4-(methoxycarbonyl) benzylamino)-6-(2,2,2-trifluoroethoxy)-1,3,5-triazin-2-ylamino)benzoate (2.9 g) and K$_2$CO$_3$ (3.26 g) in acetone (20 mL)/water (20.00 mL) was heated at 115° C. for 24 hours. After cooling to room temperature, the mixture was acidified with 1 N HCl to pH=3. The white precipitate was collected, washed with water and dried under vacuum to give 4-(4-(4-carboxybenzylamino)-6-(2,2,2-trifluoroethoxy)-1,3,5-triazin-2-ylamino)benzoic acid (2.6 g).

| 4-(4-(4-carboxybenzylamino)-6-(2,2,2-trifluoroethoxy)-1,3,5-triazin-2-ylamino)benzoic acid | |
|---|---|
| MS (M + H)+ Calcd. | 464.1 |
| MS (M + H)+ Observ. | 464.2 |
| Retention Time | 1.09 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Step 3: To a solution of 4-(4-(4-carboxybenzylamino)-6-(2,2,2-trifluoroethoxy)-1,3,5-triazin-2-ylamino)benzoic acid (1 eq.) in $CH_2Cl_2$ (30 mL) was added oxalyl dichloride (2 eq.) and a drop of DMF. After stirring for 1 hour, a solution of diamine (1 eq.) and $iPr_2NEt$ (3 eq.) in $CH_2Cl_2$ (5 mL) was added dropwise. The resulting solution was stirred at room temperature for 16 hours. All solvents were removed under vacuum and the residue was purified by preparative HPLC to give compounds 0031-0043.

| Compound 0031 | |
|---|---|
| MS (M + H)+ Calcd. | 600.3 |
| MS (M + H)+ Observ. | 600.3 |
| Retention Time | 1.73 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

LC-MS Condition for Compounds 0032-0035:

Start % B=30, Final % B=95 over 13.00° minute gradient

Wavelength=220 nm

Flow Rate=1 mL/min

Solvent A=water

Solvent B=ACN; Modifier=10 mm Ammonium Acetate

Column. Cosmosil PYE 4.6×150 mm

| Compd. Number | Structure | LC Rt (min) | Calcd. Ms Ion | Obs. Ms Ion |
|---|---|---|---|---|
| 0032 | 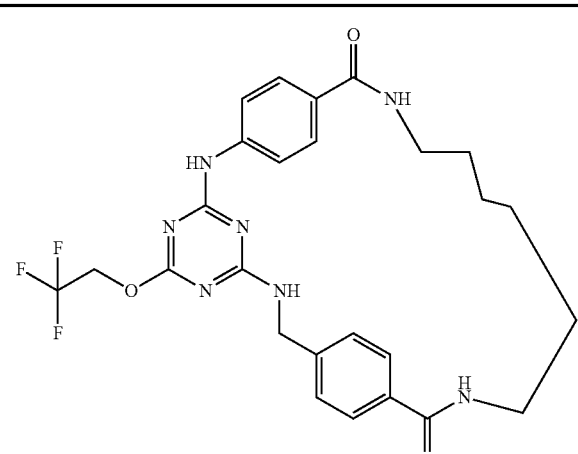 | 8.47 | 544.2 | 544.3 |

-continued
| Compd. Number | Structure | LC Rt (min) | Calcd. Ms Ion | Obs. Ms Ion |
|---|---|---|---|---|
| 0033 | 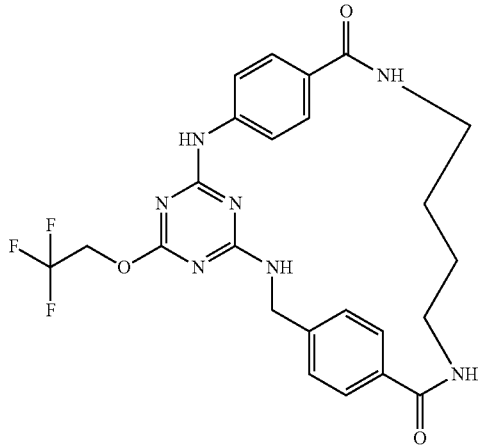 [SMILES: O=C1NCCCCNC(=O)c2ccc(cc2)Nc2nc(nc(OCC(F)(F)F)n2)NCc2ccc1cc2] | 5.08 | 516.2 | 516.2 |
| 0034 | 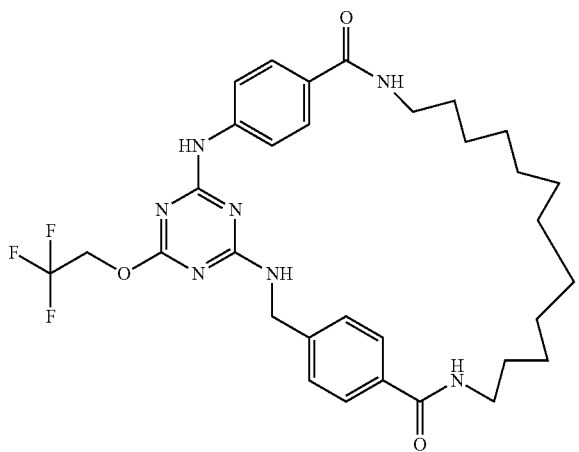 [SMILES: O=C1NCCCCCCCCCCCCNC(=O)c2ccc(cc2)Nc2nc(nc(OCC(F)(F)F)n2)NCc2ccc1cc2] | 9.54 | 628.3 | 628.5 |
| 0035 | 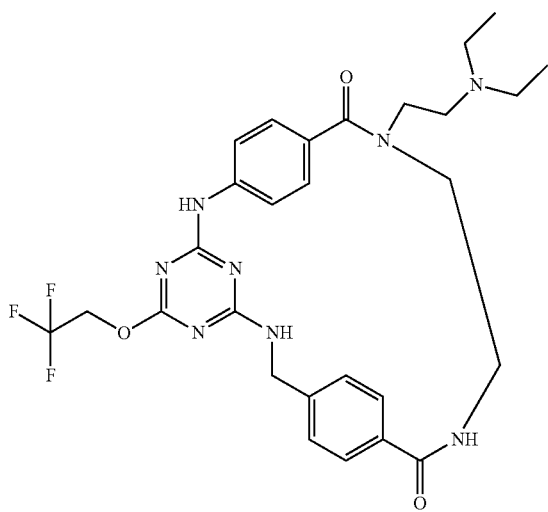 [SMILES: CCN(CC)CCN1CCNC(=O)c2ccc(cc2)CNc2nc(nc(OCC(F)(F)F)n2)Nc2ccc(cc2)C1=O] | 3.74 | 587.3 | 587.5 |

LC-MS Condition for Compounds 0036-0042:
  Start % B=10, Final % B=95 over 8.30° minute gradient
  Wavelength=220 nm
  Solvent A=water
  Solvent B=ACN; Modifier=10 mm Ammonium Acetate
  Flow Rate=1 mL/min
  Column: Waters Xbridge 4.6×100 mm 5 um C18
| Compd. Number | Structure | LC Rt (min) | Calcd. Ms Ion | Obs. Ms Ion |
|---|---|---|---|---|
| 0036 | 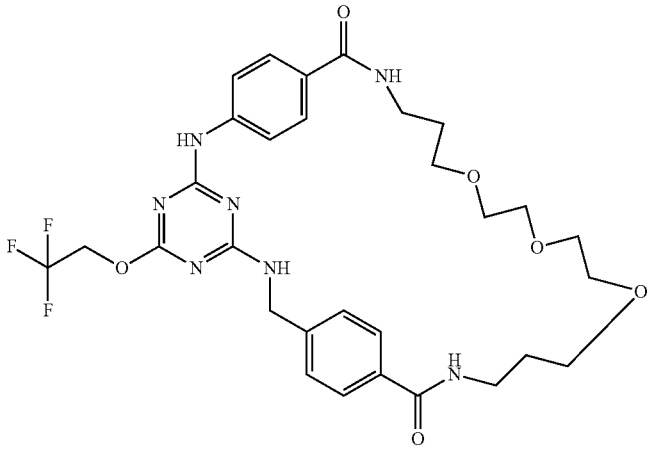 [SMILES: O=C1NCCCOCCOCCOCCCNC(=O)c2ccc(cc2)Nc2nc(nc(OCC(F)(F)F)n2)NCc2ccc1cc2] | 4.27 | 648.3 | 648.4 |
| 0037 | 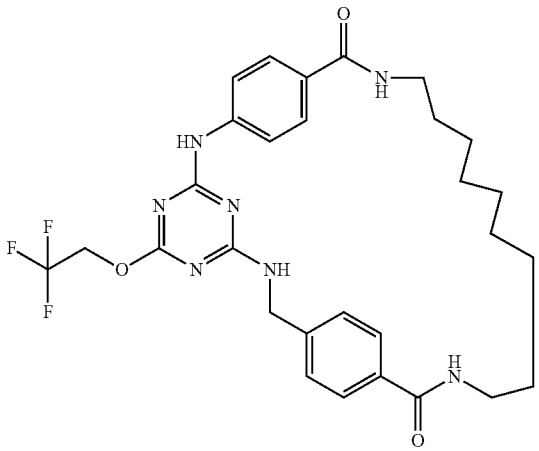 [SMILES: O=C1NCCCCCCCCCNC(=O)c2ccc(cc2)Nc2nc(nc(OCC(F)(F)F)n2)NCc2ccc1cc2] | 5.25 | 586.3 | 586.4 |
| 0038 | 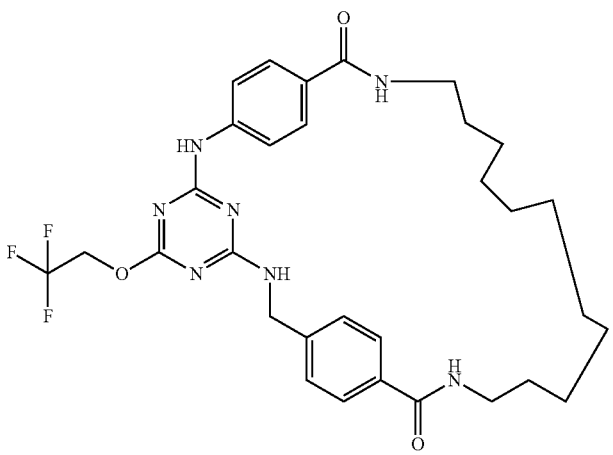 [SMILES: O=C1NCCCCCCCCCCCNC(=O)c2ccc(cc2)Nc2nc(nc(OCC(F)(F)F)n2)NCc2ccc1cc2] | 5.81 | 614.3 | 614.5 |

-continued

| Compd. Number | Structure | LC Rt (min) | Calcd. Ms Ion | Obs. Ms Ion |
|---|---|---|---|---|
| 0039 | 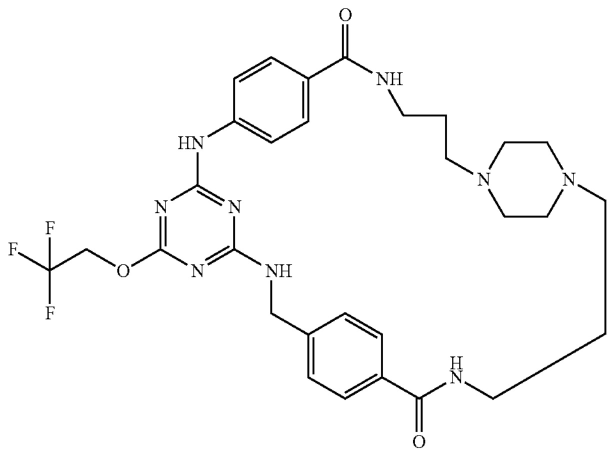 [SMILES: O=C1NCCCN2CCN(CCCNC(=O)c3ccc(cc3)Nc3nc(nc(OCC(F)(F)F)n3)NCc3ccc1cc3)CC2] | 3.65 | 628.3 | 628.5 |
| 0041 | 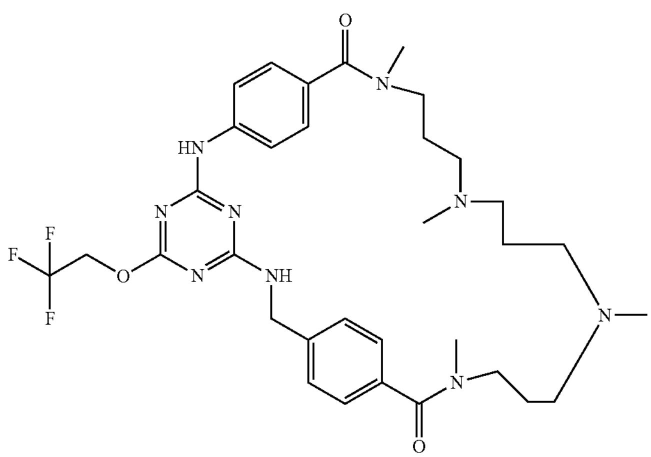 [SMILES: CN1CCCN(C)CCCN(C)C(=O)c2ccc(cc2)Nc2nc(nc(OCC(F)(F)F)n2)NCc2ccc(cc2)C(=O)N(C)CCC1] | 3.68 | 672.4 | 672.6 |
| 0042 | 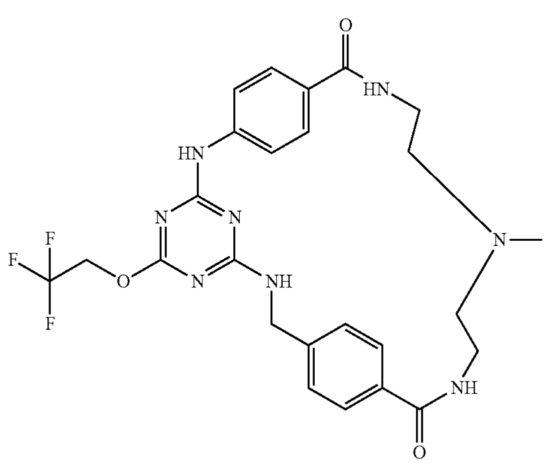 [SMILES: CN1CCNC(=O)c2ccc(cc2)CNc2nc(nc(OCC(F)(F)F)n2)Nc2ccc(cc2)C(=O)NCC1] | 4.20 | 545.2 | 545.3 |

Syntheses of Compounds 0051-0072:

Step 1 to Step 4: Preparation of Intermediates N2-(3-(aminomethyl)benzyl)-N4-(4-(aminomethyl)phenyl)-6-(2,2,2-trifluoroethoxy)-1,3,5-triazine-2,4-diamine and N2-(4-(aminomethyl)benzyl)-N4-(4-(aminomethyl)phenyl)-6-(2,2,2-trifluoroethoxy)-1,3,5-triazine-2,4-diamine:

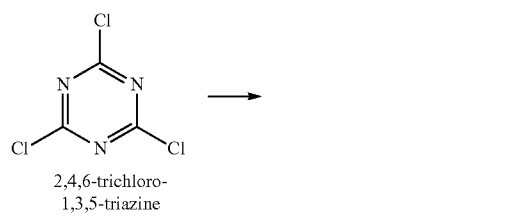

2,4,6-trichloro-1,3,5-triazine

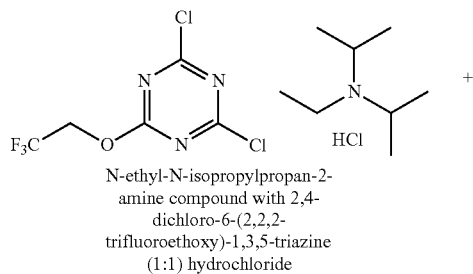

N-ethyl-N-isopropylpropan-2-amine compound with 2,4-dichloro-6-(2,2,2-trifluoroethoxy)-1,3,5-triazine (1:1) hydrochloride

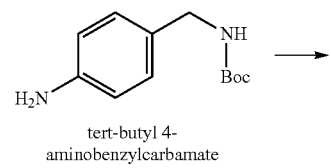

tert-butyl 4-aminobenzylcarbamate

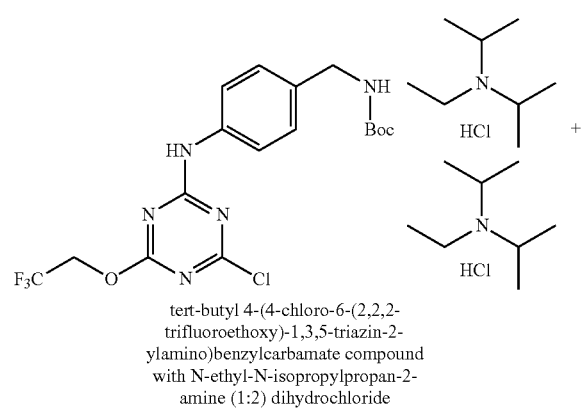

tert-butyl 4-(4-chloro-6-(2,2,2-trifluoroethoxy)-1,3,5-triazin-2-ylamino)benzylcarbamate compound with N-ethyl-N-isopropylpropan-2-amine (1:2) dihydrochloride

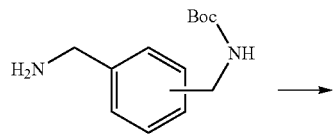

Meta derivative: tert-butyl 3-(aminomethyl)benzylcarbamate
Para derivative: tert-butyl 4-(aminomethyl)benzylcarbamate

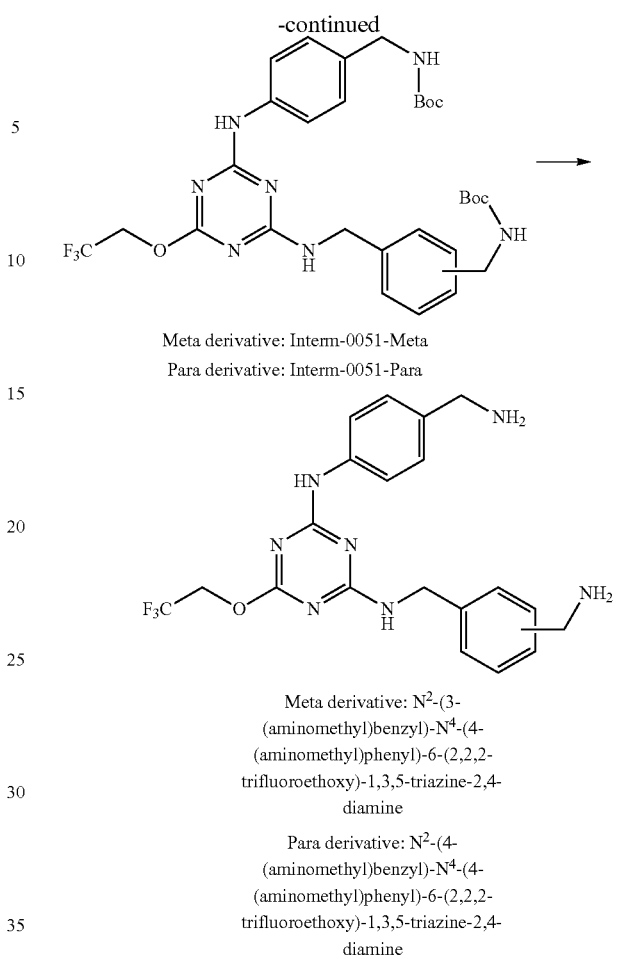

Meta derivative: Interm-0051-Meta
Para derivative: Interm-0051-Para

Meta derivative: $N^2$-(3-(aminomethyl)benzyl)-$N^4$-(4-(aminomethyl)phenyl)-6-(2,2,2-trifluoroethoxy)-1,3,5-triazine-2,4-diamine Para derivative: $N^2$-(4-(aminomethyl)benzyl)-$N^4$-(4-(aminomethyl)phenyl)-6-(2,2,2-trifluoroethoxy)-1,3,5-triazine-2,4-diamine Step 1: To a soln. of 2,4,6-trichloro-1,3,5-triazine (3.32 g) in THF (100 mL) was added a mixture of 2,2,2-trifluoroethanol (1.8 g) and iPr$_2$NEt (10 mL) at room temperature. The resulting mixture was stirred at room temperature for 24 hours.

Step 2: To above mixture was added tert-butyl 4-aminobenzylcarbamate (4 g) and iPr$_2$NEt. The mixture was then stirred for 24 hours to show formation of the desired product. After removal of solvents, the crude tert-butyl 4-(4-chloro-6-(2,2,2-trifluoroethoxy)-1,3,5-triazin-2-ylamino)benzylcarbamate compound with N-ethyl-N-isopropylpropan-2-amine (1:2) dihydrochloride was used in the further step without purification.

Step 3: iPr$_2$NEt was added into the solution of tert-butyl 4-(4-chloro-6-(2,2,2-trifluoroethoxy)-1,3,5-triazin-2-ylamino)benzylcarbamate compound with N-ethyl-N-isopropylpropan-2-amine (1:2) dihydrochloride (5 g) and 1.54 g of tert-butyl 3-(aminomethyl)benzylcarbamate or tert-butyl 4-(aminomethyl)benzylcarbamate in THF (100 mL). The reaction was stirred at room temperature for 16 hours before being quenched with water (100 mL). The aqueous layer was extracted with EtOAc (3×100 mL). The combined organic phase was dried over MgSO$_4$ and concentrated to give the desired product which was purified by silica gel chromatography.

| Meta derivative: Interm-0051-Meta | |
|---|---|
| MS (M + H)+ Calcd. | 634.3 |
| MS (M + H)+ Observ. | 634.4 |
| Retention Time | 2.08 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

| Meta derivative: Interm-0051-Para | |
|---|---|
| MS (M + H)+ Calcd. | 634.3 |
| MS (M + H)+ Observ. | 634.4 |
| Retention Time | 2.07 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 4: To Interm-0051-Meta or Interm-0051-Para (0.38 g) in a 16×100 mm Wheaton vial was added TFA (3 mL). Vial was capped and agitated at 350 rpm on an Innova platform shaker at room temperature for 18 hours. Solvents were blown away in the Zymark tabletop dryer at 40° C. for 3 hours. After being dried under reduced pressure, the residue was used in the further reactions without purification.

Step 5: General Procedure for Preparation of Cyclic Di-Ureas

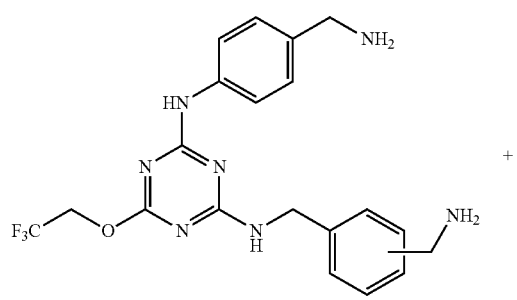

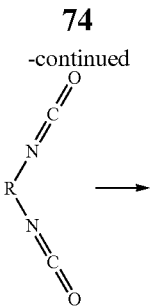

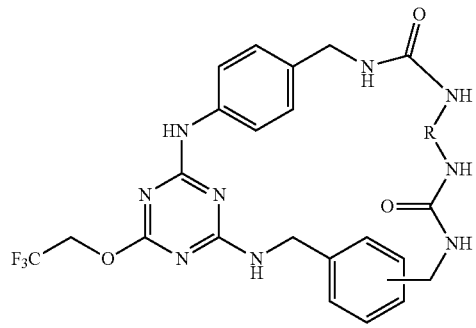

Stock solutions of the diamine cores (173 mg, 400 µmol each) in DMF (8.0 mL each) were prepared. To each of these stock solutions was added iPr$_2$NEt (352 µL, 2.0 mmol). To each of the isocyanates (pre-weighed into 16×100 mm Wheaton vials) was added 2 mL of dichloroethane. 1 mL of each of these solutions was transferred to separate Wheaton vials and 4 mL of dichloroethane was added to each of these solutions. To each of the vials containing the isocyanates was added the 1 mL of the appropriate diamine solution. Vials were capped and agitated at 350 rpm on an Innova platform shaker at room temperature for 18 hours. Samples were blown down in the Zymark tabletop dryer at 40° C. for 3 hours, before 1 mL of DMF was added to each vial. Suspend contents were vortexed well and suspensions were applied to 6-mL silica SPE cartridges, eluted w/4 mL of MeOH each, collected into 16×100 mm culture tubes. Samples were blown down in the Zymark tabletop dryer at 40° C. for 3 hours. Then, 1 mL of DMF was added into each vial. Contents were transferred to 96 well deep-well plate, filtered w/0.45 µm syringe filters. Reaction vials were rinsed and transferred w/filtering. 25 µL of solution was removed from each well and diluted w/225 µL of DMF for LC/MS analysis. Purification via preparative HPLC offered products.

Initial Analysis:

WFD-446-LCMS2:

MassLynx 4.0 SP4 LC-MS software

CTC-Leap HTS-PAL autosampler

Agilent 1100 quaternary pump

Agilent 1100 photodiode array

Polymer Lab 2100 ELS detector (Evap. Temp.=45° C., Neb. Temp.=35° C.)

Waters ZQ mass spectrometer

Column-Waters Xbridge 4.6×50 mm 5 um C18

Mobile Phase-A=5:95 Acetonitrile or MeOH:Water; B=95:5

Acetonitrile or MeOH:Water; Modifier=10 mM NH$_4$OAc

Method
WFD-LCMS-003 MeOH (4.6×50 mm, 5 um, 9 min):

| Time | B % | Flow |
|---|---|---|
| 0.00' | 0 | 2.0 |
| 8.00' | 100 | 2.0 |
| 9.00' | 100 | 2.0 |
| 9.10' | 0 | 2.0 |
| 10.00' | 0 | 2.0 |

Preparative HPLC
WFD-445-PMS1 (Waters):
Masslynx 4.0 SP2
Waters 2767 Sample Manager (autosampler/fraction collector)
Waters Column Fluidics Organizer
Waters 2525 binary pump
Waters 515 pumps for Makeup, At-Column-Dilution, and Dial-A-Mix
flows (resp.)
Waters 2787 UV detector
Waters ZQ with ESCi mass spectrometer
Column-a) Waters Xbridge 19×200 mm 5 um C18 or b) Waters
Xbridge 19×200 mm 5 um Shield RP-18
Guard Column-Waters Xbridge 19×10 mm 5 um C18
Mobile Phase-A=Water; B=95:5 Acetonitrile; Water; Modifier=20 mM $NH_4OAc$ Method
WFD-PMS1-Nwx14aA (19×200 mm): for B=ACN
25 mL/min, 0'=20% B, 0.5' (12.5 mL/min)=20% B, 2' (12.5 mL/min)=20% B, 2.5°=20% B, 23'=95% B, 30'=95% B
Sample Drying-GeneVac Program HT-24-ACN-$H_2O$-Buffer in 16×100 TT & AL blocks: Temp=45 C, 0.3 h@175 to 40 bar, 1.7 h@40 bar, defrost, 6 h@8 bar, 6 h@Full Vac, defrost.
Final Analysis
WFD-446-LCMS2:
MassLynx 4.0 SP4 LC-MS software
CTC-Leap HTS-PAL autosampler
Agilent 1100 binary pump
Agilent 1100 photodiode array (220 nm)
Polymer Lab 2100 ELS detector (Evap. Temp.=45° C., Neb. Temp.=35° C.)
Waters ZQ mass spectrometer
Column-Supelco Ascentis Express 4.6×50 mm 2.7 um C18
Mobile Phase-A=5:95 ACN:Water; B=95:5 ACN:Water; Modifier=10 mM $NH_4OAc$
Method
WFD-MUX-004 (4.6×50 mm):

| Time | B % | Flow |
|---|---|---|
| 0.00' | 0 | 2.0 |
| 8.00' | 100 | 2.0 |
| 9.00' | 100 | 2.0 |
| 9.10' | 100 | 2.0 |
| 10.00' | 0 | 2.0 |

| Cpd. | Structure | HPLC Rt | Calcd. Ms Ion | Obs. Ms Ion | Prep Column |
|---|---|---|---|---|---|
| 0051 | 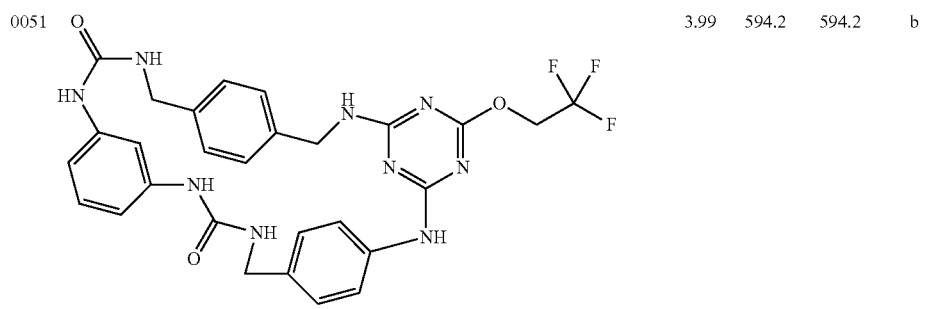 | 3.99 | 594.2 | 594.2 | b |
| 0052 | 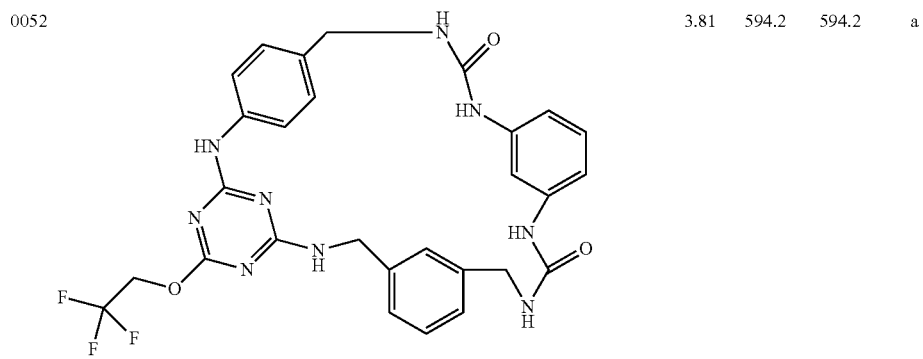 | 3.81 | 594.2 | 594.2 | a |

| Cpd. | Structure | HPLC Rt | Calcd. Ms Ion | Obs. Ms Ion | Prep Column |
|---|---|---|---|---|---|
| 0053 | 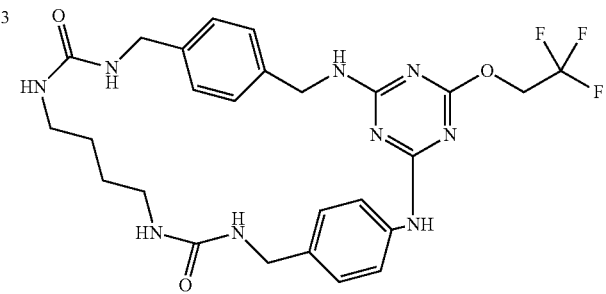 | 3.53 | 574.3 | 574.3 | a |
| 0054 | 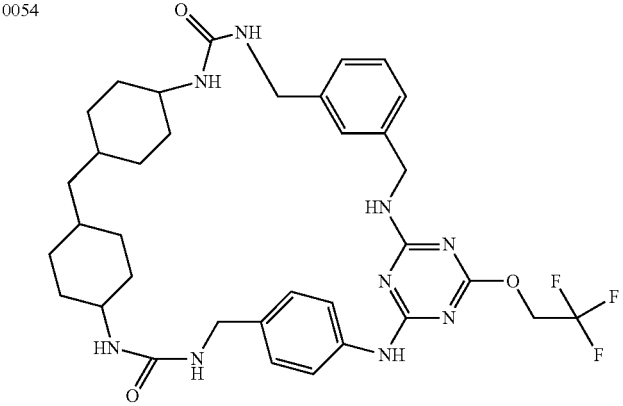 | 4.34 | 696.4 | 696.4 | a |
| 0055 | 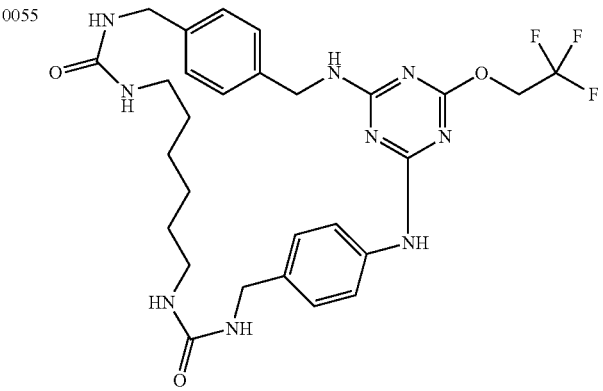 | 3.85 | 602.3 | 602.3 | b |

| Cpd. | Structure | HPLC Rt | Calcd. Ms Ion | Obs. Ms Ion | Prep Column |
|---|---|---|---|---|---|
| 0056 | 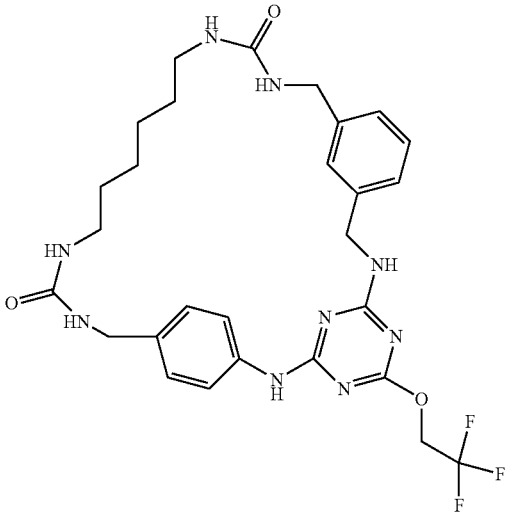 [SMILES: O=C1NCCCCCCNC(=O)NCc2cccc(c2)CNc2nc(nc(OCC(F)(F)F)n2)Nc2ccc(cc2)CN1] | 3.81 | 602.3 | 602.3 | b |
| 0057 | 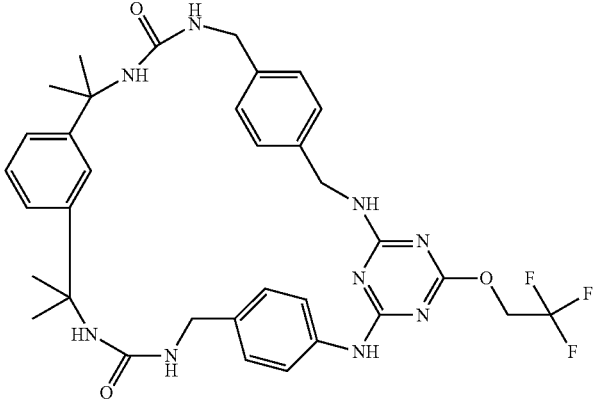 [SMILES: CC1(C)NC(=O)NCc2ccc(cc2)CNc2nc(nc(OCC(F)(F)F)n2)Nc2ccc(cc2)CNC(=O)NC(C)(C)c2cccc1c2] | 4.56 | 678.3 | 678.3 | a |
| 0058 | 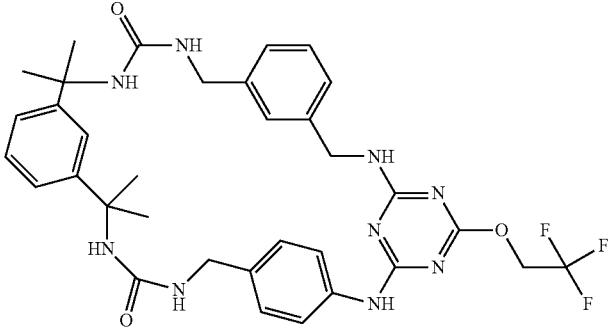 [SMILES: CC1(C)NC(=O)NCc2ccc(cc2)Nc2nc(nc(OCC(F)(F)F)n2)NCc2cccc(c2)CNC(=O)NC(C)(C)c2cccc1c2] | 4.42 | 678.3 | 678.3 | b |

Step 5: General Procedure for Preparation of Cyclic Di-Amides

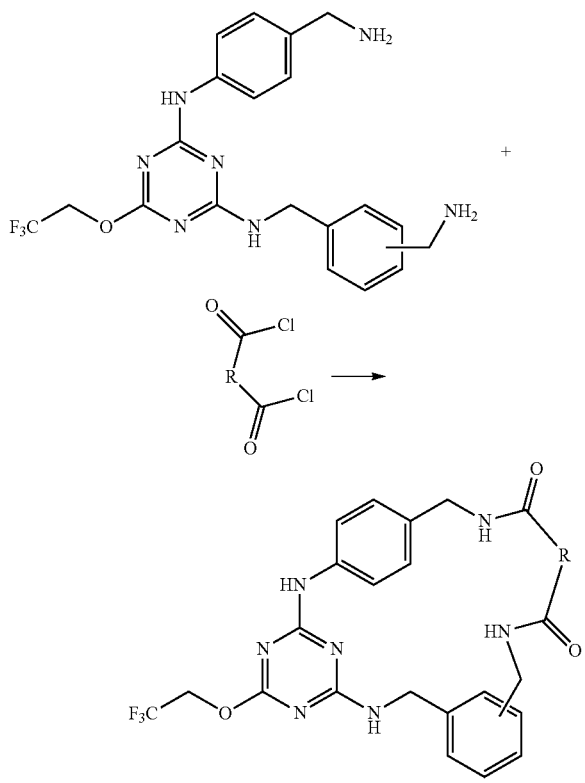

Stock solutions of the diamine cores (173 mg, 400 μmol each) in DMF were prepared (8.0 mL each). To each of these stock solutions was added iPr$_2$NEt (528 μL, 3.0 mmol). To each of the acid chlorides (pre-weighed into 16×100 mm Wheaton vials) was added 2 mL of dichloroethane. 1 ml of each of these solutions was transferred to separate Wheaton vials. And 5 mL of dichloroethane was added to each of these solutions. To each of the vials containing the isocyanates was added the 1 mL of the appropriate diamine solution. Vials were capped and agitated at 350 rpm on an Innova platform shaker at room temperature for 18 hours. Samples were blown down in the Zymark tabletop dryer at 40° C. for 2 hours, before addition of 750 μL of DMF to each sample. Contents were transferred to a 96 well filter plate, collected into a 96 well deep-well plate. Reaction vials were rinsed w/250 μL of DMF and transferred rinses to the filter plate. 25 μL of solution was removed from each well and diluted to 325 μL for LC/MS analysis. Purification via preparative HPLC offered products.

Initial Analysis:
  WFD-446-HPLC4:
  MassLynx 4.1
  Waters 2777 Sample Manager (CTC MXY01-01B)
  Waters Acquity Binary HPLC pump
  Waters Acquity TUV detector (220 nm)
  Waters SD mass spectrometer with ESI probe
  Column-Waters Xbridge 2.1×50 mm 1.7 um C18 (BEH-C18 for HPLC)
  Mobile Phase-A=5:95 SS:Water; B=95:5 SS:Water; Modifier=10 mM NH$_4$OAc Methods
WFD-HPLC-001 MeOH (2×50 mm, 1.7 um, 5 min):

| Time | B % | Flow |
| --- | --- | --- |
| 0.00' | 0 | 0.5 |
| 4.00' | 100 | 0.5 |
| 5.00' | 100 | 0.5 |
| 5.10' | 0 | 0.5 |
| 5.50' | 0 | 0.5 |

WFD-HPLC-002 ACN (2×50 mm, 1.7 um, 5 min):

| Time | B % | Flow |
| --- | --- | --- |
| 0.00' | 0 | 0.83 |
| 4.00' | 100 | 0.83 |
| 5.00' | 100 | 0.83 |
| 5.10' | 0 | 0.83 |
| 5.50' | 0 | 0.83 |

Preparative HPLC
  WFD-445-PMS3 (Dionex APS-3000):
  Chromeleon 6.70 spl LC software
  Dionex P680 binary pump for analytical
  Dionex PP 150 binary pump prep
  Dionex UVD340U UV spectrometer (220 nm)
  Sedex 75 ELS detector
  Thermo-Finnigen MSQ Surveyor Plus mass spectrometer
  Column-Waters Xbridge 19×150 mm 5 um C18
  Guard Column-Waters Xbridge 19×10 mm 5 um C18
  Mobile Phase-A=Water; B=95:5 Acetonitrile; Water; Modifier=20 mM NH$_4$OAc
Method
  WFD-PMS3_Methanol (19×150 mm): 30 mL/min, 0'=40% B, 0.5° (10 mL/min)=40% B, 2' (10 mL/min)=40% B, 2.5° (20 mL/min)=30% B, 20'=95% B, 20'=95% B
Sample Drying-GeneVac Program HT-24-ACN-H$_2$O-Buffer in 16×100 TT & AL blocks: Temp=45 C, 0.3 h@175 to 40 bar, 1.7 h@40 bar, defrost, 6 h@8 bar, 6 h@Full Vac, defrost.
Final Analysis
  WFD-446-LCMS2:
  MassLynx 4.0 SP4 LC-MS software
  CTC-Leap HTS-PAL autosampler
  Agilent 1100 binary pump
  Agilent 1100 photodiode array (220 nm)
  Polymer Lab 2100 ELS detector (Evap. Temp.=45° C., Neb. Temp.=35° C.)
  Waters ZQ mass spectrometer
  Column-Supelco Ascentis Express 4.6×50 mm 2.7 um C18
  Mobile Phase-A=5:95 ACN:Water; B=95:5 ACN:Water; Modifier=10 mM NH$_4$OAc
Method
  WFD-MUX-004 (4.6×50 mm):

| Time | B % | Flow |
| --- | --- | --- |
| 0.00' | 0 | 2.0 |
| 8.00' | 100 | 2.0 |
| 9.00' | 100 | 2.0 |
| 9.10' | 100 | 2.0 |
| 10.00' | 0 | 2.0 |

| Compd. Number | Structure | HPLC Rt | Calcd. Ms Ion | Observed Ms Ion |
|---|---|---|---|---|
| 0059 | 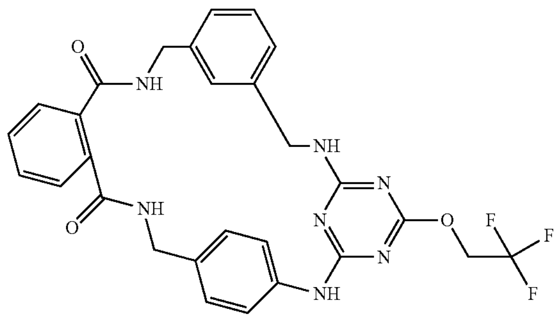 [SMILES: O=C1NCc2ccc(cc2)Nc2nc(nc(OCC(F)(F)F)n2)NCc2cccc(c2)CNC(=O)c2ccccc21] | 4.06 | 564.2 | 564.2 |
| 0060 | 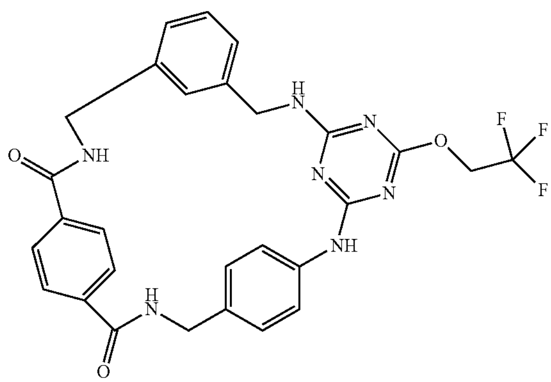 [SMILES: O=C1NCc2ccc(cc2)Nc2nc(nc(OCC(F)(F)F)n2)NCc2cccc(c2)CNC(=O)c2ccc1cc2] | 3.87 | 564.2 | 564.2 |
| 0061 | 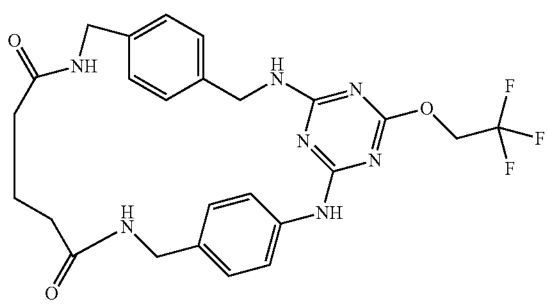 [SMILES: O=C1CCCC(=O)NCc2ccc(cc2)Nc2nc(nc(OCC(F)(F)F)n2)NCc2ccc(cc2)CN1] | 3.41 | 530.2 | 530.2 |
| 0062 | 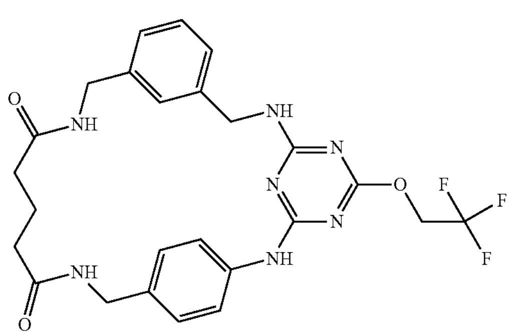 [SMILES: O=C1CCCC(=O)NCc2cccc(c2)CNc2nc(nc(OCC(F)(F)F)n2)Nc2ccc(cc2)CN1] | 3.47 | 530.2 | 530.2 |

-continued
| Compd. Number | Structure | HPLC Rt | Calcd. Ms Ion | Observed Ms Ion |
|---|---|---|---|---|
| 0063 | 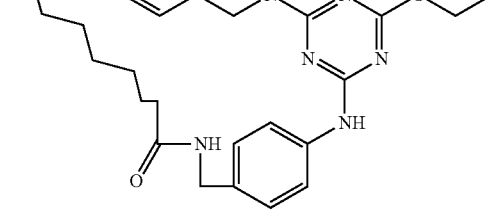 | 3.77 | 572.3 | 572.2 |
| 0064 | 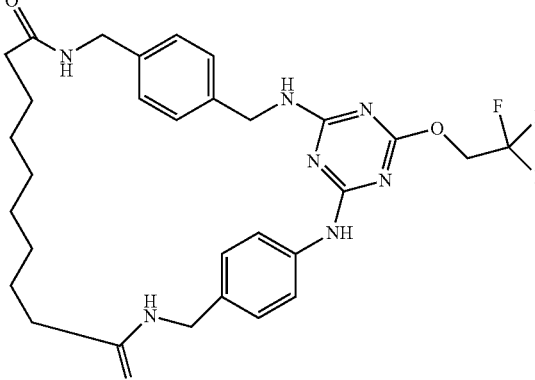 | 4.22 | 600.3 | 600.3 |
| 0065 | 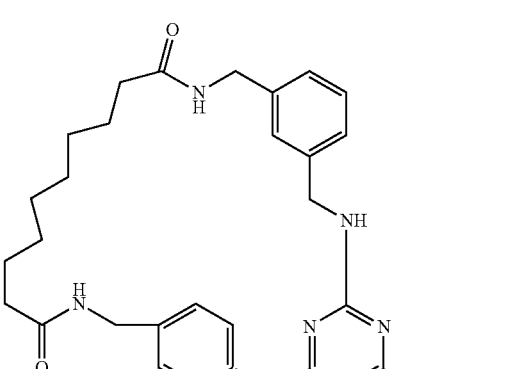 | 4.38 | 600.3 | 600.3 |

| Compd. Number | Structure | HPLC Rt | Calcd. Ms Ion | Observed Ms Ion |
|---|---|---|---|---|
| 0067 | 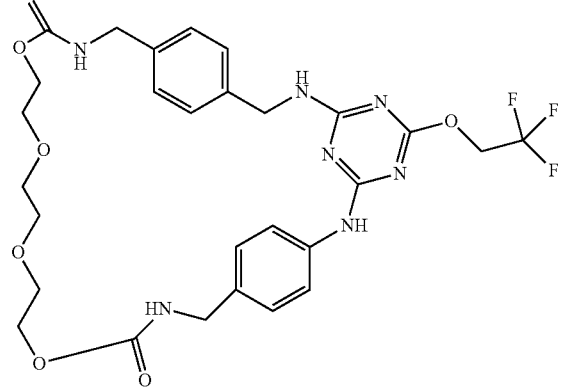 | 4.12 | 636.2 | 636.2 |
| 0068 | 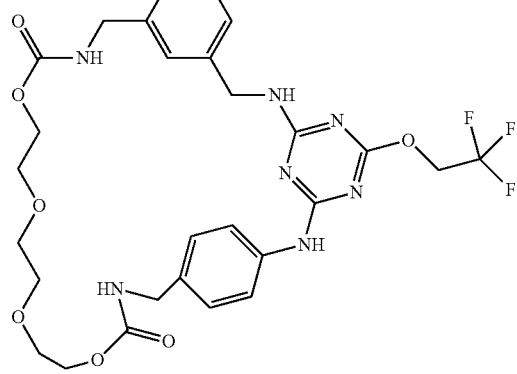 | 4.27 | 636.2 | 636.2 |
| 0069 | 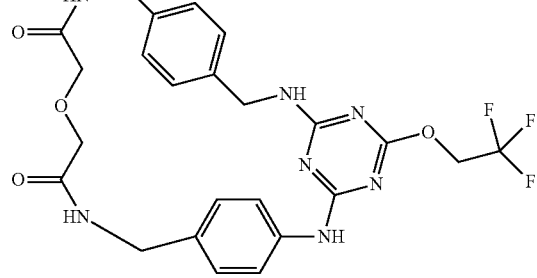 | 3.54 | 532.2 | 532.2 |
| 0070 | 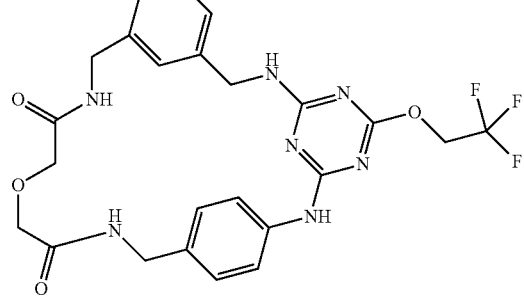 | 3.66 | 532.2 | 532.2 |

| Compd. Number | Structure | HPLC Rt | Calcd. Ms Ion | Observed Ms Ion |
|---|---|---|---|---|
| 0071 | 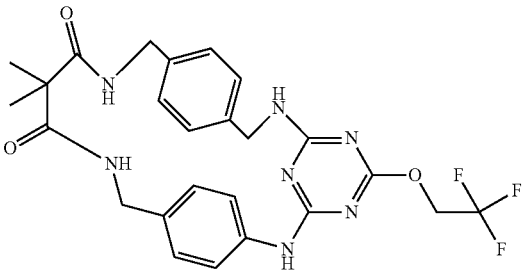 [SMILES: CC1(C)C(=O)NCc2ccc(cc2)CNc2nc(nc(OCC(F)(F)F)n2)Nc2ccc(cc2)CNC1=O] | 3.98 | 530.2 | 530.2 |
| 0072 | 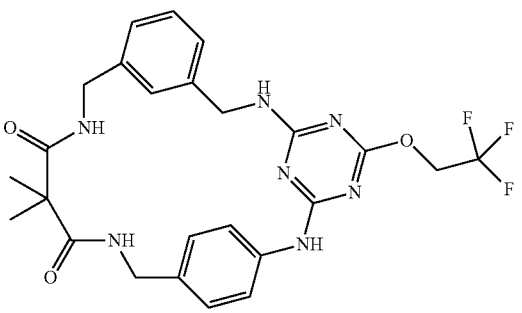 [SMILES: CC1(C)C(=O)NCc2ccc(cc2)Nc2nc(nc(OCC(F)(F)F)n2)NCc2cccc(c2)CNC1=O] | 4.1 | 530.2 | 530.2 |
The next section describes the synthesis of 2000 series compounds.
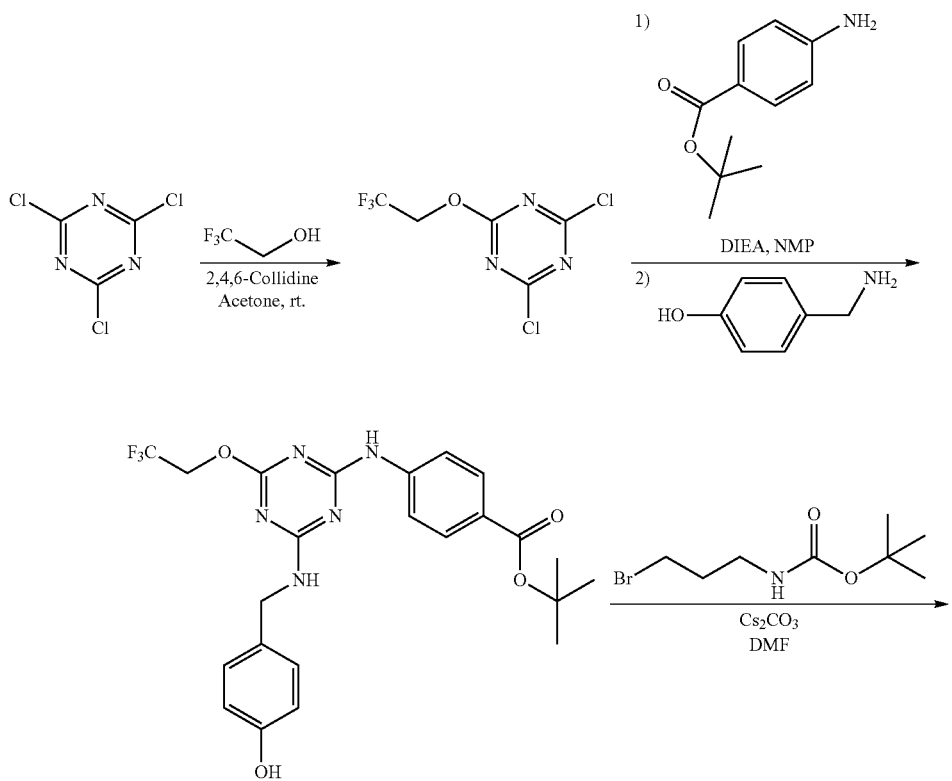

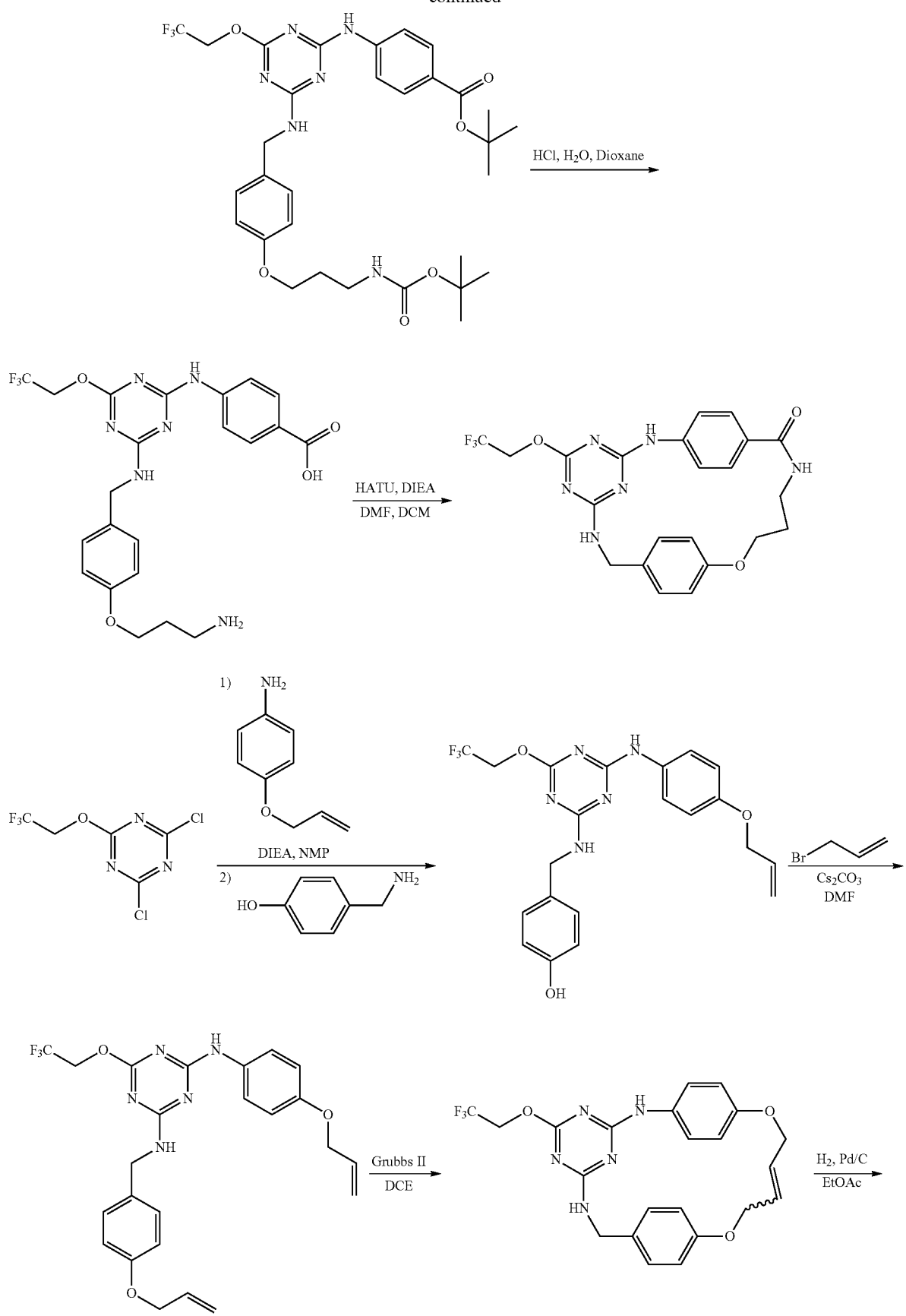

-continued
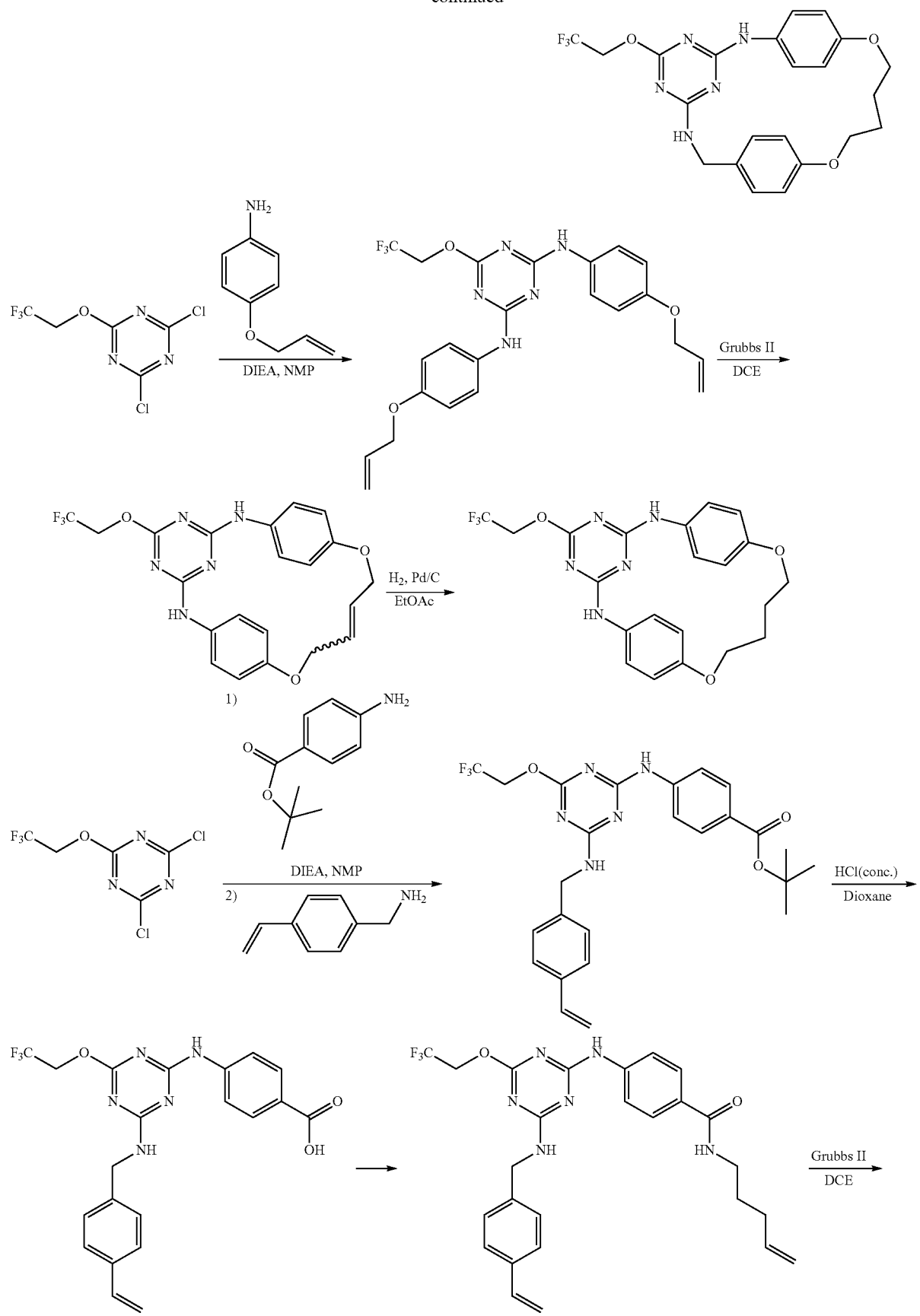

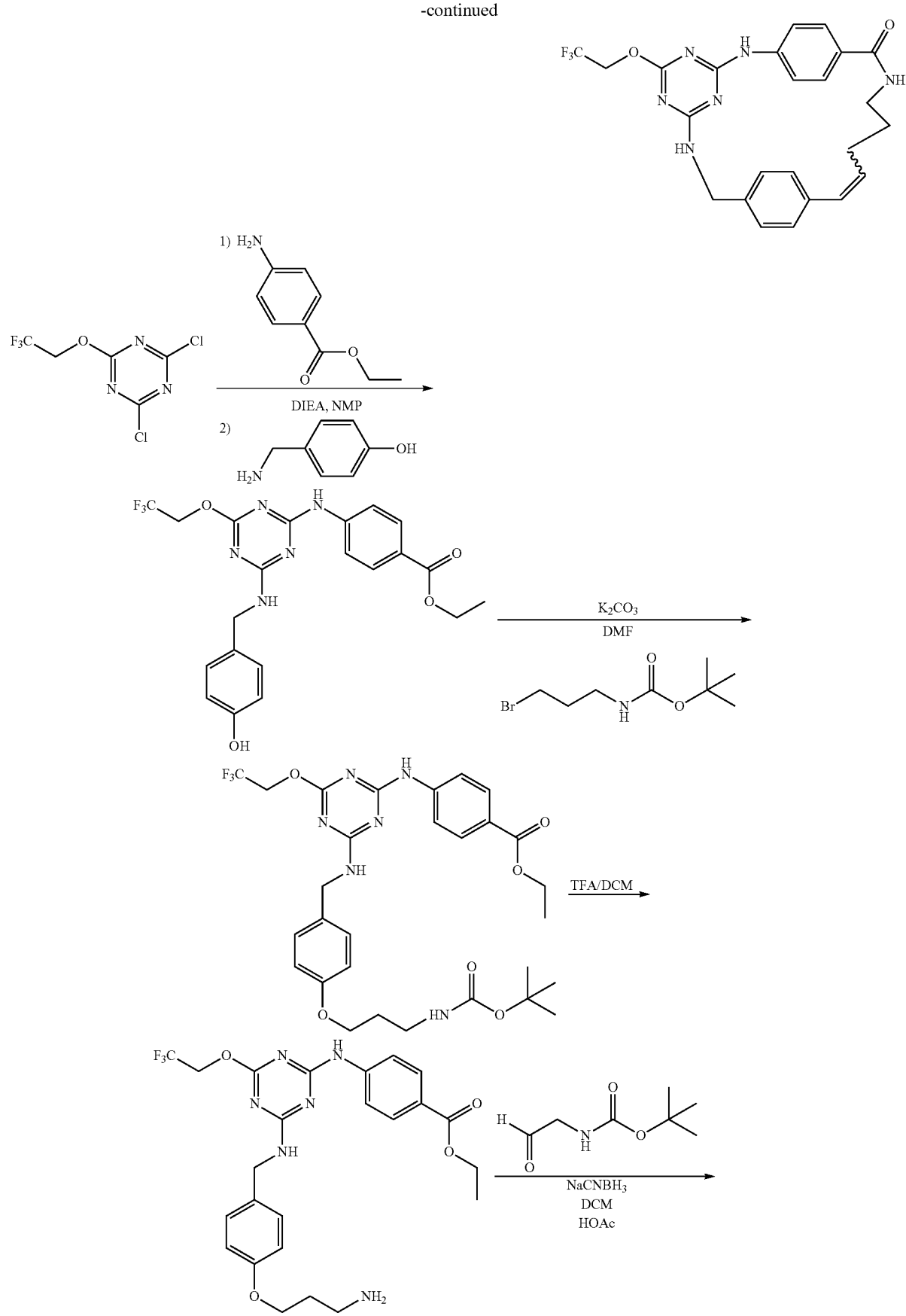

-continued

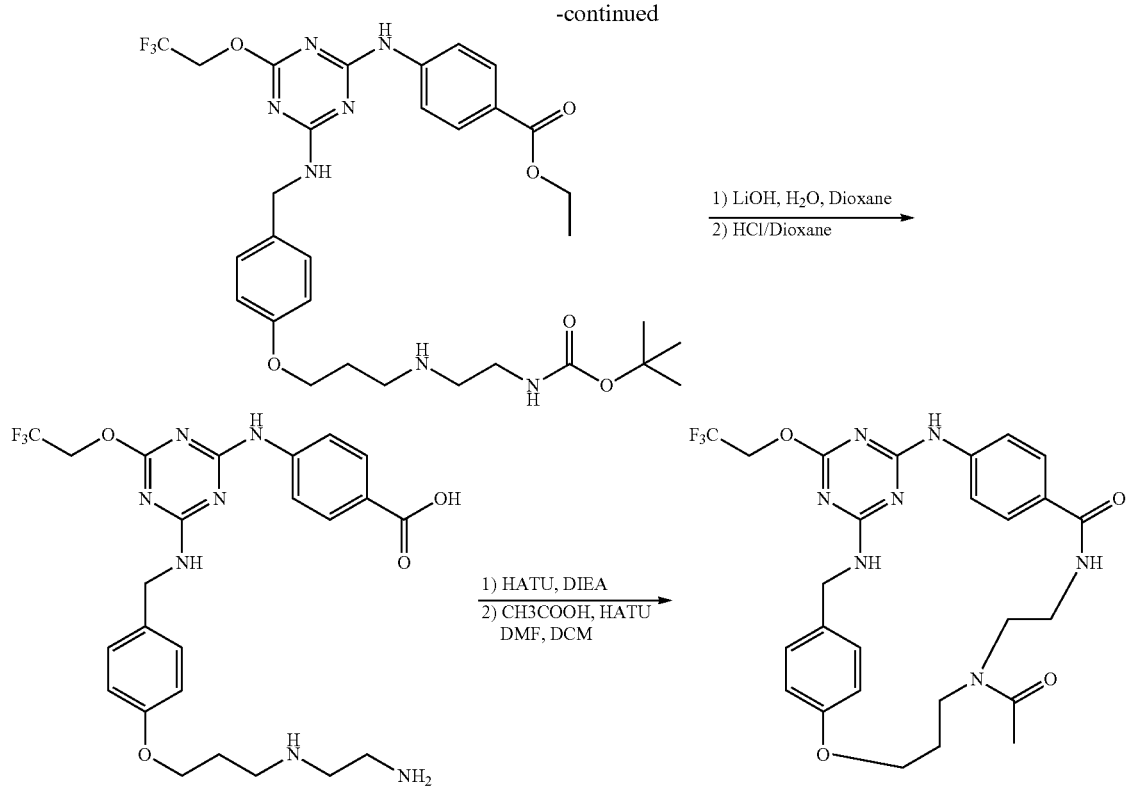

Intermediates

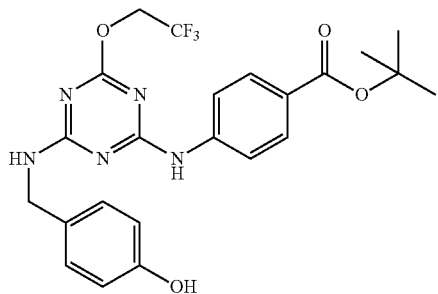 [SMILES: CC(C)(C)OC(=O)c1ccc(Nc2nc(NCc3ccc(O)cc3)nc(OCC(F)(F)F)n2)cc1]

tert-Butyl 4-(4-(4-hydroxybenzylamino)-6-(2,2,2-trifluoroethoxy)-1,3,5-triazin-2-ylamino)benzoate, TFA salt. To a 0.1 M solution of 2,4-dichloro-6-(2,2,2-trifluoroethoxy)-1,3,5-triazine in N-methylpyrrolidine (1 ml, 0.1 mmol) was added tert-butyl 4-aminobenzoate (19.3 mg, 0.100 mmol) and diisopropylethylamine (DIEA) (0.035, 0.2 mmol) at r.t. The resulted mixture was stirred at r.t. for 30 mins and the completion of the reaction was monitored by LC/MS. 4-(Aminomethyl)phenol, HCl salt (15.96 mg, 0.100 mmol) was added, followed by diisopropylethylamine (DIEA) (0.035, 0.2 mmol). The reaction mixture was stirred at r.t. for 16 hrs. The reaction mixture was purified by preparative HPLC to afford 21 mg (34.7%) of the title compound as TFA salt. $^1$H NMR (500 MHz, MeOD) δ ppm 1.61 (s, 9H), 4.56 (s, 2H), 4.89-4.92 (m, 2H), 6.78 (d, J=8.55 Hz, 2H), 7.04-7.37 (m, 2H), 7.71 (d, J=8.85 Hz, 2H), 7.88 (d, J=8.85 Hz, 2H).

| 35 | tert-Butyl 4-(4-(4-hydroxybenzylamino)-6-(2,2,2-trifluoroethoxy)-1,3,5-triazin-2-ylamino)benzoate, TFA salt. | |
|---|---|---|
| | MS (M + H)$^+$ Calcd. | 492 |
| | MS (M + H)$^+$ Observ. | 492.06 |
| | Retention Time | 2.743 min |
| 40 | LC Condition | |
| | Solvent A | 10% methanol:90% Water:0.1% TFA |
| | Solvent B | 90% methanol:10% Water:0.1% TFA |
| | Start % B | 0 |
| | Final % B | 100 |
| 45 | Gradient Time | 3 min |
| | Flow Rate | 4 mL/min |
| | Wavelength | 220 |
| | Solvent Pair | methanol:Water:TFA |
| | Column | Phenomenex Luna 3 × 50 mm S10 |

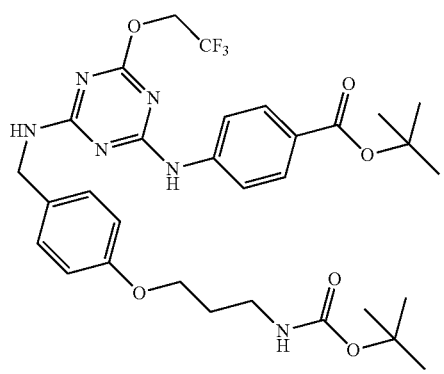 [SMILES: CC(C)(C)OC(=O)NCCCOc1ccc(CNc2nc(Nc3ccc(C(=O)OC(C)(C)C)cc3)nc(OCC(F)(F)F)n2)cc1]

tert-Butyl 4-(4-(4-(3-(tert-butoxycarbonylamino)propoxy)benzylamino)-6-(2,2,2-trifluoroethoxy)-1,3,5-triazin-2-ylamino)benzoate, TFA salt. To a solution of tert-butyl 4-(4-(4-hydroxybenzylamino)-6-(2,2,2-trifluoroethoxy)-1,3,5-triazin-2-ylamino)benzoate, TFA (45 mg, 0.074 mmol) in DMF (1 ml) was added cesium carbonate (72.6 mg, 0.223 mmol). The mixture was stirred at 45° C. for 20 mins. tert-Butyl 3-bromopropylcarbamate (21.24 mg, 0.089 mmol) was added and the resulting mixture was stirred at 40° C. for 16 hr and the completion of the reaction was monitored by LC/MS. Purification of the reaction mixture by preparative HPLC gave 35 mg (61.7%) of the title compound as TFA salt. $^1$H NMR (500 MHz, MeOD) δ ppm 1.42 (s, 9H), 1.61 (s, 9H), 1.91-1.94 (m, 2H), 3.23 (t, J=6.87 Hz, 2H), 4.01 (t, J=6.10 Hz, 2H), 4.58 (s, 2H), 4.87-4.94 (m, 2H), 6.89-6.92 (m, 2H), 7.29 (d, J=8.55 Hz, 2H), 7.69 (d, J=8.85 Hz, 2H), 7.78-8.00 (m, 2H).

tert-Butyl4-(4-(4-(3-(tert-butoxycarbonylamino)propoxy)benzylamino)-6-(2,2,2-trifluoroethoxy)-1,3,5-triazin-2-ylamino)benzoate, TFA salt.

| | |
|---|---|
| MS (M + H)$^+$ Calcd. | 649 |
| MS (M + H)$^+$ Observ. | 649.23 |
| Retention Time | 3.010 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

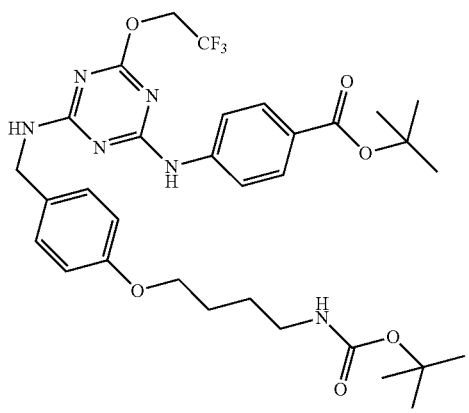 [SMILES: CC(C)(C)OC(=O)NCCCCOc1ccc(CNc2nc(Nc3ccc(C(=O)OC(C)(C)C)cc3)nc(OCC(F)(F)F)n2)cc1]

tert-Butyl 4-(4-(4-(4-(tert-butoxycarbonylamino)butoxy)benzylamino)-6-(2,2,2-trifluoroethoxy)-1,3,5-triazin-2-ylamino)benzoate, TFA salt. The title compound was prepared as TFA salt by analogy to the preparation of tert-butyl-4-(4-(4-(3-(tert-butoxycarbonylamino)propoxy)benzylamino)-6-(2,2,2-trifluoroethoxy)-1,3,5-triazin-2-ylamino)benzoate, TFA salt. $^1$H NMR (500 MHz, MeOD) δ ppm 1.44 (s, 9H), 1.61 (s, 9H), 1.64-2.01 (m, 4H), 3.10 (t, J=6.56 Hz, 2H), 3.89-4.16 (m, 2H), 4.58 (s, 2H), 4.81-5.10 (m, 2H), 6.74-7.02 (m, 2H), 7.19-7.41 (m, 2H), 7.68 (d, J=8.85 Hz, 2H), 7.78-8.06 (m, 2H).

tert-Butyl 4-(4-(4-(4-(tert-butoxycarbonylamino)butoxy)benzylamino)-6-(2,2,2-trifluoroethoxy)-1,3,5-triazin-2-ylamino)benzoate, TFA salt

| | |
|---|---|
| MS (M + H)$^+$ Calcd. | 663 |
| MS (M + H)$^+$ Observ. | 663.20 |
| Retention Time | 3.058 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

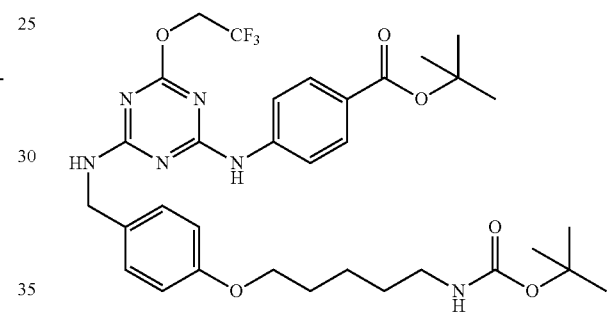

tert-Butyl 4-(4-(4-(5-(tert-butoxycarbonylamino)pentyloxy)benzylamino)-6-(2,2,2-trifluoroethoxy)-1,3,5-triazin-2-ylamino)benzoate, TFA salt. The title compound was prepared as TFA salt by analogy to the preparation of tert-butyl-4-(4-(4-(3-(tert-butoxycarbonylamino)propoxy)benzylamino)-6-(2,2,2-trifluoroethoxy)-1,3,5-triazin-2-ylamino)benzoate, TFA salt. $^1$H NMR (500 MHz, MeOD) δ ppm 1.44 (s, 9H), 1.46-1.58 (m, 4H), 1.61 (s, 9H), 1.68-1.95 (m, 2H), 3.06 (t, J=6.71 Hz, 2H), 3.97 (t, J=6.41 Hz, 3H), 4.58 (s, 2H), 4.88-4.93 (m, 2H), 6.76-7.06 (m, 2H), 7.15-7.40 (m, 2H), 7.68 (d, J=8.85 Hz, 2H), 7.78-8.04 (m, 2H).

tert-Butyl 4-(4-(4-(5-(tert-butoxycarbonylamino)pentyloxy)benzylamino)-6-(2,2,2-trifluoroethoxy)-1,3,5-triazin-2-ylamino)benzoate, TFA salt

| | |
|---|---|
| MS (M + H)$^+$ Calcd. | 677 |
| MS (M + H)$^+$ Observ. | 677.24 |
| Retention Time | 3.095 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

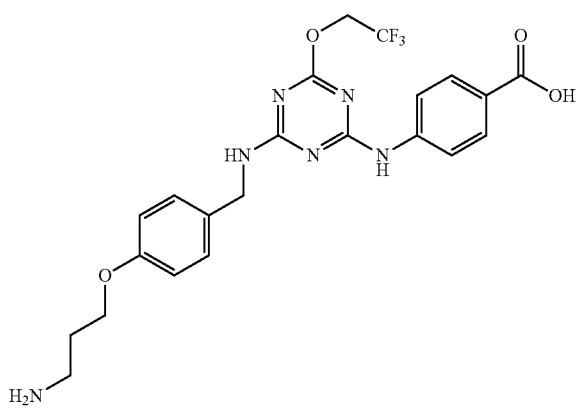 [SMILES: NCCCOc1ccc(CNc2nc(Nc3ccc(C(=O)O)cc3)nc(OCC(F)(F)F)n2)cc1]

4-(4-(4-(3-Aminopropoxy)benzylamino)-6-(2,2,2-trifluoroethoxy)-1,3,5-triazin-2-yl-amino)benzoicacid, HCl salt. tert-Butyl 4-(4-(4-(3-(tert-butoxycarbonylamino)propoxy)benzylamino)-6-(2,2,2-trifluoroethoxy)-1,3,5-triazin-2-ylamino)benzoate, TFA (32 mg, 0.042 mmol) in Dioxane (1.5 mL) was treated with conc. HCl (1.5 mL) at r.t. for 2 hrs. The completion of the reaction was monitored by LC/MS. The solvent was evaporated to give the dihydrochloride salt of the title compound as light yellow solid 23 mg (97%). $^1$H NMR (400 MHz, MeOD) δ ppm 1.98-2.29 (m, 2H), 3.00-3.21 (m, 2H), 4.11 (t, J=5.77 Hz, 2H), 4.61 (s, 2H), 4.95-5.01 (m, 2H), 6.77-7.08 (m, 2H), 7.17-7.45 (m, 2H), 7.67 (d, J=8.78 Hz, 2H), 7.89-8.09 (m, 2H).

| 4-(4-(4-(3-Aminopropoxy)benzylamino)-6-(2,2,2-trifluoroethoxy)-1,3,5-triazin-2-ylamino)benzoicacid, HCl salt. | |
|---|---|
| MS (M + H)$^+$ Calcd. | 493 |
| MS (M + H)$^+$ Observ. | 493.05 |
| Retention Time | 1.32 min |
| LC Condition | |
| Solvent A | 5% ACN:95% Water:10 mM NH$_4$OAc |
| Solvent B | 95% ACN:5% Water:10 mM NH$_4$OAc |
| Start % B | 0 |
| Final % B | 100 |
| Gradient Time | 2 min |
| Flow Rate | 4 mL/min |
| Wavelength | 220 |
| Solvent Pair | ACN:Water:10 mM NH$_4$OAc |
| Column | Phenomenex Luna 3 × 50 mm S10 |

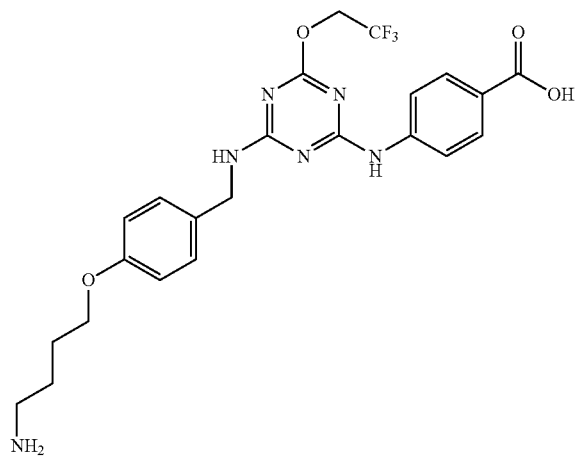 [SMILES: NCCCCOc1ccc(CNc2nc(Nc3ccc(C(=O)O)cc3)nc(OCC(F)(F)F)n2)cc1]

4-(4-(4-(4-Aminobutoxy)benzylamino)-6-(2,2,2-trifluoroethoxy)-1,3,5-triazin-2-ylamino)benzoic acid, HCl salt. The title compound was prepared as a dihydrochloride salt by analogy to the preparation of 4444443-aminopropoxy)benzylamino)-6-(2,2,2-trifluoroethoxy)-1,3,5-triazin-2-ylamino) Benzoic acid, HCl salt. $^1$H NMR (500 MHz, MeOD) δ ppm 1.74-2.11 (m, 4H), 2.91-3.12 (m, 2H), 4.05 (t, J=5.49 Hz, 2H), 4.61 (s, 2H), 4.94-5.02 (m, 2H), 6.81-7.02 (m, 2H), 7.31 (d, J=8.85 Hz, 2H), 7.68 (d, J=8.55 Hz, 2H), 7.92-8.07 (m, 2H).

| 4-(4-(4-(4-Aminobutoxy)benzylamino)-6-(2,2,2-trifluoroethoxy)-1,3,5-triazin-2-ylamino)benzoic acid, HCl salt. | |
|---|---|
| MS (M + H)$^+$ Calcd. | 507 |
| MS (M + H)$^+$ Observ. | 507.22 |
| Retention Time | 2.035 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

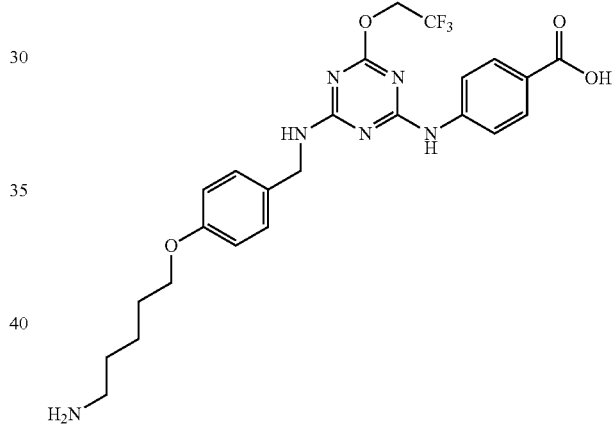

4-(4-(4-(5-Aminopentyloxy)benzylamino)-6-(2,2,2-trifluoroethoxy)-1,3,5-triazin-2-ylamino)benzoic acid, HCl salt. The title compound was prepared as a HCl salt by analogy to the preparation of 4-(4-(4-(3-aminopropoxy)benzylamino)-6-(2,2,2-trifluoroethoxy)-1,3,5-triazin-2-ylamino)benzoic acid, HCl salt.

| 4-(4-(4-(5-Aminopentyloxy)benzylamino)-6-(2,2,2-trifluoroethoxy)-1,3,5-triazin-2-ylamino)benzoic acid, HCl salt. | |
|---|---|
| MS (M + H)$^+$ Calcd. | 521 |
| MS (M + H)$^+$ Observ. | 521.13 |
| Retention Time | 2.107 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

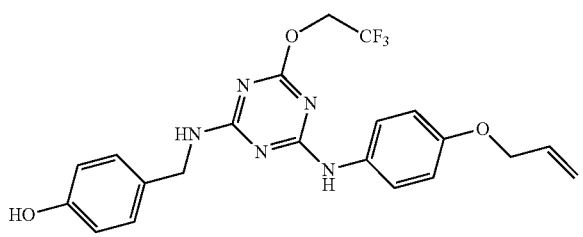 [SMILES: C=CCOc1ccc(Nc2nc(NCc3ccc(O)cc3)nc(OCC(F)(F)F)n2)cc1]

4-((4-(4-(Allyloxy)phenylamino)-6-(2,2,2-trifluoroethoxy)-1,3,5-triazin-2-ylamino) methyl)phenol, TFA salt. To a 0.1 M solution of 2,4-dichloro-6-(2,2,2-trifluoroethoxy)-1, 3,5-triazine in N-methylpyrrolidine (5 ml, 0.5 mmol) was added 4-(allyloxy)aniline (74.6 mg, 0.500 mmol) and diisopropylethylamine (DIEA) (0.175, 1.0 mmol) at r.t. The reaction mixture was stirred at r.t. for 30 mins and the completion of the reaction was monitored by LC/MS. 4-(Aminomethyl) phenol (61.6 mg, 0.500 mmol) was added followed by diisopropylethylamine (DIEA) (0.175, 1.0 mmol). The reaction mixture was stirred at r.t. for 16 hrs. The reaction mixture was purified by preparative HPLC to afford 135 mg (48.1%) of the title compound as TFA salt. $^1$H NMR (400 MHz, MeOD) δ ppm 4.47 (br. s., 2H), 4.54 (d, J=5.27 Hz, 2H), 4.93-5.03 (m, 2H), 5.25 (dt, J=10.5, 1.6 Hz, 1H), 5.40 (dt, J=17.3, 1.6 Hz, 1H), 6.07 (m, 1H), 6.74 (d, J=8.53 Hz, 2H), 6.82-7.01 (m, 2H), 7.07-7.25 (m, 2H), 7.35-7.62 (m, 2H).

| 4-((4-(4-(Allyloxy)phenylamino)-6-(2,2,2-trifluoroethoxy)-1,3,5-triazin-2-ylamino)methyl)phenol, TFA salt. | |
|---|---|
| MS (M + H)$^+$ Calcd. | 448 |
| MS (M + H)$^+$ Observ. | 448.16 |
| Retention Time | 2.403 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

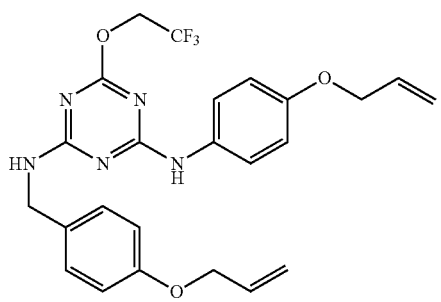 [SMILES: C=CCOc1ccc(CNc2nc(Nc3ccc(OCC=C)cc3)nc(OCC(F)(F)F)n2)cc1]

N2-(4-(allyloxy)benzyl)-N4-(4-(allyloxy)phenyl)-6-(2,2, 2-trifluoroethoxy)-1,3,5-triazine-2,4-diamine, TFA salt. To a solution of 4-((4-(4-(allyloxy)phenylamino)-6-(2,2,2-trifluoroethoxy)-1,3,5-triazin-2-ylamino)methyl)phenol, TFA salt (45 mg, 0.080 mmol) in DMF (2 ml) was added cesium carbonate (78 mg, 0.24 mmol). The mixture was stirred at 45° C. for 20 mins. 3-Bromoprop-1-ene (9.70 mg, 0.080 mmol) was added and the resulting mixture was stirred at 40° C. for 16 hrs. The completion of the reaction was monitored by LC/MS. Purification of the reaction mixture by preparative HPLC gave 24 mg (49.8%) of the title compound as TFA salt. $^1$H NMR (500 MHz, MeOD) δ ppm 4.43-4.67 (m, 6H), 4.83-4.95 (m, 2H), 5.17-5.33 (m, 2H), 5.33-5.52 (m, 2H), 5.96-6.19 (m, 2H), 6.81-7.02 (m, 4H), 7.14-7.33 (m, 2H), 7.38-7.59 (m, 2H).

| N2-(4-(allyloxy)benzyl)-N4-(4-(allyloxy)phenyl)-6-(2,2,2-trifluoroethoxy)-1,3,5-triazine-2,4-diamine, TFA salt. | |
|---|---|
| MS (M + H)$^+$ Calcd. | 488 |
| MS (M + H)$^+$ Observ. | 488.10 |
| Retention Time | 2.836 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

N2,N4-bis(4-(allyloxy)phenyl)-6-(2,2,2-trifluoroethoxy)-1,3,5-triazine-2,4-diamine, TFA salt. To a 0.13 M solution of 2,4-dichloro-6-(2,2,2-trifluoroethoxy)-1,3,5-triazine in N-methylpyrrolidine (7 ml, 0.91 mmol) was added 4-(allyloxy)aniline (272 mg, 1.82 mmol) and diisopropylethylamine (DIEA) (0.636, 3.64 mmol) at r.t. The reaction mixture was stirred at r.t. for 16 hrs. The reaction mixture was purified by preparative HPLC to afford 218 mg (40.8%) of the title compound as TFA salt. $^1$H NMR (500 MHz, MeOD) δ ppm 4.44-4.69 (m, 4H), 5.17-5.34 (m, 2H), 5.43 (dd, J=17.40, 1.83 Hz, 2H), 6.09 (dt, J=17.32, 5.23 Hz, 2H), 6.82-7.01 (m, 4H), 7.48 (d, J=9.77 Hz, 4H).

| N2,N4-bis(4-(allyloxy)phenyl)-6-(2,2,2-trifluoroethoxy)-1,3,5-triazine-2,4-diamine, TFA salt. | |
|---|---|
| MS (M + H)$^+$ Calcd. | 474 |
| MS (M + H)$^+$ Observ. | 474.04 |
| Retention Time | 2.910 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

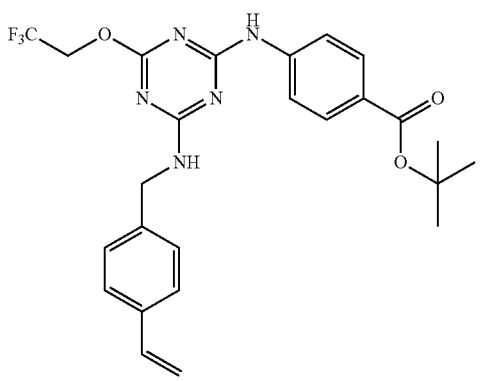 [SMILES: C=Cc1ccc(CNc2nc(Nc3ccc(C(=O)OC(C)(C)C)cc3)nc(OCC(F)(F)F)n2)cc1]

tert-Butyl 4-(4-(2,2,2-trifluoroethoxy)-6-(4-vinylbenzylamino)-1,3,5-triazin-2-ylamino)benzoate, TFA salt. To a 0.1 M solution of 2,4-dichloro-6-(2,2,2-trifluoroethoxy)-1,3,5-triazine in N-methylpyrrolidine (3 ml, 0.3 mmol) was added tert-butyl 4-aminobenzoate (58.0 mg, 0.300 mmol) and diisopropylethylamine (DIEA) (0.210 mL, 1.2 mmol) at r.t. The reaction mixture was stirred at r.t. for 30 mins and the completion of the reaction was monitored by LC/MS. (4-Vinylphenyl)methanamine (40.0 mg, 0.300 mmol) was added followed by DIEA (0.210 mL, 1.200 mmol). The reaction mixture was stirred at r.t. for 16 hrs. The reaction mixture was purified by preparative HPLC to afford 65 mg (35.2%) of the above compound as TFA salt. $^1$H NMR (500 MHz, MeOD) δ ppm 1.61 (s, 9H), 4.64 (s, 2H), 4.85-4.94 (m, 2H), 5.22 (d, J=10.99 Hz, 1H), 5.73-5.82 (m, 1H), 6.74 (dd, J=17.55, 10.83 Hz, 1H), 7.30-7.38 (m, 2H), 7.39-7.48 (m, 2H), 7.58-7.96 (m, 4H).

| tert-Butyl 4-(4-(2,2,2-trifluoroethoxy)-6-(4-vinylbenzylamino)-1,3,5-triazin-2-ylamino)benzoate, TFA salt. | |
|---|---|
| MS (M + H)$^+$ Calcd. | 502 |
| MS (M + H)$^+$ Observ. | 502.07 |
| Retention Time | 3.081 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

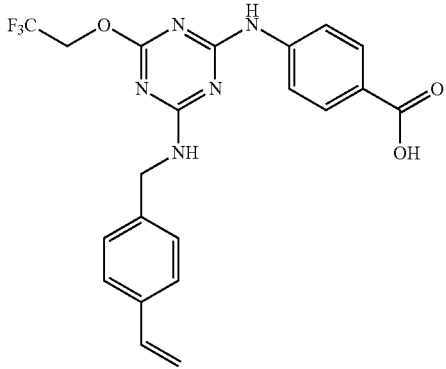 [SMILES: C=Cc1ccc(CNc2nc(Nc3ccc(C(=O)O)cc3)nc(OCC(F)(F)F)n2)cc1]

4-(4-(2,2,2-Trifluoroethoxy)-6-(4-vinylbenzylamino)-1,3,5-triazin-2-ylamino)benzoic acid, HCl salt. tert-Butyl 4-(4-(2,2,2-trifluoroethoxy)-6-(4-vinylbenzylamino)-1,3,5-triazin-2-ylamino)benzoate, TFA (180 mg, 0.292 mmol) in Dioxane (6 mL) was treated with conc. HCl (6 mL) at r.t. for 2 hrs. The completion of the reaction was monitored by LC/MS. The solvent was evaporated to give the above compound as hydrochloride salt 132 mg (94%). $^1$H NMR (400 MHz, DMSO-d$_6$) δ ppm 4.54 (dd, J=11.04, 6.53 Hz, 2H), 4.85-5.10 (m, 2H), 5.23 (ddd, J=10.92, 5.77, 1.13 Hz, 1H), 5.65-5.87 (m, 1H), 6.72 (ddd, J=17.44, 11.17, 5.52 Hz, 1H), 7.23-7.51 (m, 4H), 7.60-8.04 (m, 5H), 8.44 (br. s., 1H), 9.86-10.18 (m, 1H).

| 4-(4-(2,2,2-Trifluoroethoxy)-6-(4-vinylbenzylamino)-1,3,5-triazin-2-ylamino)benzoic acid, HCl salt. | |
|---|---|
| MS (M + H)$^+$ Calcd. | 446 |
| MS (M + H)$^+$ Observ. | 445.93 |
| Retention Time | 2.650 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

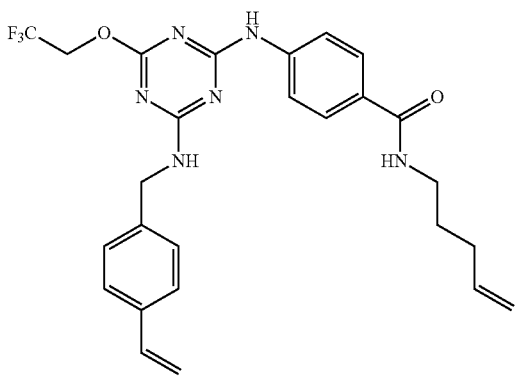 [SMILES: C=CCCCNC(=O)c1ccc(Nc2nc(NCc3ccc(C=C)cc3)nc(OCC(F)(F)F)n2)cc1]

N-(pent-4-enyl)-4-(4-(2,2,2-trifluoroethoxy)-6-(4-vinylbenzylamino)-1,3,5-triazin-2-ylamino)benzamide, TFA salt. To a solution of 4-(4-(2,2,2-trifluoroethoxy)-6-(4-vinylbenzylamino)-1,3,5-triazin-2-ylamino)benzoic acid, TFA (25 mg, 0.045 mmol) in DMF (1 mL) was added pent-4-en-1-amine (3.81 mg, 0.045 mmol), HATU (20.39 mg, 0.054 mmol), followed by DIEA (0.031 mL, 0.179 mmol). The reaction mixture was stirred at r.t. for 1 hr and the completion of the reaction was monitored by LC/MS. The reaction mixture was purified by preparative HPLC to afford 19 mg (67.9%) of the above compound as TFA salt. $^1$H NMR (500 MHz, MeOD) δ ppm 1.69-1.78 (m, 2H), 2.13-2.21 (m, 2H), 3.40 (t, J=7.17 Hz, 2H), 4.65 (s, 2H), 4.89-4.96 (m, 2H), 4.97-5.02 (m, 1H), 5.04-5.12 (m, 1H), 5.21 (d, J=10.99 Hz, 1H), 5.77 (d, J=18.62 Hz, 1H), 5.84-5.95 (m, 1H), 6.74 (dd, J=17.70, 10.99 Hz, 1H), 7.28-7.50 (m, 4H), 7.63-7.87 (m, 4H).

| N-(pent-4-enyl)-4-(4-(2,2,2-trifluoroethoxy)-6-(4-vinylbenzylamino)-1,3,5-triazin-2-ylamino)benzamide, TFA salt | |
|---|---|
| MS (M + H)+ Calcd. | 513 |
| MS (M + H)+ Observ. | 513.04 |
| Retention Time | 2.820 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

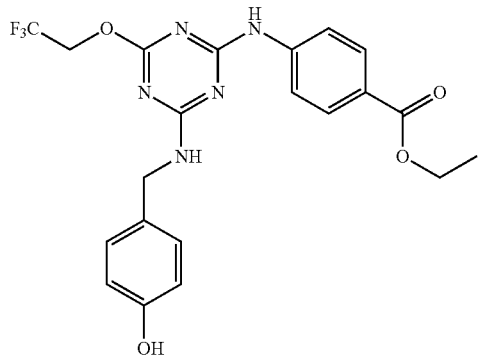 [SMILES: CCOC(=O)c1ccc(Nc2nc(NCc3ccc(O)cc3)nc(OCC(F)(F)F)n2)cc1]

Ethyl 4-(4-(4-hydroxybenzylamino)-6-(2,2,2-trifluoroethoxy)-1,3,5-triazin-2-ylamino)benzoate, TFA salt. The title compound was prepared as TFA salt by analogy to the preparation of tert-butyl 4-(4-(4-hydroxybenzylamino)-6-(2,2,2-trifluoroethoxy)-1,3,5-triazin-2-ylamino)benzoate, TFA salt. $^1$H NMR (500 MHz, DMSO-$d_6$) δ ppm 1.31 (t, 3H), 4.28 (q, 2H), 4.42 (d, 2H), 4.91-5.06 (m, 2H), 6.65-6.77 (m, 2H), 7.14 (dd, J=8.55, 2.14 Hz, 2H), 7.74-7.97 (m, 4H), 8.32 (br. s., 1H), 9.29 (br. s., 1H), 9.94-10.12 (m, 1H).

| Ethyl 4-(4-(4-hydroxybenzylamino)-6-(2,2,2-trifluoroethoxy)-1,3,5-triazin-2-ylamino)benzoate, TFA salt | |
|---|---|
| MS (M + H)+ Calcd. | 464 |
| MS (M + H)+ Observ. | 463.92 |
| Retention Time | 1.837 min |
| LC Condition | |
| Solvent A | 5% MeOH:95% Water:10 mM Ammonium Acetate |
| Solvent B | 95% MeOH:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | MeOH:Water:Ammonium Acetate |
| Column | Phenomenex Luna 3 × 50 mm S10 |

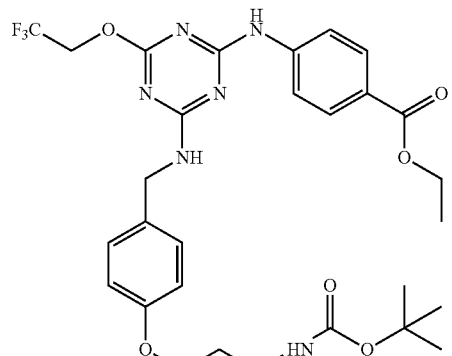

Ethyl 4-(4-(4-(3-(tert-butoxycarbonylamino)propoxy)benzylamino)-6-(2,2,2-trifluoroethoxy)-1,3,5-triazin-2-ylamino)benzoate, TFA salt. To a solution of ethyl 4-(4-(4-hydroxybenzylamino)-6-(2,2,2-trifluoroethoxy)-1,3,5-triazin-2-ylamino)benzoate, TFA salt (218 mg, 0.378 mmol) in DMF (4 ml) was added potassium carbonate (157 mg, 1.133 mmol) and tert-Butyl 3-bromopropylcarbamate (134 mg, 0.566 mmol). The resulting mixture was stirred at room temperature for 16 hrs and the completion of the reaction was monitored by LC/MS. Purification of the reaction mixture by preparative HPLC gave 145 mg (52.3%) of the title compound as TFA salt. $^1$H NMR (400 MHz, MeOD) δ ppm 1.29-1.52 (m, 12H), 1.85-1.98 (m, 2H), 3.21 (t, J=6.78 Hz, 2H), 3.95-4.05 (m, 2H), 4.35 (q, J=7.19 Hz, 2H), 4.57 (s, 2H), 4.85-4.95 (m, 2H), 6.82-6.98 (m, 2H), 7.28 (d, J=8.53 Hz, 2H), 7.64-8.01 (m, 4H).

| Ethyl 4-(4-(4-(3-(tert-butoxycarbonylamino)propoxy)benzylamino)-6-(2,2,2-trifluoroethoxy)-1,3,5-triazin-2-ylamino)benzoate, TFA salt. | |
|---|---|
| MS (M + H)+ Calcd. | 621 |
| MS (M + H)+ Observ. | 621.02 |
| Retention Time | 2.876 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

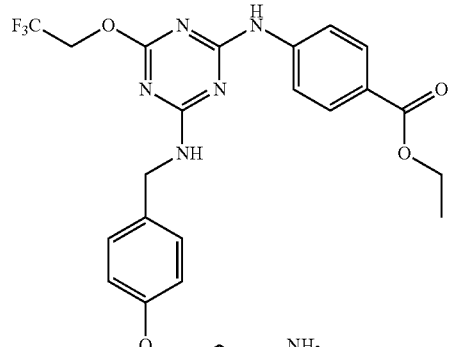

Ethyl 4-(4-(4-(3-aminopropoxy)benzylamino)-6-(2,2,2-trifluoroethoxy)-1,3,5-triazin-2-ylamino)benzoate, TFA salt.

The solution of ethyl 4-(4-(4-(3-(tert-butoxycarbonylamino)propoxy)benzylamino)-6-(2,2,2-trifluoroethoxy)-1,3,5-triazin-2-ylamino)benzoate, TFA salt (244 mg, 0.332 mmol) in DCM (2 mL) was treated with TFA (1 mL, 12.98 mmol). The reaction mixture was stirred at room temperature for 2 hrs. The completion of the reaction was monitored by LCMS. The solvent was evaporated to give 229 mg (92%) of the title compound as TFA salt.

| Ethyl 4-(4-(4-(3-aminopropoxy)benzylamino)-6-(2,2,2-trifluoroethoxy)-1,3,5-triazin-2-ylamino)benzoate, TFA salt. | |
|---|---|
| MS (M + H)+ Calcd. | 521 |
| MS (M + H)+ Observ. | 521.1 |
| Retention Time | 2.875 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 4 min |
| Flow Rate | 5 mL/min |
| Wavelength | 220 |
| Solvent Pair | methanol:Water:TFA |
| Column | Phenomenex Luna 3 × 50 mm S10 |

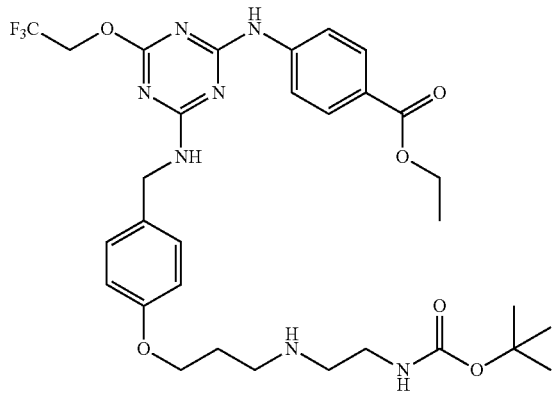 [SMILES: CCOC(=O)c1ccc(Nc2nc(NCc3ccc(OCCCNCCNC(=O)OC(C)(C)C)cc3)nc(OCC(F)(F)F)n2)cc1]

Ethyl 4-(4-(4-(3-(2-(tert-butoxycarbonylamino)ethylamino)propoxy)benzylamino)-6-(2,2,2-trifluoroethoxy)-1,3,5-triazin-2-ylamino)benzoate, TFA salt. To a solution of ethyl 4-(4-(4-(3-aminopropoxy)benzylamino)-6-(2,2,2-trifluoroethoxy)-1,3,5-triazin-2-ylamino)benzoate, TFA salt (50 mg, 0.067 mmol) in ethanol (5 mL) was added tert-butyl 2-oxoethylcarbamate (21.3 mg, 0.134 mmol) and sodium cyanoborohydride (16.8 mg, 0.267 mmol). The reaction mixture was stirred at 50° C. for 16 hrs. Excess tert-butyl 2-oxoethylcarbamate was added and the reaction mixture was stirred at 60° C. for 1 hr. Purification by preparative HPLC gave 18 mg (30.2%) of the title compound as TFA salt. $^1$H NMR (500 MHz, MeOD) δ ppm 1.38-1.43 (m, 3H), 1.48 (s, 9H), 2.14-2.24 (m, 2H), 3.14-3.18 (m, 2H), 3.23-3.31 (m, 2H), 3.35-3.40 (m, 2H), 4.08-4.17 (m, 2H), 4.32-4.41 (m, 2H), 4.59 (s, 2H), 4.85-4.95 (m, 2H), 6.91-7.02 (m, 2H), 7.25-7.37 (m, 2H), 7.68-8.00 (m, 4H).

| Ethyl 4-(4-(4-(3-(2-(tert-butoxycarbonylamino)ethylamino)propoxy)benzylamino)-6-(2,2,2-trifluoroethoxy)-1,3,5-triazin-2-ylamino)benzoate, TFA salt. | |
|---|---|
| MS (M + H)+ Calcd. | 664 |
| MS (M + H)+ Observ. | 664.23 |
| Retention Time | 2.013 min |
| LC Condition | |
| Solvent A | 5% MeOH:95% Water:10 mM Ammonium Acetate |
| Solvent B | 95% MeOH:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | MeOH:Water:Ammonium Acetate |
| Column | Phenomenex Luna 3 × 50 mm S10 |

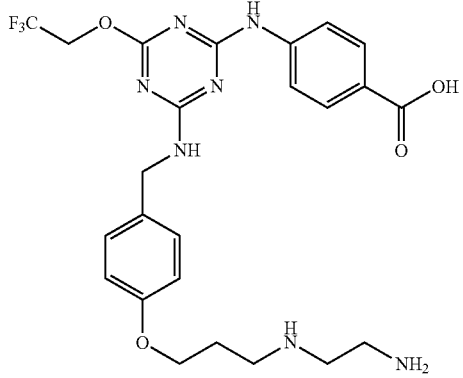 [SMILES: NCCNCCCOc1ccc(CNc2nc(Nc3ccc(C(=O)O)cc3)nc(OCC(F)(F)F)n2)cc1]

4-(4-(4-(3-(2-Aminoethylamino)propoxy)benzylamino)-6-(2,2,2-trifluoroethoxy)-1,3,5-triazin-2-ylamino)benzoic acid, HCl salt. To a solution of ethyl 4-(4-(4-(3-(2-(tert-butoxycarbonylamino)ethylamino)propoxy)benzylamino)-6-(2,2,2-trifluoro-ethoxy)-1,3,5-triazin-2-ylamino)benzoate, TFA salt (35 mg, 0.039 mmol) in Dioxane (1 ml) was added 2N LiOH (1 ml). The mixture was stirred at r.t. for 16 hrs. Preparative HPLC purification gave the acid intermediate. The acid intermediate was treated with 4N HCl in Dioxane (2 ml). The reaction mixture was stirred at room temperature for 2 hrs. The solvent was evaporated to give 21 mg (83% for 2 steps) of the title compound as HCl salt. $^1$H NMR (500 MHz, MeOD) δ ppm 2.01-2.06 (2H, m), 2.88-3.10 (6H, m), 4.13 (2H, t, J=6.3 Hz), 4.55 (2H, s), 4.82-4.92 (2H, m), 6.96 (2H, d, J=8.9 Hz), 7.29 (2H, d, J=8.9 Hz), 7.47 (2H, d, J=7.6 Hz), 7.81 (2H, d, J=7.6 Hz).

| 4-(4-(4-(3-(2-Aminoethylamino)propoxy)benzylamino)-6-(2,2,2-trifluoroethoxy)-1,3,5-triazin-2-ylamino)benzoic acid, HCl salt. | |
|---|---|
| MS (M + H)+ Calcd. | 536 |
| MS (M + H)+ Observ. | 536.04 |
| Retention Time | 1.565 min |
| LC Condition | |
| Solvent A | 5% MeOH:95% Water:10 mM Ammonium Acetate |
| Solvent B | 95% MeOH:5% Water:10 mM Ammonium Acetate |

-continued 4-(4-(4-(3-(2-Aminoethylamino)propoxy)benzylamino)-6-(2,2,2-trifluoroethoxy)-1,3,5-triazin-2-ylamino)benzoic acid, HCl salt.

| | |
|---|---|
| Start % B | 0 |
| Final % B | 100 |
| Gradient Time | 2 min |
| Flow Rate | 1 mL/min |
| Wavelength | 220 |
| Solvent Pair | MeOH:Water:Ammonium Acetate |
| Column | Phenomenex Luna 2.0 × 30 mm 3 um |

Example 2001

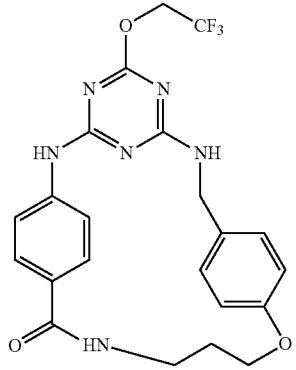 [SMILES: O=C1NCCCOc2ccc(cc2)CNc2nc(nc(OCC(F)(F)F)n2)Nc2ccc1cc2]

The solution of 4-(4-(4-(3-aminopropoxy)benzylamino)-6-(2,2,2-trifluoroethoxy)-1,3,5-triazin-2-ylamino)benzoic acid, HCl salt (22 mg, 0.039 mmol) and diisopropylethylamine (DIEA) (0.068 mL, 0.389 mmol) in dimethylformamide (1 mL) was diluted by dichloromethane (100 mL). The resulted solution was added 2-(7-Aza-1H-benztriazol-1-yl)-1,1,3,3-tetramethyluronium hexafluorophosphate (HATU) (22.19 mg, 0.058 mmol) in dichloromethane (100 mL). The reaction mixture was stirred at r.t. for 1 hr. The solvent was evaporated and the residue was purified by preparative HPLC to afford 7 mg (29.7%) of the above compound as a TFA salt. Preparative HPLC conditions: Phenomenex Luna C18 30×100 mm S10, 30 to 100% B over 18 minute gradient, 6 minute hold time, A=10% methanol 90% water 0.1% TFA, B=90% methanol 10% water 0.1% TFA. Flow rate: 35 ml/min. $^1$H NMR (400 MHz, MeOD) δ ppm 2.02-2.18 (m, 2H), 3.62 (t, J=5.90 Hz, 2H), 4.01-4.24 (m, 2H), 4.42 (s, 2H), 4.90-4.96 (m, 2H), 6.56 (d, J=8.78 Hz, 2H), 6.79 (d, J=8.53 Hz, 2H), 7.14 (d, J=8.78 Hz, 2H), 7.24-7.39 (m, 2H).

| Example 2001 | |
|---|---|
| MS (M + H)$^+$ Calcd. | 475 |
| MS (M + H)$^+$ Observ. | 475.08 |
| Retention Time | 1.58 min |
| LC Condition | |
| Solvent A | 5% ACN:95% Water:10 mM Ammonium Acetate |
| Solvent B | 95% ACN:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | ACN:Water:Ammonium Acetate |
| Column | Phenomenex Luna 3 × 50 mm S10 |

Example 2002

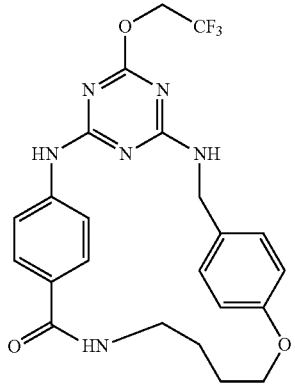 [SMILES: O=C1NCCCCOc2ccc(cc2)CNc2nc(nc(OCC(F)(F)F)n2)Nc2ccc1cc2]

The above compound was prepared as a TFA salt by analogy to Example 2001. $^1$H NMR (500 MHz, MeOD) δ ppm 1.75-1.98 (m, 4H), 3.44-3.57 (m, 2H), 3.97-4.21 (m, 2H), 4.54 (s, 2H), 4.86-4.98 (m, 2H), 6.80 (d, J=8.85 Hz, 2H), 7.10 (d, J=8.85 Hz, 2H), 7.20-7.38 (m, 4H).

| Example 2002 | |
|---|---|
| MS (M + H)$^+$ Calcd. | 489 |
| MS (M + H)$^+$ Observ. | 489.11 |
| Retention Time | 1.668 min |
| LC Condition | |
| Solvent A | 5% ACN:95% Water:10 mM Ammonium Acetate |
| Solvent B | 95% ACN:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | ACN:Water:Ammonium Acetate |
| Column | Phenomenex Luna 3 × 50 mm S10 |

Example 2003

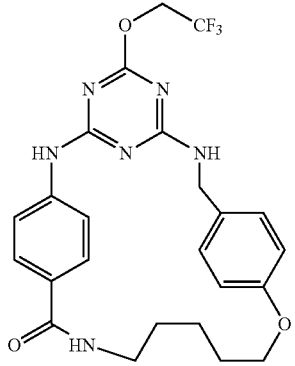 [SMILES: O=C1NCCCCCOc2ccc(cc2)CNc2nc(nc(OCC(F)(F)F)n2)Nc2ccc1cc2]

The above compound was prepared as a TFA salt by analogy to Example 2001. $^1$H NMR (400 MHz, DMSO-d$_6$) δ ppm 1.38-1.51 (m, 2H), 1.52-1.63 (m, 2H), 1.64-1.79 (m, 2H), 3.20-3.32 (m, 2H), 4.04 (t, J=6.78 Hz, 2H), 4.44 (d, J=5.77 Hz, 2H), 5.00 (q, J=9.03 Hz, 2H), 6.92 (d, J=8.53 Hz, 2H), 7.15 (d, J=8.78 Hz, 2H), 7.23-7.43 (m, 4H), 8.22 (t, J=5.90 Hz, 1H), 8.33 (t, J=5.65 Hz, 1H), 9.78 (s, 1H).

Example 2003

| | |
|---|---|
| MS (M + H)+ Calcd. | 503 |
| MS (M + H)+ Observ. | 503.14 |
| Retention Time | 1.675 min |
| LC Condition | |
| Solvent A | 5% ACN:95% Water:10 mM Ammonium Acetate |
| Solvent B | 95% ACN:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | ACN:Water:Ammonium Acetate |
| Column | Phenomenex Luna 3 × 50 mm S10 |

Example 2004

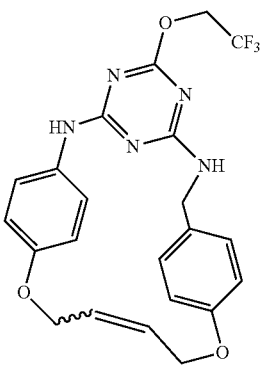 [SMILES: FC(F)(F)COc1nc2nc(n1)Nc1ccc(cc1)OCC=CCOc1ccc(cc1)CN2]

To a solution of N2-(4-(allyloxy)benzyl)-N4-(4-(allyloxy)phenyl)-6-(2,2,2-trifluoro-ethoxy)-1,3,5-triazine-2,4-diamine, TFA salt (35 mg, 0.058 mmol) in dichloroethane (150 ml) in a sealed tube, nitrogen was bubbled in for 30 mins. Under nitrogen GrubbsII catalyst (14 mg, 0.016 mmol) was added. The sealed tube was sealed and the reaction mixture was stirred at 70° C. for 5 hrs. The solvent was evaporated and the residue was purified by preparative HPLC to afford 22 mg (65.9%) of the above compound as TFA salt. Preparative HPLC condition: Phenomenex Luna C18 30×100 mm S10, 30 to 100% B over 18 minute gradient, 6 minute hold time, A=10% methanol 90% water 0.1% TFA, B=90% methanol 10% water 0.1% TFA. Flow rate: 35 ml/min. $^1$H NMR (500 MHz, MeOD) δ ppm 4.52 (s, 2H), 4.57-4.66 (m, 2H), 4.72 (dd, J=6.26, 1.07 Hz, 2H), 4.94-5.07 (m, 2H), 5.52 (dt, J=15.79, 6.14 Hz, 1H), 5.96 (dt, J=15.95, 4.84 Hz, 1H), 6.64 (d, J=8.85 Hz, 2H), 6.78 (d, J=8.85 Hz, 2H), 7.06 (d, J=8.55 Hz, 2H), 7.15 (d, J=9.16 Hz, 2H).

Example 2004

| | |
|---|---|
| MS (M + H)+ Calcd. | 460 |
| MS (M + H)+ Observ. | 460.08 |
| Retention Time | 1.788 min |
| LC Condition | |
| Solvent A | 5% ACN:95% Water:10 mM Ammonium Acetate |
| Solvent B | 95% ACN:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | ACN:Water:Ammonium Acetate |
| Column | Phenomenex Luna 3 × 50 mm S10 |

Example 2005

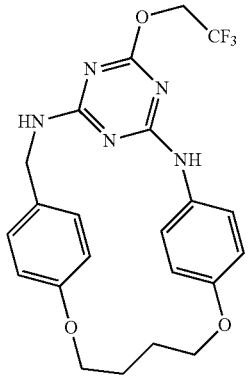 [SMILES: FC(F)(F)COc1nc2nc(n1)Nc1ccc(cc1)OCCCCOc1ccc(cc1)CN2]

To a solution of example 2004 (15 mg, 0.026 mmol) in ethyl acetate (10 ml) was added 10% palladium on carbon (10 mg, 0.07 mmol). The reaction mixture was stirred under hydrogen balloon at r.t. for 4 h. The reaction mixture was filtered through a pad of celite. The solvent was evaporated and the residue was purified by preparative HPLC to afford 10 mg (65.1%) of the above compound as TFA salt. Preparative HPLC condition: Phenomenex Luna C18 30×100 mm S10, 30 to 100% B over 18 minute gradient, 6 minute hold time, A=10% methanol 90% water 0.1% TFA, B=90% methanol 10% water 0.1% TFA. Flow rate: 35 ml/min. $^1$H NMR (500 MHz, MeOD) δ ppm 1.57-1.76 (m, 2H), 1.76-2.01 (m, 2H), 4.16 (t, J=6.10 Hz, 2H), 4.23 (t, J=5.80 Hz, 2H), 4.58 (s, 2H), 4.98 (q, J=8.55 Hz, 2H), 6.45-6.62 (m, 2H), 6.72 (d, J=8.85 Hz, 2H), 7.01 (d, J=8.55 Hz, 2H), 7.07-7.22 (m, 2H).

Example 2005

| | |
|---|---|
| MS (M + H)+ Calcd. | 462 |
| MS (M + H)+ Observ. | 462.10 |
| Retention Time | 1.825 min |
| LC Condition | |
| Solvent A | 5% ACN:95% Water:10 mM Ammonium Acetate |
| Solvent B | 95% ACN:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | ACN:Water:Ammonium Acetate |
| Column | Phenomenex Luna 3 × 50 mm S10 |

Example 2006

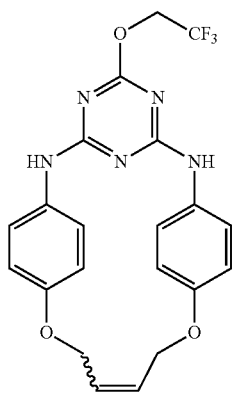 [SMILES: FC(F)(F)COc1nc2nc(n1)Nc1ccc(cc1)OCC=CCOc1ccc(cc1)N2]

To a solution of N2,N4-bis(4-(allyloxy)phenyl)-6-(2,2,2-trifluoroethoxy)-1,3,5-triazine-2,4-diamine, TFA salt (40 mg, 0.068 mmol) in DCE (100 ml) in a sealed tube, nitrogen was bubbled in for 30 mins Under nitrogen GrubbsII catalyst (10 mg, 0.012 mmol) was added. The reaction mixture was sealed and stirred at 70° C. for 16 hrs. The solvent was evaporated and the residue was purified by preparative HPLC to afford 24 mg (59.9%) of the above compound as TFA salt. Preparative HPLC condition: Phenomenex Luna C18 30×100 mm S10, 30 to 100% B over 18 minute gradient, 6 minute hold time, A=10% methanol 90% water 0.1% TFA, B=90% methanol 10% water 0.1% TFA. Flow rate: 35 ml/min. $^1$H NMR (500 MHz, MeOD) δ ppm 4.74-4.75 (m, 4H), 4.93-5.02 (m, 2H), 5.87 (t, J=3.05 Hz, 2H), 6.74 (d, J=9.16 Hz, 4H), 7.04 (d, J=8.85 Hz, 4H).

| Example 2006 | |
|---|---|
| MS (M + H)$^+$ Calcd. | 446 |
| MS (M + H)$^+$ Observ. | 445.92 |
| Retention Time | 1.832 min |
| LC Condition | |
| Solvent A | 5% ACN:95% Water:10 mM Ammonium Acetate |
| Solvent B | 95% ACN:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | ACN:Water:Ammonium Acetate |
| Column | Phenomenex Luna 3 × 50 mm S10 |

Example 2007

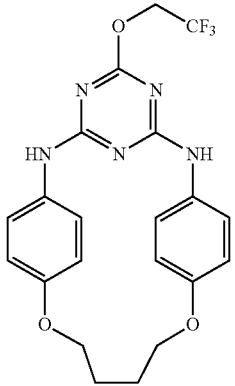 [SMILES: FC(F)(F)COc1nc2nc(n1)Nc1ccc(cc1)OCCCCOc1ccc(cc1)N2]

To a solution of example 2006 (13 mg, 0.023 mmol) in ethyl acetate (10 ml) was added 10% palladium on carbon (5 mg). The reaction mixture was stirred under hydrogen balloon at r.t. for 16 h. The reaction mixture was filtered through a pad of celite. The solvent was evaporated and the residue was purified by preparative HPLC to afford 9 mg (68.3%) of the above compound as TFA salt. Preparative HPLC condition: Phenomenex Luna C18 30×100 mm S10, 30 to 100% B over 18 minute gradient, 6 minute hold time, A=10% methanol 90% water 0.1% TFA, B=90% methanol 10% water 0.1% TFA. Flow rate: 35 ml/min. $^1$H NMR (500 MHz, MeOD) δ ppm 1.74 (dt, 4H), 4.13-4.36 (m, 4H), 4.91-4.96 (m, 2H), 6.78 (d, J=9.16 Hz, 4H), 6.99 (d, J=8.85 Hz, 4H).

| Example 2007 | |
|---|---|
| MS (M + H)$^+$ Calcd. | 448 |
| MS (M + H)$^+$ Observ. | 448.0 |
| Retention Time | 3.050 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

Example 2008

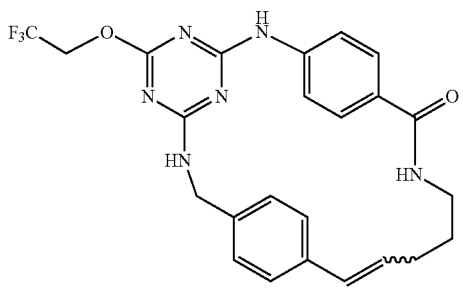 [SMILES: O=C1NCCCC=Cc2ccc(cc2)CNc2nc(nc(OCC(F)(F)F)n2)Nc2ccc1cc2]

To a solution of N-(pent-4-enyl)-4-(4-(2,2,2-trifluoroethoxy)-6-(4-vinylbenzylamino)-1,3,5-triazin-2-ylamino)benzamide, TFA salt (6 mg, 9.58 mmol) in DCE (5 ml) in a sealed tube, nitrogen was bubbled in for ½ hr. Under nitrogen Grubbs ll catalyst (1 mg, 1.178 mmol) was added. The reaction mixture was sealed and stirred at 70° C. for 2 hrs. The solvent was evaporated and the residue was purified by preparative HPLC to afford 3 mg (49.7%) of the above compound as TFA salt. Preparative HPLC condition: Phenomenex Luna C18 30×100 mm S10, 20 to 100% B over 18 minute gradient, 6 minute hold time, A=10% methanol 90% water 0.1% TFA, B=90% methanol 10% water 0.1% TFA. Flow rate: 40 ml/min. $^1$H NMR (500 MHz, DMSO-d$_6$) δ ppm 1.62-1.88 (m, 2H), 2.30-2.45 (m, 2H), 4.45 (d, J=5.19 Hz, 2H), 4.98 (q, J=8.95 Hz, 2H), 6.33-6.64 (m, 2H), 6.91-7.12 (m, 4H), 7.17 (d, J=8.24 Hz, 2H), 7.38 (d, J=8.24 Hz, 2H), 7.55 (t, J=6.10 Hz, 1H), 8.21 (t, J=5.34 Hz, 1H), 9.65 (s, 1H).

| Example 2008 | |
|---|---|
| MS (M + H)$^+$ Calcd. | 485 |
| MS (M + H)$^+$ Observ. | 484.97 |
| Retention Time | 2.505 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

Example 2009

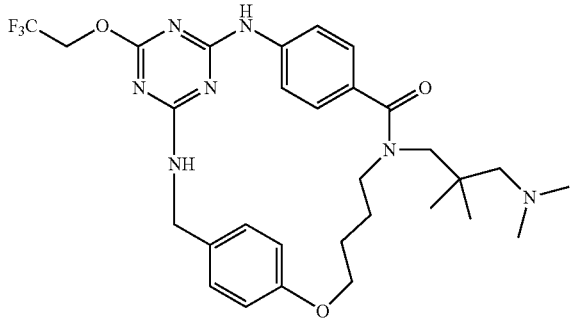 [SMILES: CN(C)CC(C)(C)CN1CCCCOc2ccc(cc2)CNc2nc(nc(OCC(F)(F)F)n2)Nc2ccc(cc2)C1=O]

| Example 2009 | |
|---|---|
| MS (M + H)$^+$ Calcd. | 602 |
| MS (M + H)$^+$ Observ. | 602.10 |
| Retention Time | 1.942 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |
| NMR | |
| $^1$H NMR (400 MHz, MeOD) | δ ppm 1.23 (s, 6 H), 1.33-1.42 (m, 2 H), 1.67-1.79 (m, 2 H), 2.99 (s, 6 H), 3.08 (s, 2 H), 3.12-3.21 (m, 2 H), 3.55 (s, 2 H), 4.12 (t, J = 5.65 Hz, 2 H), 4.60 (s, 2 H), 4.90 (q, J = 8.62 Hz, 2 H), 6.92 (d, J = 8.78 Hz, 2 H), 6.97 (d, J = 8.78 Hz, 2 H), 7.20 (d, J = 8.53 Hz, 2 H), 7.37 (d, J = 8.53 Hz, 2 H). |

Example 2010

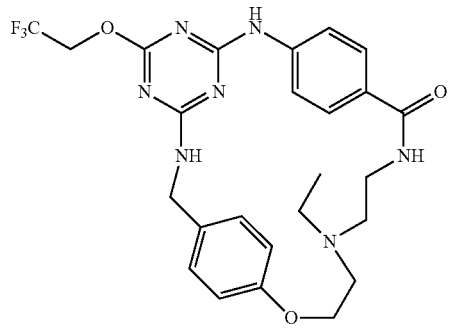 [SMILES: CCN1CCNC(=O)c2ccc(cc2)Nc2nc(nc(OCC(F)(F)F)n2)NCc2ccc(cc2)OCC1]

| Example 2010 | |
|---|---|
| MS (M + H)$^+$ Calcd. | 532 |
| MS (M + H)$^+$ Observ. | 531.95 |
| Retention Time | 1.788 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |
| NMR | |
| $^1$H NMR (500 MHz, MeOD) | δ ppm 1.57 (t, J = 7.17 Hz, 3 H), 3.36-3.83 (m, 7 H), 3.96-4.27 (m, 3 H), 4.57 (br. s., 2 H), 4.88-4.96 (m, 2 H), 6.80 (d, J = 8.55 Hz, 2 H), 7.09 (d, J = 8.55 Hz, 2 H), 7.20-7.28 (m, 2 H), 7.30-7.37 (m, 2 H). |

Example 2011

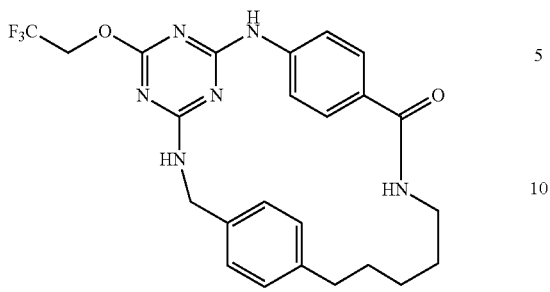

|  | Example 2011 |
|---|---|
| MS (M + H)+ Calcd. | 487 |
| MS (M + H)+ Observ. | 487.03 |
| Retention Time | 1.750 min |
|  | LC Condition |
| Solvent A | 5% MeOH:95% Water:10 mM Ammonium Acetate |
| Solvent B | 95% MeOH:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | MeOH:Water:Ammonium Acetate |
| Column | Phenomenex Luna 3 × 50 mm S10 |
|  | NMR |
| 1H NMR (500 MHz, MeOD) | δ ppm 1.30-1.36 (m, 2 H), 1.57-1.71 (m, 4 H), 2.60 (t, J = 5.80 Hz, 2 H), 3.39-3.43 (m, 2 H), 4.59 (s, 2 H), 4.89-4.95 (m, 2 H), 7.02 (d, J = 8.55 Hz, 2 H), 7.06-7.13 (m, 2 H), 7.41 (d, J = 8.85 Hz, 2 H), 7.55 (d, J = 8.85 Hz, 2 H). |

Example 2012

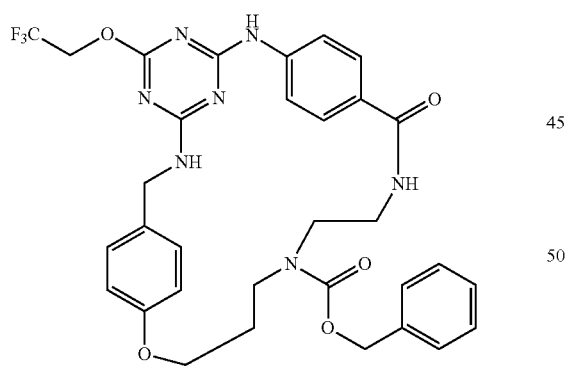

|  | Example 2012 |
|---|---|
| MS (M + H)+ Calcd. | 652 |
| MS (M + H)+ Observ. | 652.20 |
| Retention Time | 1.767 min |
|  | LC Condition |
| Solvent A | 5% MeOH:95% Water:10 mM Ammonium Acetate |
| Solvent B | 95% MeOH:5% Water:10 mM Ammonium Acetate |

-continued

| Example 2012 | |
|---|---|
| Start % B | 0 |
| Final % B | 100 |
| Gradient Time | 2 min |
| Flow Rate | 4 mL/min |
| Wavelength | 220 |
| Solvent Pair | MeOH:Water:Ammonium Acetate |
| Column | Phenomenex Luna 3 × 50 mm S10 |
| NMR | |
| $^1$H NMR (500 MHz, DMSO-d$_6$) | δ ppm 1.82-1.91 (m, 2 H), 3.25 (dd, J = 7.02, 3.05 Hz, 2 H), 3.38-3.52 (m, 4 H), 3.92-4.02 (m, 2 H), 4.41-4.46 (m, 2 H), 4.99 (q, J = 8.95 Hz, 2 H), 5.10 (s, 2 H), 6.92 (br. s., 2 H), 7.15 (d, J = 8.55 Hz, 2 H), 7.28 (d, J = 8.85 Hz, 2 H), 7.30-7.45 (m, 7 H), 8.29-8.43 (m, 2 H), 9.79 (s, 1 H). |

Example 2013

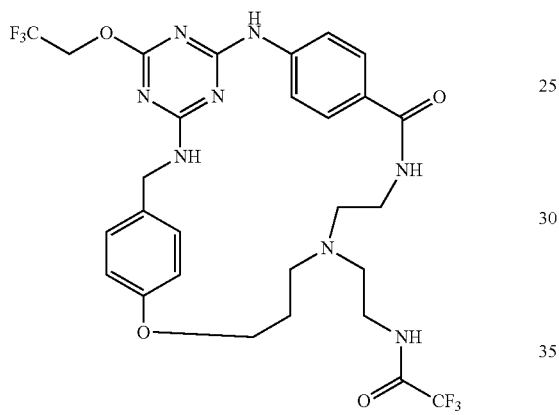

| Example 2013 | |
|---|---|
| MS (M + H)$^+$ Calcd. | 657 |
| MS (M + H)$^+$ Observ. | 657.29 |
| Retention Time | 2.098 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |
| NMR | |
| $^1$H NMR (500 MHz, MeOD) | δ ppm 2.06-2.16 (m, 2 H), 3.14-3.64 (m, 6 H), 3.77 (br. s., 2 H), 4.07 (br. s., 2 H), 4.14-4.33 (m, 2 H), 4.47-4.78 (m, 2 H), 4.85-4.98 (m, 2 H), 6.91 (d, J = 8.85 Hz, 2 H), 7.17 (d, J = 8.85 Hz, 2 H), 7.39-7.52 (m, 4 H). |

Example 2014

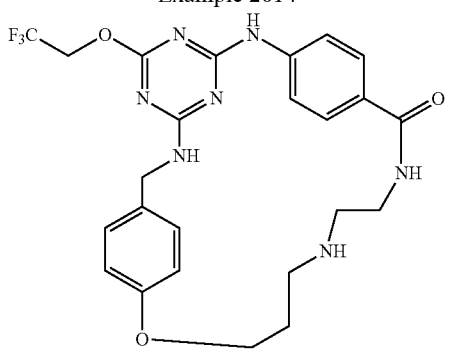

The solution of 4-(4-(4-(3-(2-aminoethylamino)propoxy) benzylamino)-6-(2,2,2-trifluoroethoxy)-1,3,5-triazin-2-ylamino)benzoic acid, HCl salt (8 mg, 0.025 mmol) and diisopropylethylamine (DIEA) (0.022 mL, 0.124 mmol) in dimethylformamide (1 mL) was diluted by dichloromethane (40 mL). The resulted solution was added 2-(7-Aza-1H-benztriazol-1-yl)-1,1,3,3-tetramethyluronium hexafluorophosphate (HATU) (4.7 mg, 0.012 mmol) in dichloromethane (40 mL). The reaction mixture was stirred at r.t. for 1 hr. The solvent was evaporated and the residue was purified by preparative HPLC to afford 3 mg (32.4%) of the above compound as a TFA salt. Preparative HPLC conditions: Phenomenex Luna C18 30×100 mm S10, 25 to 85% B over 15 minute gradient, 5 minute hold time, A=10% methanol 90% water 0.1% TFA, B=90% methanol 10% water 0.1% TFA. Flow rate: 35 ml/min.

The solution of 4-(4-(4-(3-(2-aminoethylamino)propoxy) benzylamino)-6-(2,2,2-trifluoroethoxy)-1,3,5-triazin-2-ylamino)benzoic acid, HCl salt (16 mg, 0.025 mmol) and diisopropylethylamine (DIEA) (0.043 mL, 0.248 mmol) in dimethylformamide (1 mL) was diluted by dichloromethane (100 mL). The resulted solution was added 2-(7-Aza-1H-benztriazol-1-yl)-1,1,3,3-tetramethyluronium hexafluorophosphate (HATU) (9.43 mg, 0.025 mmol) in dichloromethane (100 mL). The reaction mixture was stirred at r.t. for 1 hr. LCMS showed the formation of the cyclized intermediate. Acetic acid (2.84 μL, 0.050 mmol) and HATU (9.43 mg, 0.025 mmol) were added to the reaction mixture. The reaction mixture was stirred at r.t. for 1 hr. The solvent was evaporated and the residue was purified by preparative HPLC to afford 4 mg (22.7%) of the above compound as a TFA salt. Preparative HPLC conditions: Phenomenex Luna C18 30×100 mm S10, 20 to 90% B over 18 minute gradient, 4 minute hold time, A=10% methanol 90% water 0.1% TFA, B=90% methanol 10% water 0.1% TFA. Flow rate: 25 ml/min.

| Example 2014 | |
|---|---|
| MS (M + H)+ Calcd. | 518 |
| MS (M + H)+ Observ. | 518.04 |
| Retention Time | 1.668 min |
| LC Condition | |
| Solvent A | 5% MeOH:95% Water:10 mM Ammonium Acetate |
| Solvent B | 95% MeOH:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | MeOH:Water Ammonium Acetate |
| Column | Phenomenex Luna 3 × 50 mm S10 |
| NMR | |
| ¹H NMR (500 MHz, MeOD) | δ ppm 2.15-2.23 (m, 2 H), 3.26-3.39 (m, 4 H), 3.72-3.79 (m, 2 H), 4.16 (t, J = 5.49 Hz, 2 H), 4.58 (s, 2 H), 4.88-4.95 (m, 2 H), 6.96 (d, J = 8.55 Hz, 2 H), 7.23 (d, J = 8.55 Hz, 2 H), 7.34 (d, J = 8.55 Hz, 2 H), 7.39-7.45 (m, 2 H). |

Example 2015

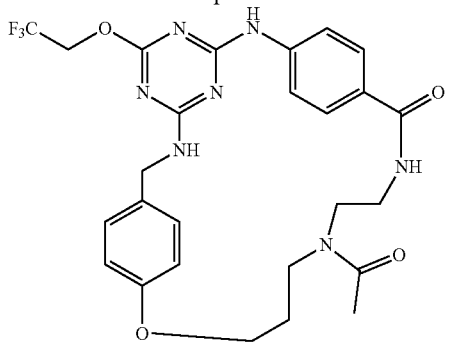

| Example 2015 | |
|---|---|
| MS (M + H)+ Calcd. | 657 |
| MS (M + H)+ Observ. | 657.29 |
| Retention Time | 2.098 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |
| NMR | |
| ¹H NMR (400 MHz, MeOD) | δ ppm 1.89-2.04 (m, 2 H), 2.11 (s, 3 H), 3.39-3.72 (m, 6 H), 3.93-4.10 (m, 2 H), 4.57 (s, 2 H), 4.86-5.01 (m, 2 H), 6.85-6.98 (m, 2 H), 7.12-7.46 (m, 6 H). |

Example 2016

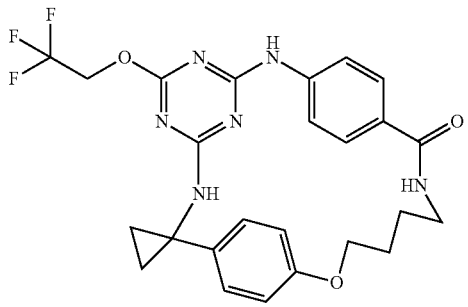 [SMILES: O=C1NCCCCOc2ccc(cc2)C2(CC2)Nc2nc(nc(OCC(F)(F)F)n2)Nc2ccc1cc2]

| Example 2016 | |
|---|---|
| MS (M + H)+ Calcd. | 515 |
| MS (M + H)+ Observ. | 515.22 |
| Retention Time | 7.74 min |
| LC Condition | |
| Solvent A | Water:10 mM Ammonium Acetate |
| Solvent B | ACN:10 mM Ammonium Acetate |
| Start % B | 10 |
| Final % B | 95 |
| Gradient Time | 11 min |
| Flow Rate | 1 mL/min |
| Wavelength | 220 |
| Solvent Pair | ACN:Water:Ammonium Acetate |
| Column | Waters Xbridge 4.6 × 150 mm 5 um C18 |

Example 2017

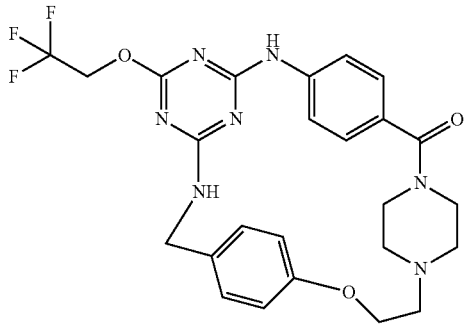 [SMILES: O=C1c2ccc(cc2)Nc2nc(nc(OCC(F)(F)F)n2)NCc2ccc(cc2)OCCN2CCN1CC2]

| Example 2017 | |
|---|---|
| MS (M + H)+ Calcd. | 530 |
| MS (M + H)+ Observ. | 530.26 |
| Retention Time | 6.26 min |
| LC Condition | |
| Solvent A | Water:10 mM Ammonium Acetate |
| Solvent B | ACN:10 mM Ammonium Acetate |
| Start % B | 10 |
| Final % B | 95 |
| Gradient Time | 11 min |
| Flow Rate | 1 mL/min |

| Example 2017 | |
|---|---|
| Wavelength | 220 |
| Solvent Pair | ACN:Water:Ammonium Acetate |
| Column | Waters Xbridge 4.6 × 150 mm 5 um C18 |

Example 2018

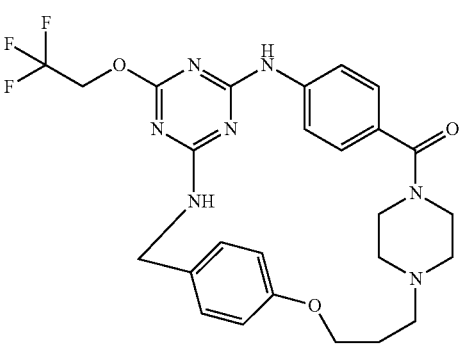 [SMILES: O=C1c2ccc(cc2)Nc2nc(nc(OCC(F)(F)F)n2)NCc2ccc(cc2)OCCCN2CCN1CC2]

| Example 2018 | |
|---|---|
| MS (M + H)+ Calcd. | 544 |
| MS (M + H)+ Observ. | 544.23 |
| Retention Time | 6.47 min |
| LC Condition | |
| Solvent A | Water:10 mM Ammonium Acetate |
| Solvent B | ACN:10 mM Ammonium Acetate |
| Start % B | 10 |
| Final % B | 95 |
| Gradient Time | 11 min |
| Flow Rate | 1 mL/min |
| Wavelength | 220 |
| Solvent Pair | ACN:Water:Ammonium Acetate |
| Column | Waters Xbridge 4.6 × 150 mm 5 um C18 |

Example 2019

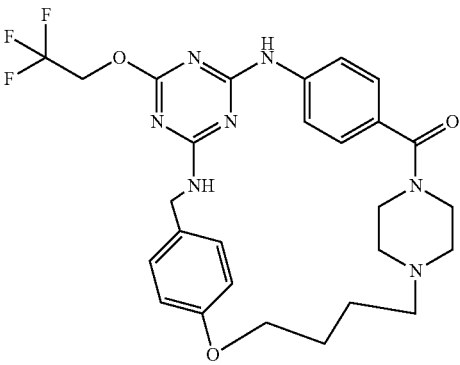

Example 2019

| | |
|---|---|
| MS (M + H)+ Calcd. | 558 |
| MS (M + H)+ Observ. | 558.29 |
| Retention Time | 6.95 min |
| | LC Condition |
| Solvent A | Water:10 mM Ammonium Acetate |
| Solvent B | ACN:10 mM Ammonium Acetate |
| Start % B | 10 |
| Final % B | 95 |
| Gradient Time | 11 min |
| Flow Rate | 1 mL/min |
| Wavelength | 220 |
| Solvent Pair | ACN:Water:Ammonium Acetate |
| Column | Waters Xbridge 4.6 × 150 mm 5 um C18 |

Example 2020

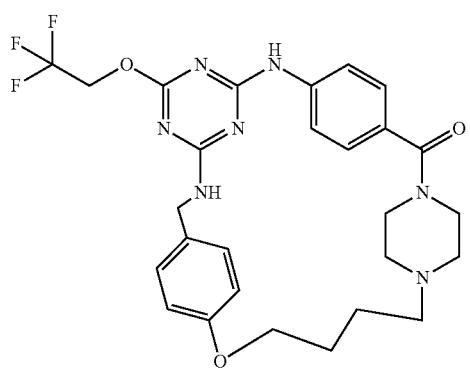 [SMILES: O=C1c2ccc(cc2)Nc2nc(nc(OCC(F)(F)F)n2)NCc2ccc(cc2)OCCCCN2CCN1CC2]

| | |
|---|---|
| MS (M + H)+ Calcd. | 572 |
| MS (M + H)+ Observ. | 572.27 |
| Retention Time | 7.37 min |
| | LC Condition |
| Solvent A | Water:10 mM Ammonium Acetate |
| Solvent B | ACN:10 mM Ammonium Acetate |
| Start % B | 10 |
| Final % B | 95 |
| Gradient Time | 11 min |
| Flow Rate | 1 mL/min |
| Wavelength | 220 |
| Solvent Pair | ACN:Water:Ammonium Acetate |
| Column | Waters Xbridge 4.6 × 150 mm 5 um C18 |

Example 2021

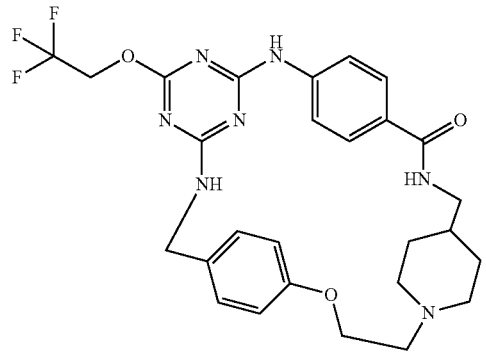 [SMILES: O=C1NCC2CCN(CCOc3ccc(cc3)CNc3nc(nc(OCC(F)(F)F)n3)Nc3ccc1cc3)CC2]

| | |
|---|---|
| MS (M + H)+ Calcd. | 558 |
| MS (M + H)+ Observ. | 558.26 |
| Retention Time | 5.46 min |
| | LC Condition |
| Solvent A | Water:10 mM Ammonium Acetate |
| Solvent B | ACN:10 mM Ammonium Acetate |
| Start % B | 10 |
| Final % B | 95 |
| Gradient Time | 11 min |
| Flow Rate | 1 mL/min |
| Wavelength | 220 |
| Solvent Pair | ACN:Water:Ammonium Acetate |
| Column | Waters Xbridge 4.6 × 150 mm 5 um C18 |

Example 2022

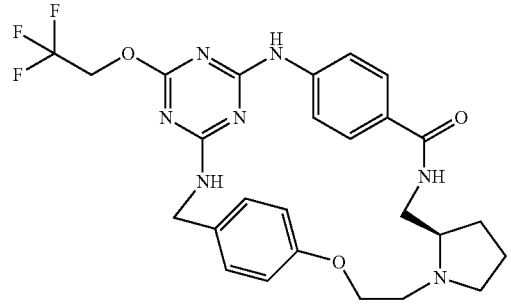 [SMILES: O=C1NC[C@H]2CCCN2CCOc2ccc(cc2)CNc2nc(nc(OCC(F)(F)F)n2)Nc2ccc1cc2]

| | |
|---|---|
| MS (M + H)+ Calcd. | 544 |
| MS (M + H)+ Observ. | 544.2 |
| Retention Time | 7.24 min |
| | LC Condition |
| Solvent A | Water:10 mM Ammonium Acetate |
| Solvent B | ACN:10 mM Ammonium Acetate |
| Start % B | 10 |
| Final % B | 95 |
| Gradient Time | 11 min |

Example 2022

| | |
|---|---|
| Flow Rate | 1 mL/min |
| Wavelength | 220 |
| Solvent Pair | ACN:Water:Ammonium Acetate |
| Column | Waters Xbridge 4.6 × 150 mm 5 um C18 |

Example 2023

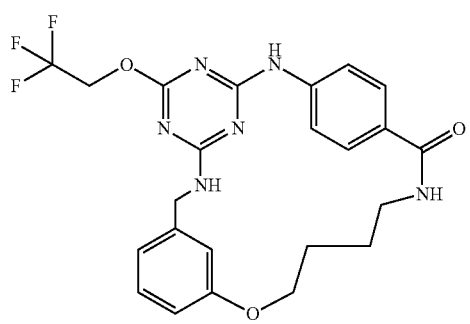 [SMILES: O=C1NCCCCOc2cccc(c2)CNc2nc(nc(OCC(F)(F)F)n2)Nc2ccc1cc2]

Example 2023

| | |
|---|---|
| MS (M + H)+ Calcd. | 489 |
| MS (M + H)+ Observ. | 489.24 |
| Retention Time | 7.31 min |
| | LC Condition |
| Solvent A | Water:10 mM Ammonium Acetate |
| Solvent B | ACN:10 mM Ammonium Acetate |
| Start % B | 10 |
| Final % B | 95 |
| Gradient Time | 11 min |
| Flow Rate | 1 mL/min |
| Wavelength | 220 |
| Solvent Pair | ACN:Water:Ammonium Acetate |
| Column | Waters Xbridge 4.6 × 150 mm 5 um C18 |

The next section describes the synthesis of 3000 series compounds.

Example 3001

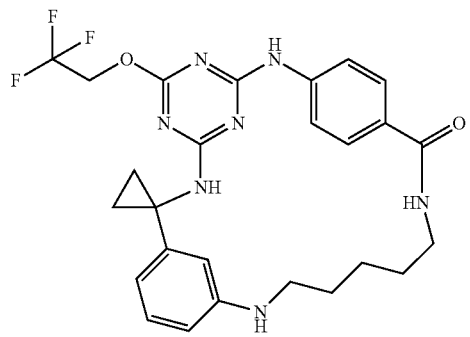 [SMILES: O=C1NCCCCCNc2cccc(c2)C2(CC2)Nc2nc(nc(OCC(F)(F)F)n2)Nc2ccc1cc2]

Example 3001

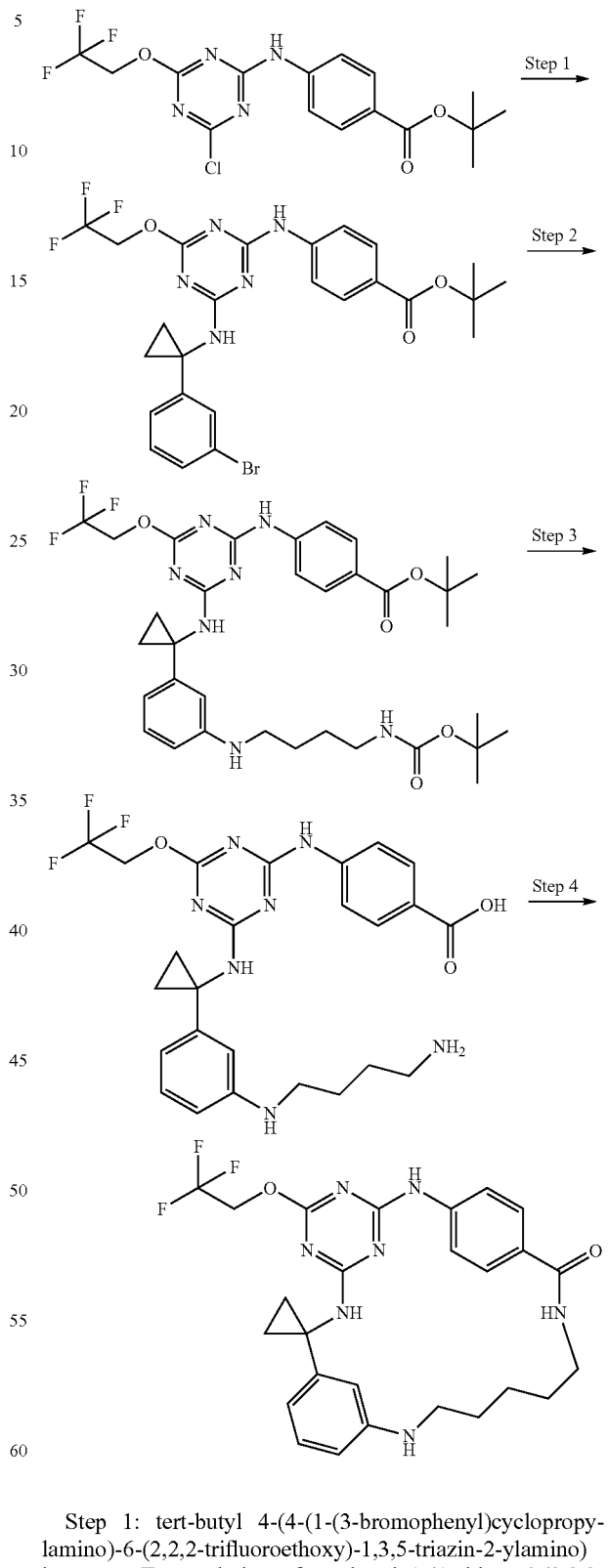

Step 1: tert-butyl 4-(4-(1-(3-bromophenyl)cyclopropylamino)-6-(2,2,2-trifluoroethoxy)-1,3,5-triazin-2-ylamino)benzoate. To a solution of tert-butyl 4-(4-chloro-6-(2,2,2-trifluoroethoxy)-1,3,5-triazin-2-ylamino)benzoate (1156 mg, 2 mmol) in THF (10 mL) was added 1-(3-bromophenyl)

cyclopropanamine (424 mg, 2.000 mmol) and Hunig's Base (1.747 mL, 10.00 mmol). The resulting mixture was stirred for 16 h. After concentration, the residue was purified by Biotage eluting with 20% ethyl acetate in hexane to give 400 mg (35%) of the desired product as a solid.

| tert-butyl 4-(4-(1-(3-(4-bromophenyl)cydopropylamino)-6-(2,2,2-trifluoroethoxy)-1,3,5-triazin-2-ylamino)benzoate | |
| --- | --- |
| MS (M)+ Calcd. | 687.34 |
| MS (M + H)+ Observ. | 688.37 |
| Retention Time | 2.96 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient/Stop Time | 3 min/4 min |
| Flow Rate | 1 mL/min |
| Wavelength | 220 |
| Solvent Pair | methanol:Water:TFA |
| Column | PHENOMENEX-LUNA 2.0 × 30 mm 3 um |

Step 2: tert-butyl 4-(4-(1-(3-(4-(tert-butoxycarbonylamino)butylamino)phenyl)cyclopropylamino)-6-(2,2,2-trifluoroethoxy)-1,3,5-triazin-2-ylamino)benzoate. To a mixture of tert-butyl 4-(4-(1-(3-bromophenyl)cyclopropylamino)-6-(2,2,2-trifluoroethoxy)-1,3,5-triazin-2-ylamino)benzoate (116 mg, 0.2 mmol), tert-butyl 4-aminobutylcarbamate (37.7 mg, 0.200 mmol), 2-(Di-t-butylphosphino)biphenyl (0.020 mmol), Pd2(dba)3 (18.31 mg, 0.020 mmol), K3PO4 (34.8 mg, 0.200 mmol) in a microwave tube in DME (Volume: 2 mL) was stirred for 3 h at 85° C. The reaction mixture was diluted with CH2Cl2, filtrated through a celite plug washing with CH2Cl2, concentrated to give a residue that was purified by Biotage eluting with 20%-50% ethyl acetate in hexane to give 38 mg (28%) of the desired product.

| tert-butyl 4-(4-(1-(3-(4-tert-butoxycarbonyl-amino)butylamino)phenyl)cyclopropylamino-6-(2,2,2-trifluoroethoxy)-1,3,5-triazin-2-ylamino)benzoate | |
| --- | --- |
| MS (M)+ Calcd. | 579.11 |
| MS (M + H)+ Observ. | 580.1 |
| Retention Time | 3.301 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient/Stop Time | 3 min/4 min |
| Flow Rate | 1 mL/min |
| Wavelength | 220 |
| Solvent Pair | methanol:Water:TFA |
| Column | PHENOMENEX-LUNA 2.0 × 30 mm 3 um |

Step 3: 4-(4-(1-(3-(4-aminobutylamino)phenyl)cyclopropylamino)-6-(2,2,2-trifluoroethoxy)-1,3,5-triazin-2-ylamino)benzoic acid, TFA salt. To a solution of tert-butyl 4-(4-(1-(3-(4-(tert-butoxycarbonylamino)butylamino)phenyl)cyclopropylamino)-6-(2,2,2-trifluoroethoxy)-1,3,5-triazin-2-ylamino)benzoate (38 mg, 0.055 mmol) in CH2Cl2 (Volume: 2 mL) was added TFA (0.017 mL, 0.221 mmol). The resulting mixture was stirred for 2 h. Concentration gave 35.7 mg (100%) of a crude product that will be used in the next step as it is.

| 4-(4-(1-(3-(4-aminobutylamino)phenyl)cyclopropylamino)-6-(2,2,2-trifluoroethoxy)-1,3,5-triazin-2-ylamino)benzoic acid, TFA salt | |
| --- | --- |
| MS (M)+ Calcd. | 531.22 |
| MS (M + H)+ Observ. | 532.17 |
| Retention Time | 2.30 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient/Stop Time | 3 min/4 min |
| Flow Rate | 1 mL/min |
| Wavelength | 220 |
| Solvent Pair | methanol:Water:TFA |
| Column | PHENOMENEX-LUNA 2.0 × 30 mm 3 um |

Step 4: To a solution of 4-(4-(1-(3-(5-aminopentylamino)phenyl)cyclopropylamino)-6-(2,2,2-trifluoroethoxy)-1,3,5-triazin-2-ylamino)benzoic acid, HCl (100 mg, 0.172 mmol), Hunig's Base (0.150 mL, 0.859 mmol) in CH2Cl2 (2 mL) was added HATU (98 mg, 0.258 mmol) and then stirred for 16 h. After concentration, the residue was purified by prep HPLC to give 10 mg (91%) of the desired product.

| Example 3001 | |
| --- | --- |
| MS (M)+ Calcd. | 527.23 |
| MS (M + H)+ Observ. | 528.19 |
| Retention Time | 2.325 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient/Stop Time | 3 min/4 min |
| Flow Rate | 1 mL/min |
| Wavelength | 220 |
| Solvent Pair | methanol:Water:TFA |
| Column | PHENOMENEX-LUNA 2.0 × 30 mm 3 um |

133
Example 3002
134
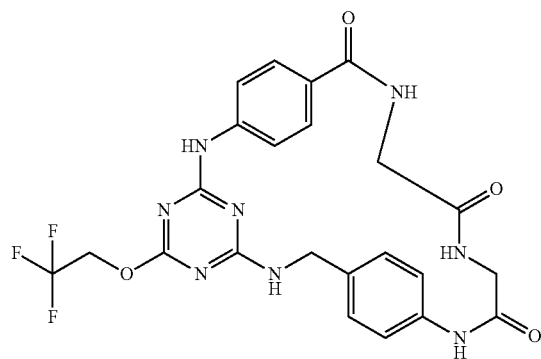 [SMILES: O=C1CNC(=O)c2ccc(cc2)Nc2nc(nc(OCC(F)(F)F)n2)NCc2ccc(cc2)NC(=O)CN1]
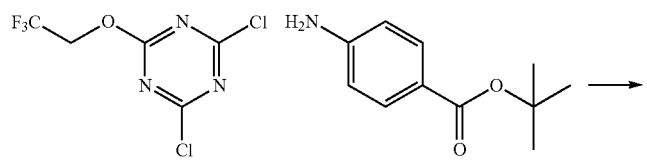
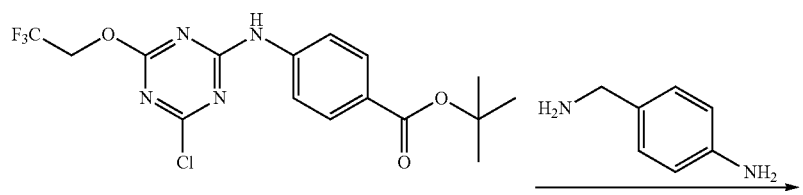
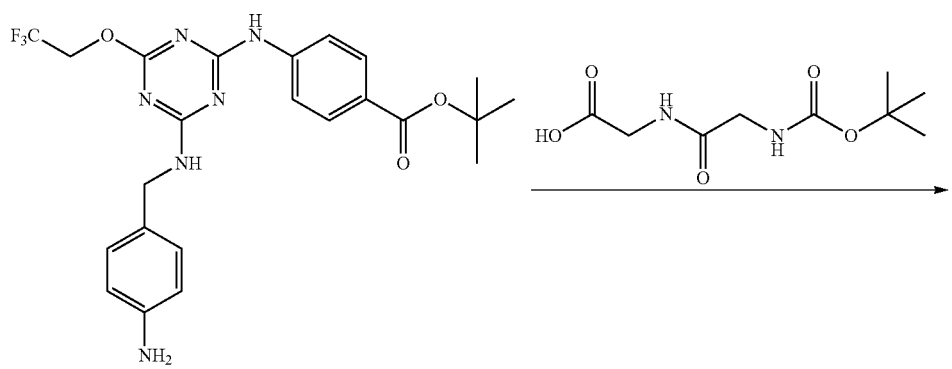
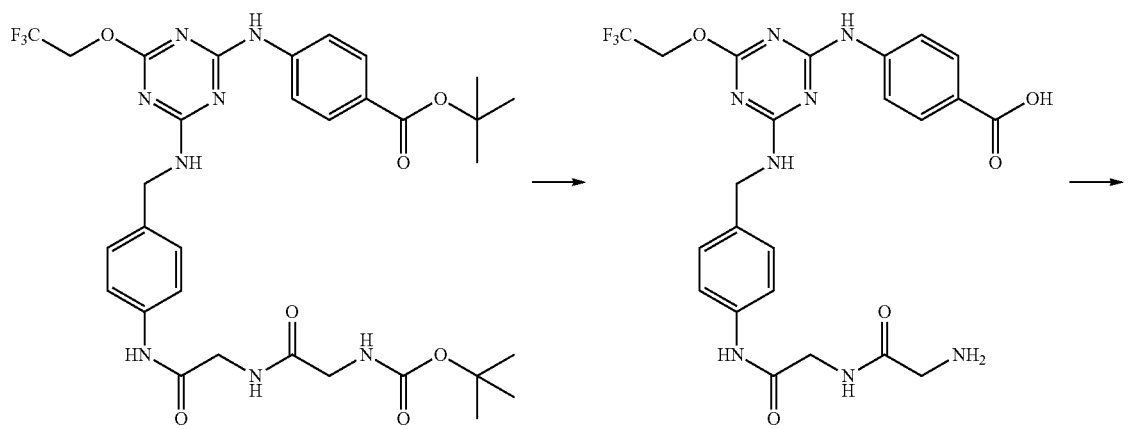

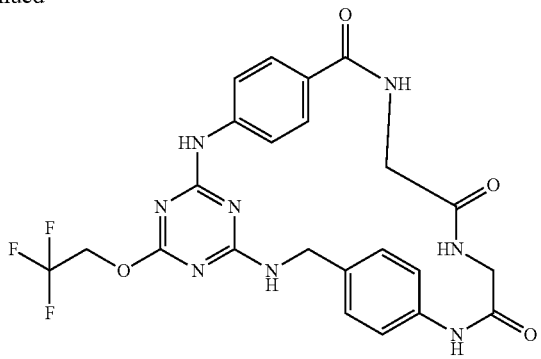

Step 1: To a solution of 2,4-dichloro-6-(2,2,2-trifluoroethoxy)-1,3,5-triazine (10 g, 40.3 mmol) in THF (100 mL) was added tert-butyl 4-aminobenzoate (7.79 g, 40.3 mmol) and Hunig's Base (7.04 mL, 40.3 mmol). The resulting mixture was stirred for 16 h. The precipitate was filtered and washed with Et$_2$O, dried, then washed with water and dried to give the tert-butyl 4-(4-chloro-6-(2,2,2-trifluoroethoxy)-1,3,5-triazin-2-ylamino)benzoate (10.6 g).

| tert-butyl 4-(4-chloro-6-(2,2,2-trifluoroethoxy)-1,3,5-triazin-2-ylamino)benzoate | |
|---|---|
| MS (M + H)$^+$ Calcd. | 405.1 |
| MS (M + H)$^+$ Observ. | 405.0 |
| Retention Time | 1.15 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 2: To a solution of the tert-butyl 4-(4-chloro-6-(2,2,2-trifluoroethoxy)-1,3,5-triazin-2-ylamino)benzoate (2 g, 4.94 mmol) in THF (10 mL) was added 4-(aminomethyl)aniline (0.616 mL, 5.44 mmol) and Hunig's Base (3.45 mL, 19.76 mmol). The resulting mixture was stirred for 16 h. The reaction was then warmed to 65° C. for 2 h at which point the reaction became a homogeneous solution. The reaction was cooled and diluted with DCM and washed with water and brine. The organic layer was collected, dried over sodium sulfate, and concentrated under vacuum to give an oily residue. The residue was purified by silica gel chromatography using 40% EtOAc/Hexanes to give tert-butyl 4-(4-(4-aminobenzylamino)-6-(2,2,2-trifluoroethoxy)-1,3,5-triazin-2-ylamino)benzoate (1.5 g).

| tert-butyl 4-(4-(4-aminobenzylamino)-6-(2,2,2-trifluoroethoxy)-1,3,5-triazin-2-ylamino)benzoate | |
|---|---|
| MS (M + H)$^+$ Calcd. | 491.2 |
| MS (M + H)$^+$ Observ. | 491.0 |
| Retention Time | 0.92 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 3: tert-butyl 4-(4-(4-aminobenzylamino)-6-(2,2,2-trifluoroethoxy)-1,3,5-triazin-2-ylamino)benzoate (100 mg, 0.204 mmol), 2-(2-(tert-butoxycarbonylamino)acetamido)acetic acid (56.8 mg, 0.245 mmol), HATU (116 mg, 0.306 mmol), and Hunig's Base (0.178 mL, 1.019 mmol) were stirred in DCM (3 mL) for 16 h. The solvent was removed and the crude material was purified by silica gel chromatography using EtOAc to give tert-butyl 4-(4-(4-(2-(2-(tert-butoxycarbonylamino)acetamido)acetamido)benzylamino)-6-(2,2,2-trifluoroethoxy)-1,3,5-triazin-2-ylamino)benzoate (144 mg).

| tert-butyl 4-(4-(4-(2-(2-(tert-butoxycarbonylamino)acetamido)acetamido)benzylamino)-6-(2,2,2-trifluoroethoxy)-1,3,5-triazin-2-ylamino)benzoate | |
|---|---|
| MS (M + H)$^+$ Calcd. | 705.3 |
| MS (M + H)$^+$ Observ. | 705.1 |
| Retention Time | 1.07 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 4: tert-butyl 4-(4-(4-(2-(2-(tert-butoxycarbonylamino)acetamido)acetamido)benzylamino)-6-(2,2,2-trifluoroethoxy)-1,3,5-triazin-2-ylamino)benzoate and 4 N HCl in Dioxane (2 mL, 8.00 mmol) were stirred for 1 h then concentrated under vacuum to give 4-(4-(4-(2-(2-amino acetamido)acetamido)benzylamino)-6-(2,2,2-trifluoroethoxy)-1,3,5-triazin-2-ylamino)benzoic acid (112 mg) which was carried to the next step without purification.

| 4-(4-(4-(2-(2-aminoacetamido)acetamido)benzylamino)-6-(2,2,2-trifluoroethoxy)-1,3,5-triazin-2-ylamino)benzoic acid | |
| --- | --- |
| MS (M + H)+ Calcd. | 549.2 |
| MS (M + H)+ Observ. | 549.0 |
| Retention Time | 0.76 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 5: 4-(4-(4-(2-(2-aminoacetamido)acetamido)benzylamino)-6-(2,2,2-trifluoroethoxy)-1,3,5-triazin-2-ylamino)benzoic acid (112 mg, 0.263 mmol), HATU (150 mg, 0.394 mmol), and Hunig's Base (0.229 mL, 1.313 mmol) were stirred in DMF (3 mL) for 16 h. The solvent was removed and the crude material was purified by reverse phase preparative HPLC to give Example 5001 (10 mg). $^1$H NMR (400 MHz, DMSO-d$_6$) δ ppm 4.25-4.36 (m, 1H), 4.36-4.56 (m, 4H), 4.92-5.08 (m, 3H), 7.08-7.25 (m, 6H), 7.45 (d, J=8.5 Hz, 2H), 7.60 (d, J=8.3 Hz, 1H), 8.01 (d, J=8.3 Hz, 1H), 8.23 (dd, J=6.1, 3.9 Hz, 1H), 9.60 (s, 1H), 9.66 (s, 1H).

| Example 3002 | |
| --- | --- |
| MS (M + H)+ Calcd. | 531.2 |
| MS (M + H)+ Observ. | 531.0 |
| Retention Time | 0.79 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 3003

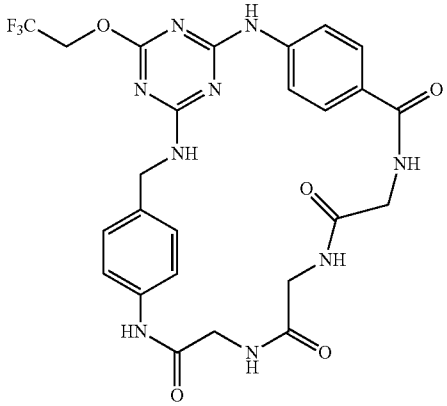 [SMILES: O=C1CNC(=O)CNC(=O)c2ccc(cc2)Nc2nc(nc(OCC(F)(F)F)n2)NCc2ccc(cc2)NC(=O)CN1]

The above compound was prepared by analogy to Example 3002. $^1$H NMR (400 MHz, DMSO-d$_6$) δ ppm 3.73 (d, 2H), 3.85 (d, J=5.5 Hz, 2H), 3.96 (d, J=5.3 Hz, 2H), 4.40 (d, J=5.5 Hz, 2H), 4.98 (q, J=9.2 Hz, 2H), 7.25 (dd, J=16.2, 8.7 Hz, 4H), 7.52 (d, J=8.8 Hz, 2H), 7.69 (d, J=8.5 Hz, 2H), 8.28 (t, J=5.3 Hz, 1H), 8.35 (ddd, J=15.6, 5.7, 5.5 Hz, 2H), 8.77 (t, J=5.3 Hz, 1H), 9.29 (s, 1H), 9.77 (s, 1H).

| Example 3003 | |
| --- | --- |
| MS (M + H)+ Calcd. | 588.2 |
| MS (M + H)+ Observ. | 588.0 |
| Retention Time | 0.78 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 3004

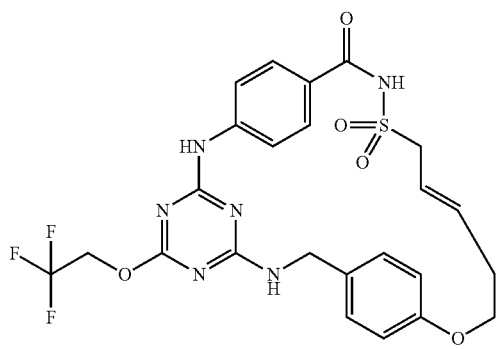

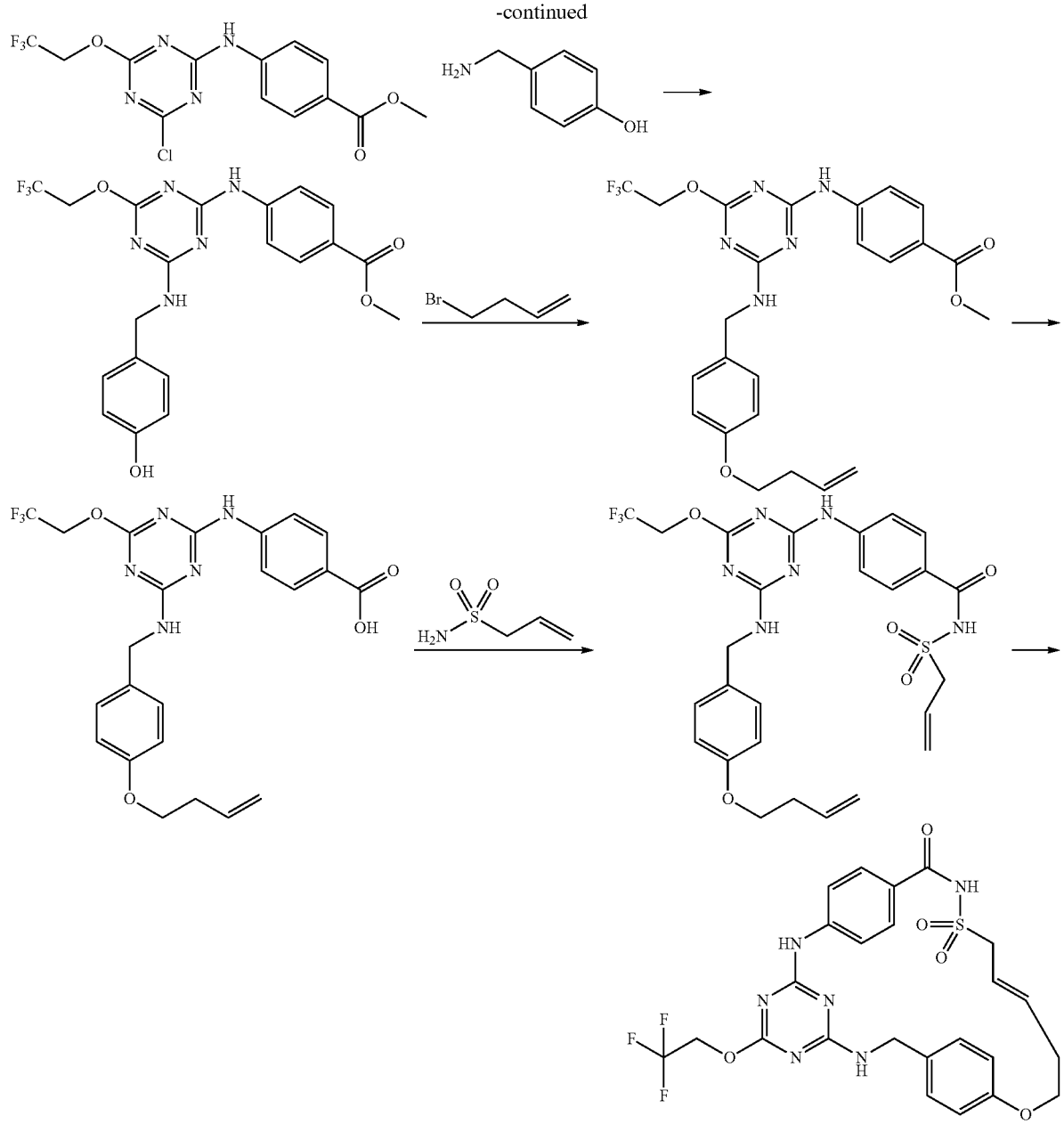

Step 1: To a solution of methyl 4-(4-chloro-6-(2,2,2-trifluoroethoxy)-1,3,5-triazin-2-ylamino)benzoate (intermediate from series 1000) (4 g, 5.07 mmol) in THF (30 mL) was added 4-(aminomethyl)phenol, HCl (0.891 g, 5.58 mmol) and Hunig's Base (3.54 mL, 20.29 mmol). The resulting mixture was stirred for 16 h. The reaction was then warmed to 65° C. for 2 h at which time the reaction became a homogeneous solution. The reaction was cooled and diluted with DCM and washed with water and brine. The organic layer was collected, dried over sodium sulfate, and concentrated under vacuum to give an oily residue. The residue was taken up in Et₂O and a white solid ppt from the mixture which was filtered and dried to give methyl 4-(4-(4-hydroxybenzylamino)-6-(2,2,2-trifluoroethoxy)-1,3,5-triazin-2-ylamino)benzoate (1.2 g).

| methyl 4-(4-(4-hydroxybenzylamino)-6-(2,2,2-trifluoroethoxy)-1,3,5-triazin-2-ylamino)benzoate | |
|---|---|
| MS (M + H)⁺ Calcd. | 450.1 |
| MS (M + H)⁺ Observ. | 449.9 |
| Retention Time | 2.12 min |
| LC Condition | |
| Solvent A | 90% Water -10% Methanol-0.1% TFA |
| Solvent B | 10% Water -90% Methanol-0.1% TFA |
| Start % B | 0 |
| Final % B | 100 |
| Gradient/Stop Time | 2 min/3 min |
| Flow Rate | 1 mL/min |
| Wavelength | 220 |
| Solvent Pair | Water - Methanol- TFA |
| Column | PHENOMENEX-LUNA 2.0 × 30 mm S10 3 µM |

Step 2: To a solution of methyl 4-(4-(4-hydroxybenzylamino)-6-(2,2,2-trifluoroethoxy)-1,3,5-triazin-2-ylamino)benzoate (100 mg, 0.223 mmol) in DMF (2 mL) was added 4-bromobut-1-ene (90 mg, 0.668 mmol) and Potassium Carbonate (154 mg, 1.113 mmol). The mixture was heated to 65° C. for 16 h. After cooling to rt, the mixture was diluted with EtOAc, washed with water, and brine. The organic layer was dried over MgSO$_4$ and concentrated. The crude product was purified by silica gel chromatography using 20-40% EtOAc/Hexanes to give methyl 4-(4-(4-(but-3-enyloxy)benzylamino)-6-(2,2,2-trifluoroethoxy)-1,3,5-triazin-2-ylamino)benzoate (45 mg).

| methyl 4-(4-(4-(but-3-enyloxy)benzylamino)-6-(2,2,2-trifluoroethoxy)-1,3,5-triazin-2-ylamino)benzoate | |
|---|---|
| MS (M + H)$^+$ Calcd. | 504.2 |
| MS (M + H)$^+$ Observ. | 504.0 |
| Retention Time | 1.14 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 3: methyl 4-(4-(4-(but-3-enyloxy)benzylamino)-6-(2,2,2-trifluoroethoxy)-1,3,5-triazin-2-ylamino)benzoate (46 mg, 0.091 mmol) was dissolved in THF (2 mL). LiOH (10.94 mg, 0.457 mmol) and Water (2 mL) were added to the solution and the reaction was warmed to 60° C. for 16 h. The reaction was diluted with DCM and acidified with 1 N HCl. The organic layer was collected, dried over sodium sulfate, and concentrated under vacuum to give 4-(4-(4-(but-3-enyloxy)benzylamino)-6-(2,2,2-trifluoroethoxy)-1,3,5-triazin-2-ylamino)benzoic acid (45 mg).

| 4-(4-(4-(but-3-enyloxy)benzylamino)-6-(2,2,2-trifluoroethoxy)-1,3,5-triazin-2-ylamino)benzoic acid | |
|---|---|
| MS (M + H)$^+$ Calcd. | 490.2 |
| MS (M + H)$^+$ Observ. | 490.0 |
| Retention Time | 1.04 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 4: 4-(4-(4-(but-3-enyloxy)benzylamino)-6-(2,2,2-trifluoroethoxy)-1,3,5-triazin-2-ylamino)benzoic acid (44 mg, 0.090 mmol), prop-2-ene-1-sulfonamide (13.07 mg, 0.108 mmol), HATU (51.3 mg, 0.135 mmol), and Hunig's Base (0.079 mL, 0.449 mmol) were stirred in DCM (3 mL) for 16 h. The solvent was removed and the crude material was purified by silica gel chromatography using EtOAc to give N-(allylsulfonyl)-4-(4-(4-(but-3-enyloxy)benzylamino)-6-(2,2,2-trifluoroethoxy)-1,3,5-triazin-2-ylamino)benzamide (45 mg).

| N-(allylsulfonyl)-4-(4-(4-(but-3-enyloxy)benzylamino)-6-(2,2,2-trifluoroethoxy)-1,3,5-triazin-2-ylamino)benzamide | |
|---|---|
| MS (M + H)$^+$ Calcd. | 593.2 |
| MS (M + H)$^+$ Observ. | 593.0 |
| Retention Time | 1.07 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 5: A solution of N-(allylsulfonyl)-4-(4-(4-(but-3-enyloxy)benzylamino)-6-(2,2,2-trifluoroethoxy)-1,3,5-triazin-2-ylamino)benzamide (70 mg, 0.118 mmol) in DCE (20 ml) was sparged with nitrogen for 30 min. and then HOVEYDA-GRUBBS CATALYST 2ND GENERATION (14.80 mg, 0.024 mmol) was added and the reaction heated to 80° C. for 16 h. The solvent was removed under vacuum and the crude material was purified by rev phase preparative HPLC using a gradient of 20-100% MeOH/water w/0.1% TFA modifier to give Example 3004. $^1$H NMR (400 MHz, DMSO-d$_6$) δ ppm 2.28-2.41 (m, 2H), 3.81 (t, J=5.3 Hz, 2H), 4.19 (d, J=7.5 Hz, 2H), 4.48 (d, J=5.3 Hz, 2H), 5.01 (q, J=9.2 Hz, 2H), 5.50-5.84 (m, 2H), 6.93 (d, J=8.8 Hz, 2H), 7.15 (d, J=8.5 Hz, 2H), 7.19-7.37 (m, 4H), 8.36-8.48 (m, 1H), 9.90 (s, 1H), 11.73 (s, 1H).

| Example 3004 | |
|---|---|
| MS (M + H)$^+$ Calcd. | 565.1 |
| MS (M + H)$^+$ Observ. | 565.0 |
| Retention Time | 0.96 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 3005

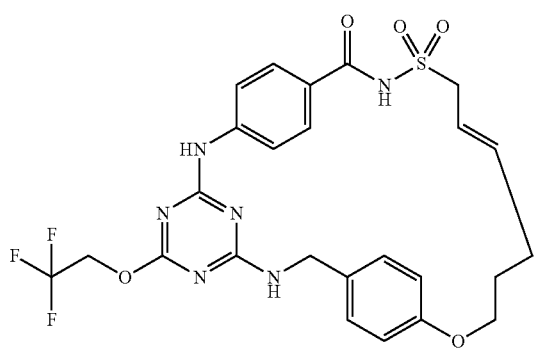 [SMILES: O=C1NS(=O)(=O)C/C=C/CCCOc2ccc(cc2)CNc2nc(nc(OCC(F)(F)F)n2)Nc2ccc1cc2]

The above compound was prepared by analogy to Example 3004. ¹H NMR (400 MHz, DMSO-$d_6$) δ ppm 1.69-1.81 (m, 2H), 2.18 (q, J=5.8 Hz, 2H), 3.89 (t, J=7.4 Hz, 2H), 4.20 (d, J=7.0 Hz, 2H), 4.47 (d, J=5.5 Hz, 2H), 4.99 (q, J=9.0 Hz, 2H), 5.44-5.76 (m, 2H), 6.94-7.00 (m, 2H), 7.16-7.23 (m, 2H), 7.36 (d, J=9.0 Hz, 2H), 7.62 (d, J=8.8 Hz, 2H), 8.51 (t, J=5.5 Hz, 1H), 9.95 (s, 1H), 11.87 (s, 1H).

| Example 3005 | |
|---|---|
| MS (M + H)⁺ Calcd. | 579.2 |
| MS (M + H)⁺ Observ. | 579.0 |
| Retention Time | 0.98 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 3006

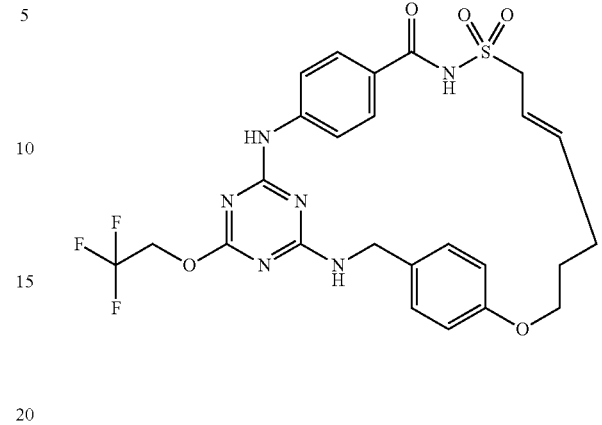

The above compound was prepared by analogy to Example 3004. ¹H NMR (400 MHz, DMSO-$d_6$) δ ppm 1.27-1.41 (m, 2H), 1.53-1.65 (m, 2H), 1.90-2.00 (m, 2H), 3.97 (t, J=5.6 Hz, 2H), 4.18 (d, J=7.3 Hz, 2H), 4.45 (d, J=5.8 Hz, 2H), 5.00 (q, J=9.0 Hz, 2H), 5.37-5.76 (m, 2H), 6.94-7.01 (m, 2H), 7.17-7.25 (m, 2H), 7.39 (d, J=8.8 Hz, 2H), 7.58 (d, J=8.8 Hz, 2H), 8.53 (t, J=5.8 Hz, 1H), 9.98 (s, 1H), 11.79 (s, 1H).

| Example 3006 | |
|---|---|
| MS (M + H)⁺ Calcd. | 593.0 |
| MS (M + H)⁺ Observ. | 593.2 |
| Retention Time | 1.01 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 3007

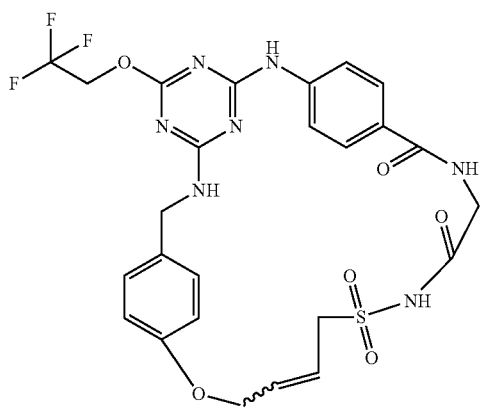

-continued
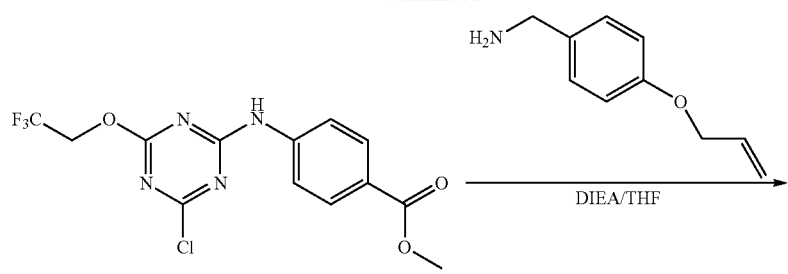
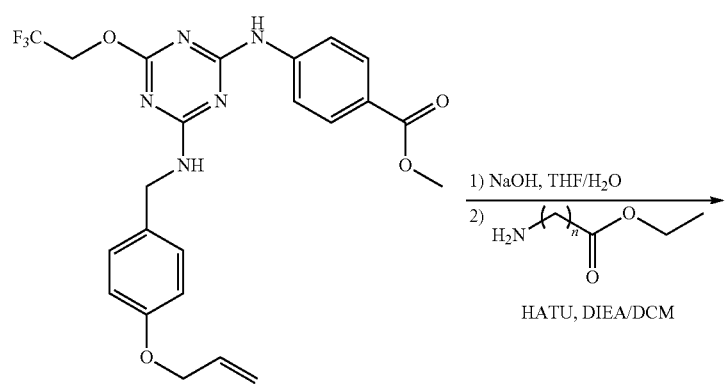
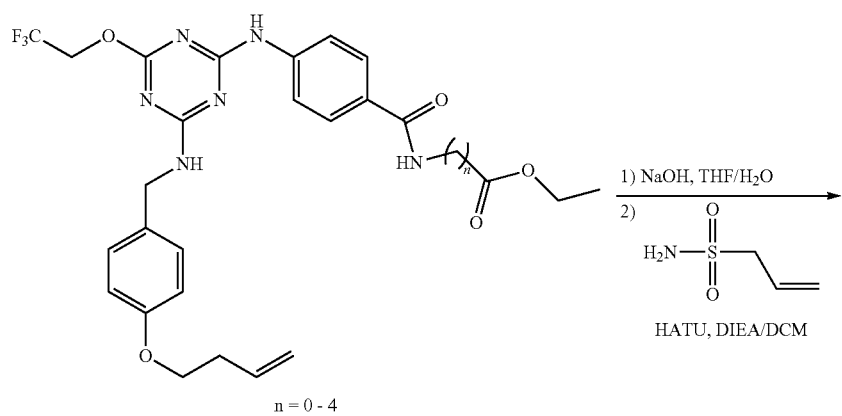
n = 0 - 4
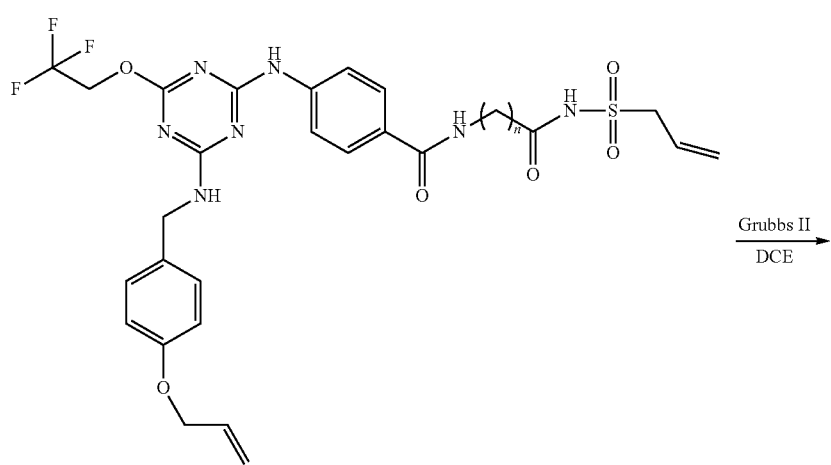

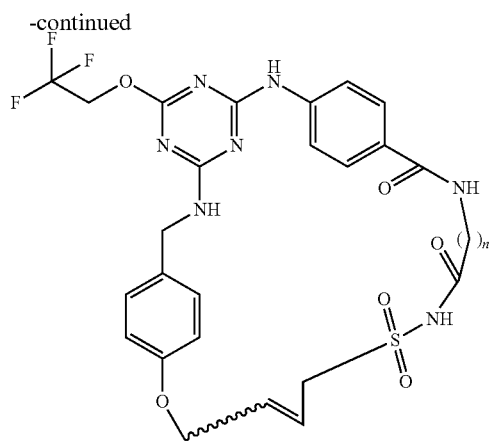

Example 4001 (n = 1)

Step 1: To a suspension of methyl 4-(4-chloro-6-(2,2,2-trifluoroethoxy)-1,3,5-triazin-2-ylamino)benzoate (500 mg, 1.38 mmol) in THF (5 mL) was added (4-(allyloxy)phenyl)methanamine (275 mg, 1.38 mmol) and iPr$_2$NEt (0.96 mL, 5.51 mmol). The mixture was stirred at room temperature for 16 hours. The solvent was removed under vacuum. The residue was purified via silica gel column (EtOAC/Hexanes=4:1) to give methyl 4-(4-(4-(allyloxy)benzylamino)-6-(2,2,2-trifluoroethoxy)-1,3,5-triazin-2-ylamino)benzoate (0.2 g, 30%) as a white solid.

| methyl 4-(4-(4-(allyloxy)benzylamino)-6-(2,2,2-trifluoroethoxy)-1,3,5-triazin-2-ylamino)benzoate | |
|---|---|
| MS (M + H)$^+$ Calcd. | 490.5 |
| MS (M + H)$^+$ Observ. | 490.1 |
| Retention Time | 1.09 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 2: To a suspension of methyl 4-(4-(2-(2-aminoethylamino)ethylamino)-6-(2,2,2-trifluoroethoxy)-1,3,5-triazin-2-ylamino)benzoate (200 mg, 0.41 mmol) in THF and water solution (6 mL, 1:1 ratio) was added NaOH (163 mg, 4.1 mmol). The mixture was heated to reflux for 16 hours. After cooling to room temperature, the reaction solution was acidified with 1N HCl. The product was extracted by EtOAc. The organic layer was washed with brine, dried over Na$_2$SO$_4$ and concentrated under vacuum. The crude product was used directly in the next step.

| 4-(4-(4-(allyloxy)benzylamino)-6-(2,2,2-trifluoroethoxy)-1,3,5-triazin-2-ylamino)benzoic acid | |
|---|---|
| MS (M + H)$^+$ Calcd. | 476.42 |
| MS (M + H)$^+$ Observ. | 475.99 |
| Retention Time | 2.21 min |

| 4-(4-(4-(allyloxy)benzylamino)-6-(2,2,2-trifluoroethoxy)-1,3,5-triazin-2-ylamino)benzoic acid | |
|---|---|
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 2 min |
| Flow Rate | 1 mL/min |
| Wavelength | 220 |
| Solvent Pair | MeOH:Water:TFA |
| Column | Phenomenex 2.0 × 30 mm, 3 uM |

Step 3: To a solution of 4-(4-(4-(allyloxy)benzylamino)-6-(2,2,2-trifluoroethoxy)-1,3,5-triazin-2-ylamino)benzoic acid (100 mg, 0.21 mmol) in DCM (3 mL) was added glycine ethyl ester HCl (44 mg, 0.32 mmol), HATU (120 mg, 0.32 mol) and iPr$_2$NEt (0.11 mL, 0.63 mmol). The mixture was stirred at r.t. for 16 hours before all the solvents were removed under vacuum. All solvents were removed under vacuum and the residue was purified by silica gel column (EtOAC/Hexanes=40% to 60%) to give ethyl 2-(4-(4-(4-(allyloxy)benzylamino)-6-(2,2,2-trifluoroethoxy)-1,3,5-triazin-2-ylamino)benzamido)acetate (100 mg, 81%) as a white solid.

| ethyl 2-(4-(4-(4-(allyloxy)benzylamino)-6-(2,2,2-trifluoroethoxy)-1,3,5-triazin-2-ylamino)benzamido)acetate | |
|---|---|
| MS (M + H)$^+$ Calcd. | 561.5 |
| MS (M + H)$^+$ Observ. | 561.0 |
| Retention Time | 1.02 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 4: To a suspension of ethyl 2-(4-(4-(4-(allyloxy)benzylamino)-6-(2,2,2-trifluoroethoxy)-1,3,5-triazin-2-ylamino)benzamido)acetate (100 mg, 0.18 mmol) in THF and water solution (6 mL, 1:1 ratio) was added NaOH (29 mg, 0.71 mmol). The mixture was heated to reflux for 2 hours. After cooling to room temperature, the reaction solution was acidified with 1N HCl. The product was extracted by EtOAc. The organic layer was washed with brine, dried over $Na_2SO_4$ and concentrated under vacuum. The crude product was used directly in the next step.

| 2-(4-(4-(4-(allyloxy)benzylamino)-6-(2,2,2-trifluoroethoxy)-1,3,5-triazin-2-ylamino)benzamido)acetic acid | |
|---|---|
| MS (M + H)+ Calcd. | 533.5 |
| MS (M + H)+ Observ. | 533.0 |
| Retention Time | 0.95 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 5: To a solution of 2-(4-(4-(4-(allyloxy)benzylamino)-6-(2,2,2-trifluoroethoxy)-1,3,5-triazin-2-ylamino)benzamido)acetic acid (50 mg, 0.09 mmol) in DMF (2 mL) was added prop-2-ene-1-sulfonamide (17 mg, 0.14 mmol), HATU (71 mg, 0.19 mol) and $iPr_2NEt$ (66 uL, 0.38 mmol). The mixture was stirred at r.t. for 16 hours before all the solvents were removed under vacuum. All solvents were removed under vacuum and the residue was purified by silica gel column (MeOH/DCM=5% to 10%) to give 4-(4-(4-(allyloxy)benzylamino)-6-(2,2,2-trifluoroethoxy)-1,3,5-triazin-2-ylamino)-N-(2-(allylsulfonamido)-2-oxoethyl)benzamide (53 mg, 89%) as a white solid.

| 4-(4-(4-(allyloxy)benzylamino)-6-(2,2,2-trifluoroethoxy)-1,3,5-triazin-2-ylamino)-N-(2-(allylsulfonamido)-2-oxoethyl)benzamide | |
|---|---|
| MS (M + H)+ Calcd. | 636.6 |
| MS (M + H)+ Observ. | 636.0 |
| Retention Time | 0.99 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 6: To a solution of 4-(4-(4-(allyloxy)benzylamino)-6-(2,2,2-trifluoroethoxy)-1,3,5-triazin-2-ylamino)-N-(2-(allylsulfonamido)-2-oxoethyl)benzamide (30 mg, 0.05 mmol) in dichloroethane (15 ml) in a sealed tube, nitrogen was bubbled in for ½ hr. Under nitrogen GrubbsII catalyst (18 mg, 9.5 umol) was added. The sealed tube was sealed and the reaction mixture was stirred at 90° C. for 16 hrs. The solvent was evaporated and the residue was purified by preparative HPLC to afford 3.7 mg (12%) white solid as desired product. $^1$H NMR (400 MHz, DMSO-D6) δ ppm 3.88 (m, 2H), 4.21 (m, 2H) 4.46 (m, 2H), 4.65 (m, 2H), 4.99 (m, 2H), 5.99-6.10 (m, 2H), 6.92 (d, J=8.78 Hz, 2H), 7.17-7.23 (m, 4H), 7.48 (d, J=8.53 Hz, 2H), 8.35 (s, broad, NH), 8.77 (s, broad, NH), 9.79 (s, broad, NH).

| Example 3007 | |
|---|---|
| MS (M + H)+ Calcd. | 608.6 |
| MS (M + H)+ Observ. | 608.1 |
| Retention Time | 2.51 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

Example 3008 and 3009

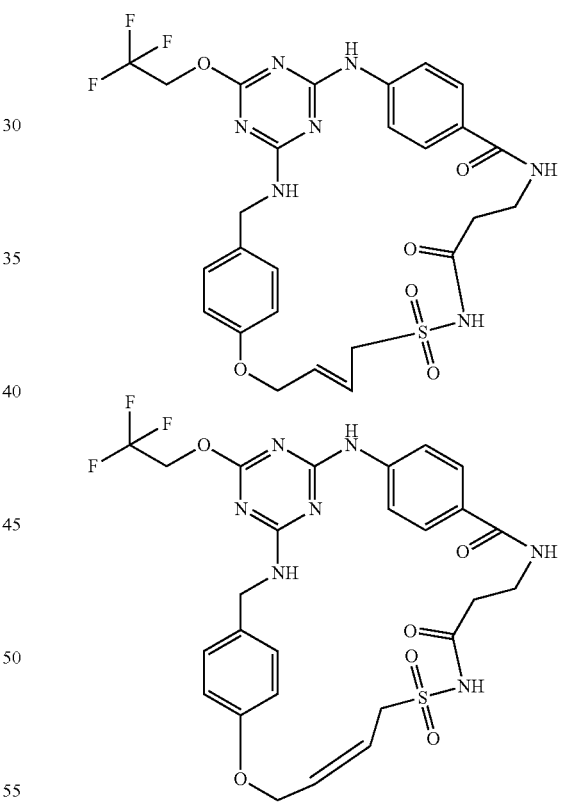

The Example 3008 and Example 3009 were synthesized following the procedure reported in Example 3007. ethyl 3-aminopropanoate HCl was used instead of glycine ethyl ester HCl in step 3.

Example 3008: $^1$H NMR (400 MHz, MeOD) δ ppm 2.63-2.71 (m, 2H), 3.72 (dd, J=6.02, 4.52 Hz, 2H), 4.13 (d, J=6.78 Hz, 2H), 4.54 (s, 2H), 4.61 (d, J=5.52 Hz, 2H), 4.90 (m, 2H), 5.84-5.92 (m, 1H) 5.99 (m, 1H), 6.90-6.94 (d, J=8.78 Hz, 2H), 7.24 (d, J=8.78 Hz, 2H), 7.40 (ddd, J=9.29, 2.51, 2.26 Hz, 2H), 7.55-7.63 (d, J=9.04 Hz, 2H).

Example 3009: $^1$H NMR (400 MHz, MeOD) δ ppm 2.68 (m, 2H), 3.71 (m, 2H), 4.42 (d, J=6.78 Hz, 2), 4.52 (s, 2H), 4.90 (m, 2H), 4.70 (d, J=5.52 Hz, 2H), 5.75 (m, 1H), 6.11 (m, 1H), 7.03 (d, J=8.78 Hz, 2H), 7.32 (d, J=8.53 Hz, 2H), 7.33-7.39 (m, 2H), 7.62 (d, J=9.03 Hz, 2H).

| Example 3008 | |
| --- | --- |
| MS (M + H)$^+$ Calcd. | 622.6 |
| MS (M + H)$^+$ Observ. | 622.2 |
| Retention Time | 2.56 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

| Example 3009 | |
| --- | --- |
| MS (M + H)$^+$ Calcd. | 622.6 |
| MS (M + H)$^+$ Observ. | 622.2 |
| Retention Time | 2.64 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

Example 3010

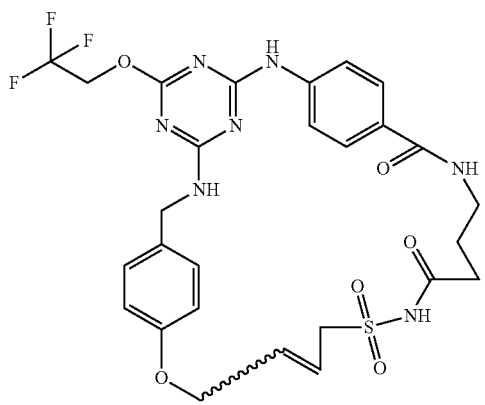 [SMILES: O=C1CCCNC(=O)c2ccc(cc2)Nc2nc(nc(OCC(F)(F)F)n2)NCc2ccc(cc2)OCC=CCS(=O)(=O)N1]

The Example 3010 was synthesized following the procedure reported in Example 3007. Ethyl 4-aminobutanoate HCl was used instead of glycine ethyl ester HCl in step 3. $^1$H NMR (400 MHz, MeOD) δ ppm 1.93 (m, 2H), 2.40 (m, 2H) 3.52 (m, 2H), 4.09 (d, J=6.78 Hz, 2H), 4.53 (s, 2H), 4.58 (d, J=5.52 Hz, 2H), 4.90 (m, 2H) 5.99 (m, 1H) 6.04 (m, 1H), 6.97 (d, J=9.03 Hz, 2H), 7.26 (d, J=8.78 Hz, 2H), 7.32 (d, J=8.78 Hz, 2H), 7.55 (d, J=8.78 Hz, 2H).

| Example 3010 | |
| --- | --- |
| MS (M + H)$^+$ Calcd. | 636.6 |
| MS (M + H)$^+$ Observ. | 636.2 |
| Retention Time | 2.55 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

Example 3011

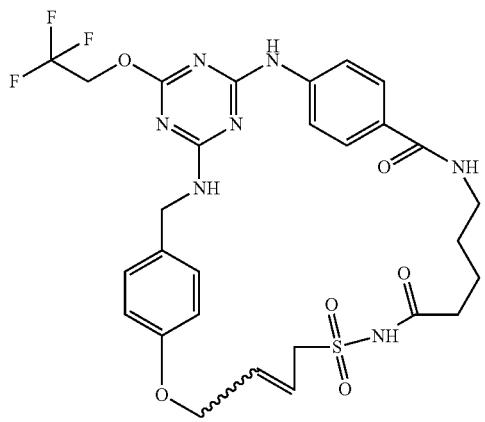 [SMILES: O=C1CCCCNC(=O)c2ccc(cc2)Nc2nc(nc(OCC(F)(F)F)n2)NCc2ccc(cc2)OCC=CCS(=O)(=O)N1]

The Example 3011 was synthesized following the procedure reported in Example 3007. Ethyl 5-aminopentanoate was used instead of glycine ethyl ester HCl in step 3.

$^1$H NMR (400 MHz, DMSO-D6) δ ppm 1.53 (m, 4H), 2.34 (m, 2H), 3.50 (m, 2H), 4.19 (m, 2H), 4.41 (d, J=6.27 Hz, 2H), 4.57 (m, 2H), 4.98 (m, 2H), 5.78 (m, 1H), 6.02 (m, 1H) 6.52 (s, broad, NH), 6.97 (d, J=8.53 Hz, 2H), 7.24 (d, J=8.78 Hz, 2H), 7.33 (d, J=8.53 Hz, 2H), 7.57 (d, J=8.78 Hz, 2H), 8.28 (s, broad, NH), 8.44 (s, broad, NH).

| Example 3011 | |
| --- | --- |
| MS (M + H)$^+$ Calcd. | 650.6 |
| MS (M + H)$^+$ Observ. | 650.2 |
| Retention Time | 2.61 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

Example 3012

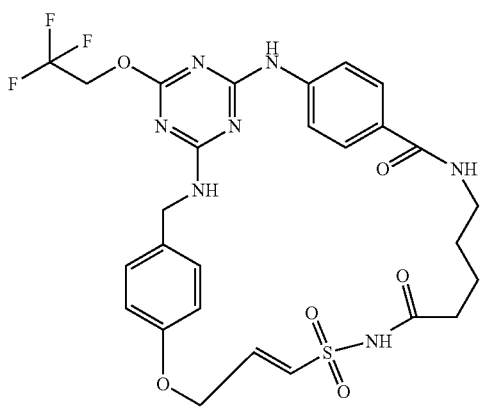 [SMILES: O=C1CCCCNC(=O)c2ccc(cc2)Nc2nc(nc(OCC(F)(F)F)n2)NCc2ccc(cc2)OC/C=C/S(=O)(=O)N1]

The Example 3012 was synthesized following the procedure reported in Example 3007. Ethyl 5-aminopentanoate and ethenesulfonamide were used instead of glycine ethyl ester HCl and prop-2-ene-1-sulfonamide in step 3 and step 5. $^1$H NMR (400 MHz, DMSO-D6) δ ppm 1.67 (m, 4H), 2.34 (m, 2H), 4.57 (s, 2H), 4.78 (m, 2H), 4.85 (m, 4H), 6.84 (m, 1H), 6.95 (m, 1H), 7.01 (d, J=8.53 Hz, 2H), 7.31 (d, J=8.78 Hz, 2H), 7.45 (d, J=8.53 Hz, 2H), 7.54 (d, J=8.78 Hz, 2H).

| Example 3012 | |
|---|---|
| MS (M + H)$^+$ Calcd. | 636.6 |
| MS (M + H)$^+$ Observ. | 636.2 |
| Retention Time | 2.58 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

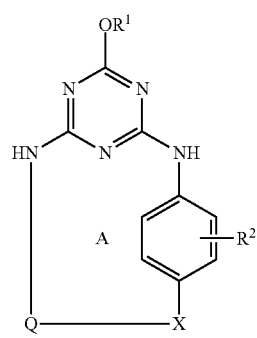

where
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
$R^2$ is hydrogen, cyano, halo, alkyl, haloalkyl, alkoxy, or haloalkoxy;
$R^3$ is hydrogen, alkyl, (amino)alkyl, (alkylamino)alkyl, (dialkylamino)alkyl, ((alkylcarbonyl)amino)alkyl, ((haloalkylcarbonyl)amino)alkyl, ((alkoxycarbonyl)amino) alkyl, ((benzyloxycarbonyl)amino)alkyl, alkylcarbonyl, alkoxycarbonyl, benzyloxycarbonyl, aminocarbonyl, alkylaminocarbonyl, or dialkyaminocarbonyl;
$R^4$ is hydrogen, alkyl, (amino)alkyl, (alkylamino)alkyl, or (dialkylamino)alkyl;
$R^5$ is hydrogen, alkyl, (amino)alkyl, (alkylamino)alkyl, or (dialkylamino)alkyl;
$R^6$ is pyrollidinyl, piperidinyl, or piperazinyl and is substituted with 0-3 substituents selected from alkyl, alkylcarbonyl, alkoxycarbonyl, and benzyloxycarbonyl;
Q is an alkylene or alkenylene chain containing 0-6 groups selected from the group consisting of 0, $NR^3$, S, S(O), S($O_2$), C(O)O, C(O)$NR^4$, OC(O)$NR^4$, $NR^4$C(O)$NR^4$, and Z, provided that any O or S atom does not directly bond to another O or S atom, such that ring A is 12-31 membered;
and where the alkylene or alkenylene chain is substituted with 0-6 substituents selected from the group consisting of alkyl, hydroxy, alkoxy, $R^6$, ($R^6$)alkyl, and phenyl where the phenyl substituent is further substituted with 0-4 substituents selected from cyano, halo, alkyl, haloalkyl, alkoxy, and haloalkoxy;
X is O, $CH_2$, CO, $CO_2$, or C(O)$NR^5$; and
Z is $C_{3-7}$ cycloalkylene, phenylene, pyrrolidindiyl, piperidindiyl, or piperazindiyl;
or a pharmaceutically acceptable salt thereof.
2. The compound of claim 1 where:
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
$R^2$ is cyano, hydrogen, halo, alkyl, haloalkyl, alkoxy, or haloalkoxy;
$R^3$ is hydrogen, alkyl, alkylcarbonyl, alkoxycarbonyl, aminocarbonyl, alkylaminocarbonyl, or dialkyaminocarbonyl;
$R^4$ is hydrogen or alkyl;

$R^5$ is hydrogen, alkyl, (amino)alkyl, (alkylamino)alkyl, or (dialkylamino)alkyl;

Q is an alkylene or alkenylene chain containing 0-3 groups selected from the group consisting of O, $NR^3$, S, S(O), $S(O_2)$, C(O)O, $C(O)NR^4$, $OC(O)NR^4$, $NR^4C(O)NR^4$, and Z, provided that O, $NR^3$, S, S(O), $S(O_2)$, C(O)O, $C(O)NR^4$, $OC(O)NR^4$, and $NR^4C(O)NR^4$ do not directly bond to each other or to NH or X, such that ring A is 13-24 membered; and where the alkylene or alkenylene chain is substituted with 0-3 substituents selected from the group consisting of alkyl, hydroxy, alkoxy, and phenyl where the phenyl substituent is further substituted with 0-4 cyano, halo, alkyl, haloalkyl, alkoxy, or haloalkoxy substituents;

X is O, $CO_2$, or $C(O)NR^5$; and

Z is $C_{3-7}$ cycloalkylene or phenylene;

or a pharmaceutically acceptable salt thereof.

3. The compound of claim 1 where $R^1$ is haloalkyl; $R^2$ is hydrogen; $R^3$ is hydrogen or alkylcarbonyl; $R^5$ is hydrogen; Q is an alkylene or alkeneylene chain containing 0-2 groups selected from the group consisting of O, $NR^3$, and Z, such that ring A is 16-31 membered; X is O or $CONR^5$; and Z is phenylene; or a pharmaceutically acceptable salt thereof.

4. The compound of claim 1 where $R^1$ is trifluoroethyl.

5. The compound of claim 1 where X is CONN.

6. The compound of claim 1 where X is O.

7. The compound of claim 1 where X is $C_{1-2}$.

8. The compound of claim 1 where Z is phenylene.

9. The compound of claim 1 where Z is cyclopropanediyl or cyclohexanediyl.

10. The compound of claim 1 where Z is pyrrolidindiyl or piperazindiyl.

11. The compound of claim 1 selected from the group consisting of

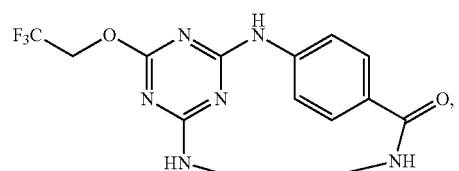

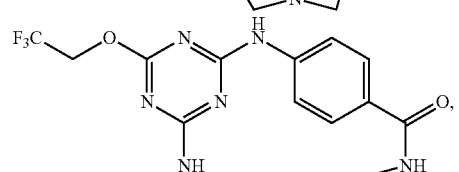

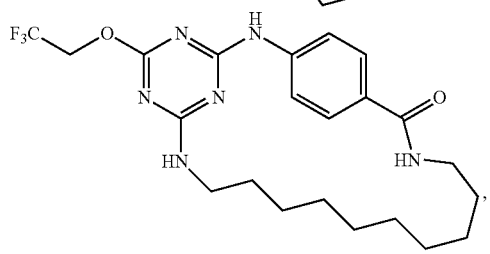

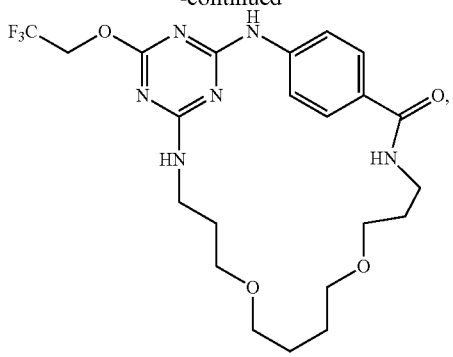

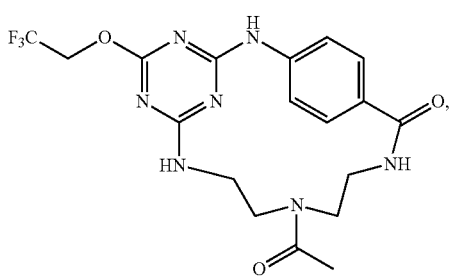

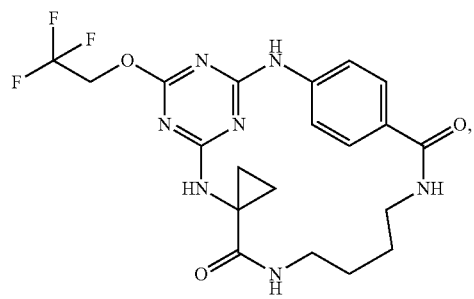

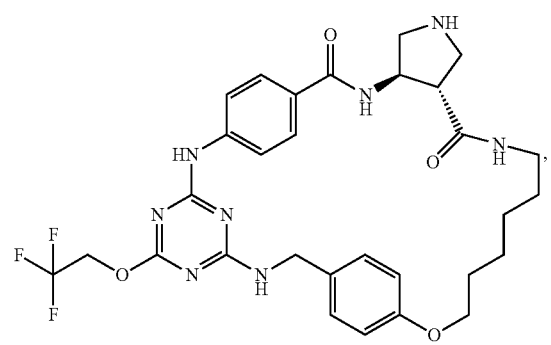

157
-continued
158
-continued
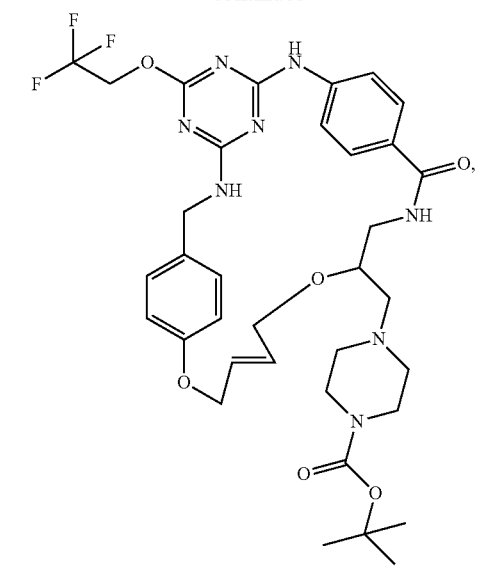
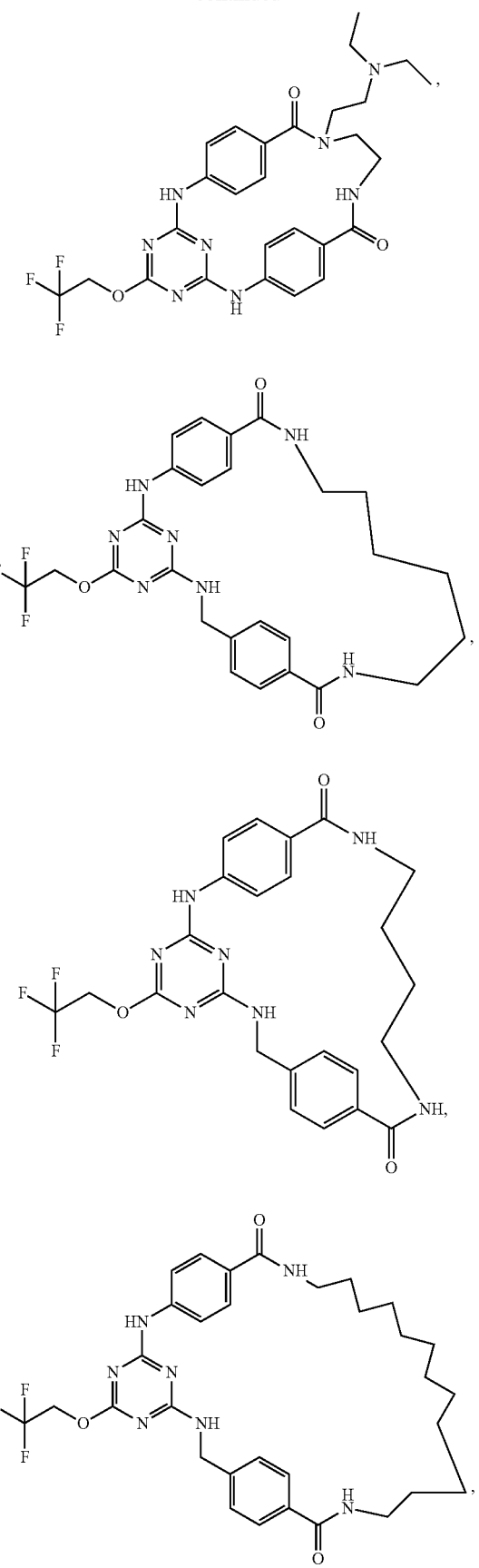

159
-continued
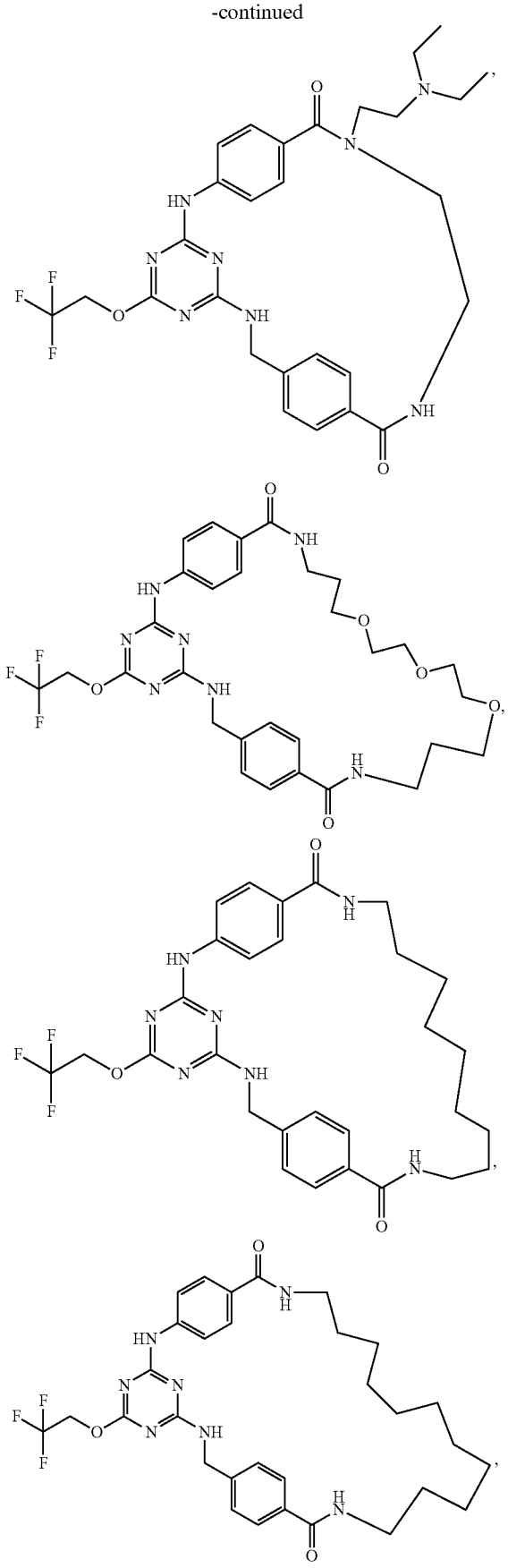
160
-continued
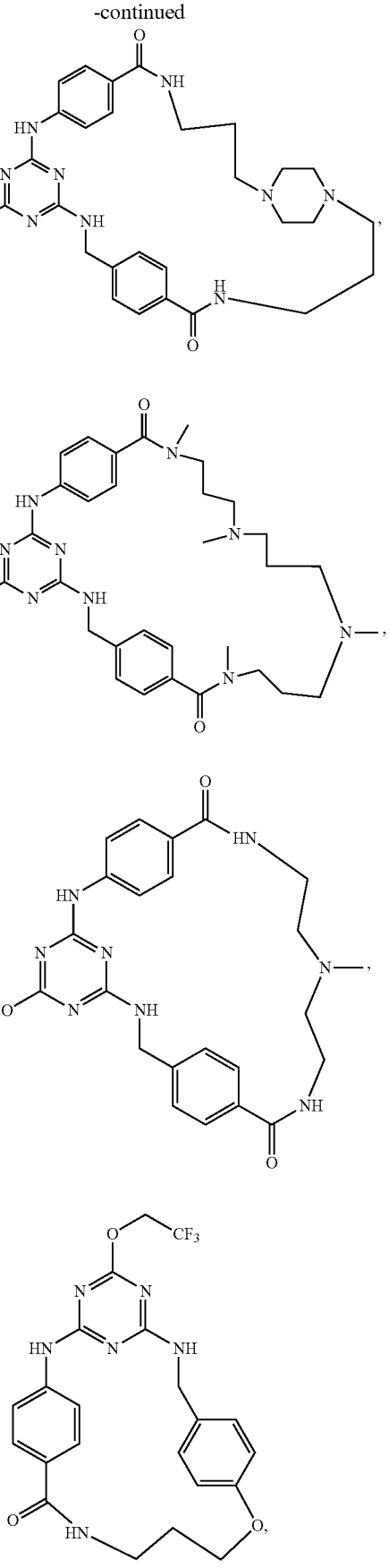

161
-continued
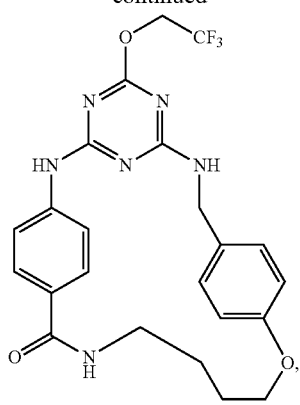
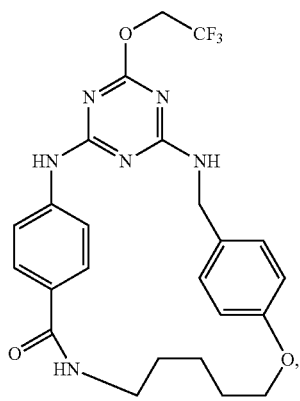
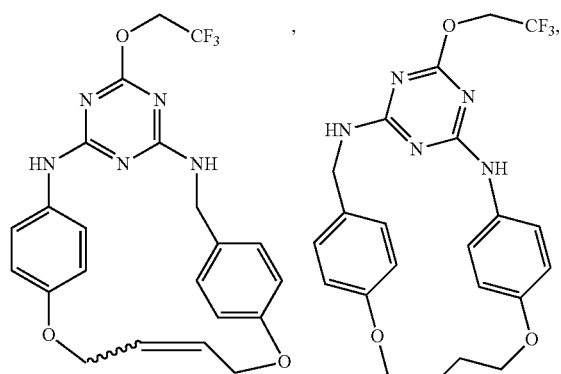
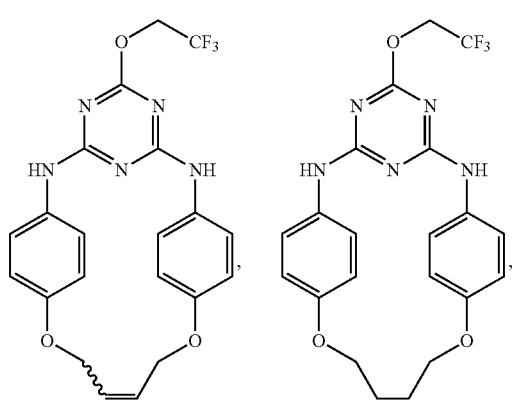
162
-continued
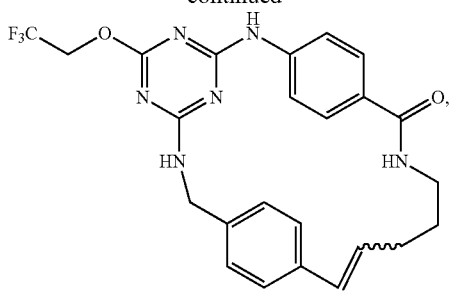
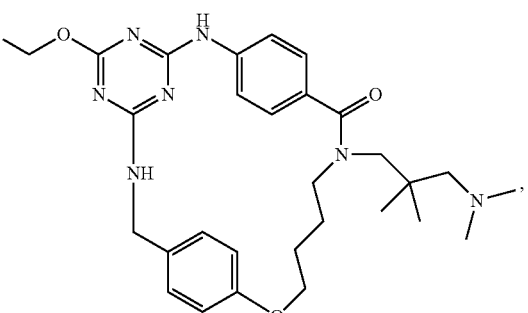
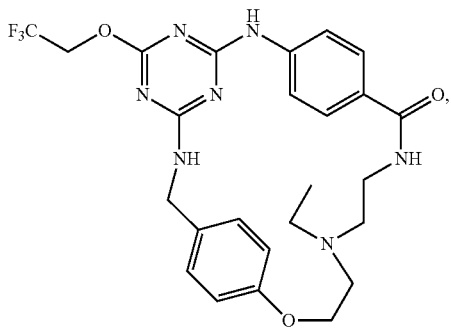
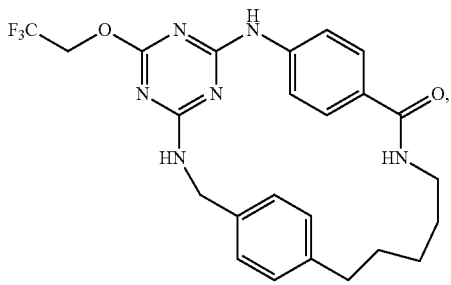
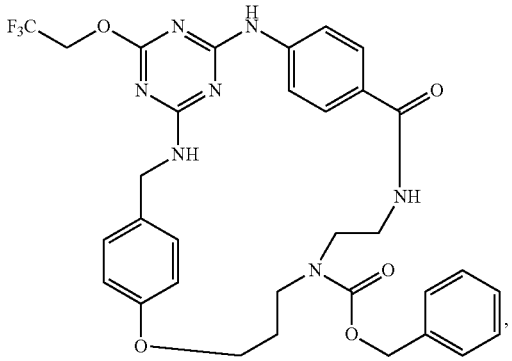

163
-continued
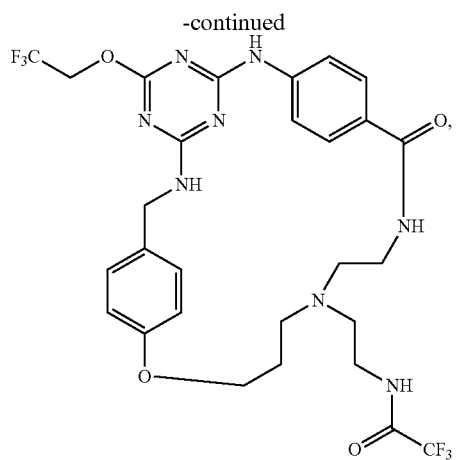
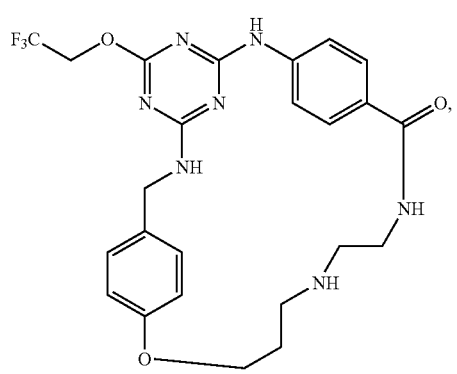
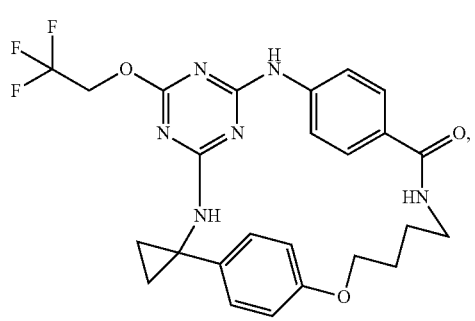
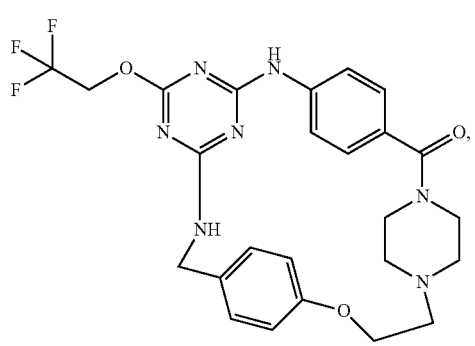
164
-continued
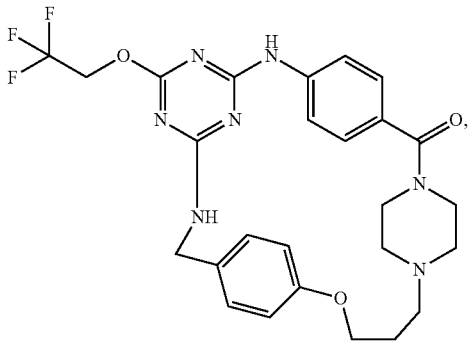
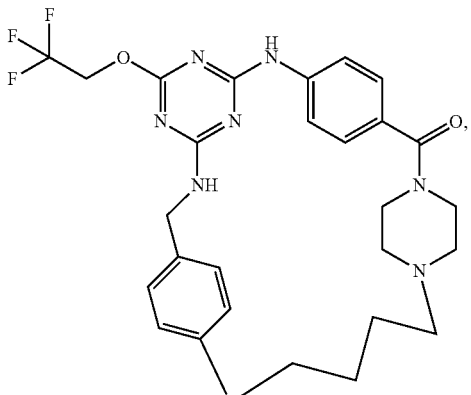
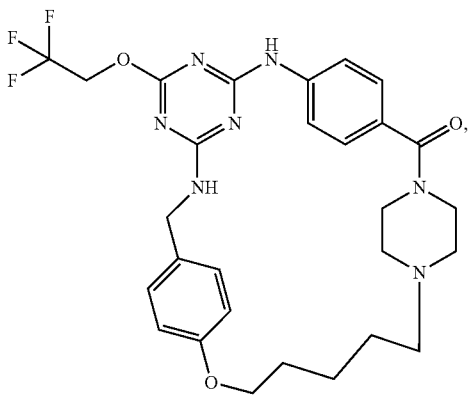
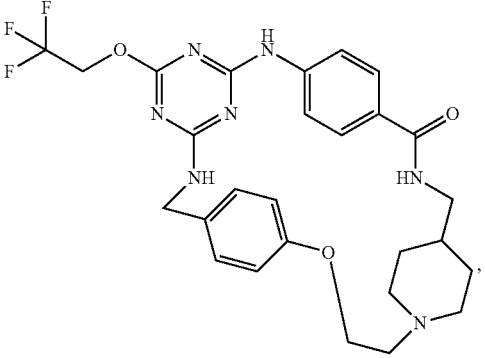

-continued

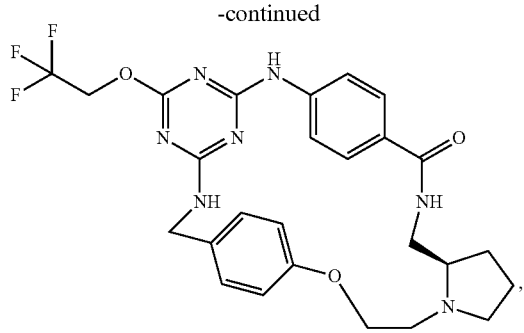

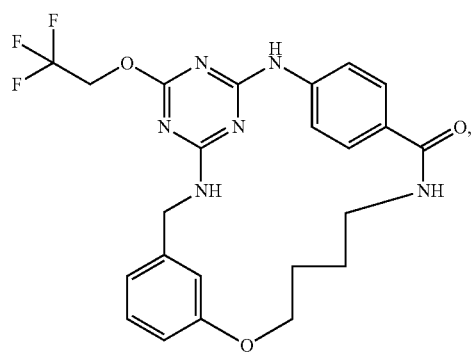

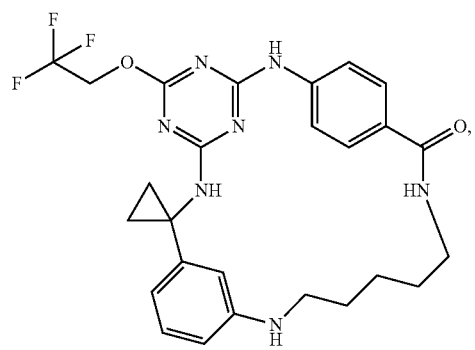

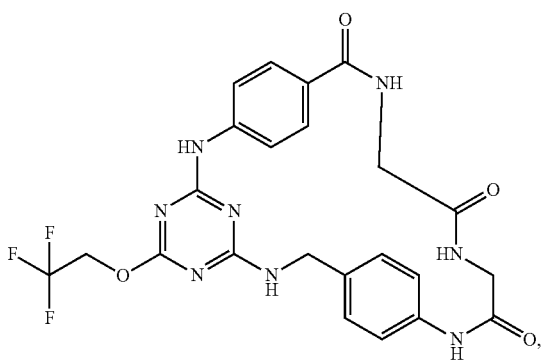

-continued

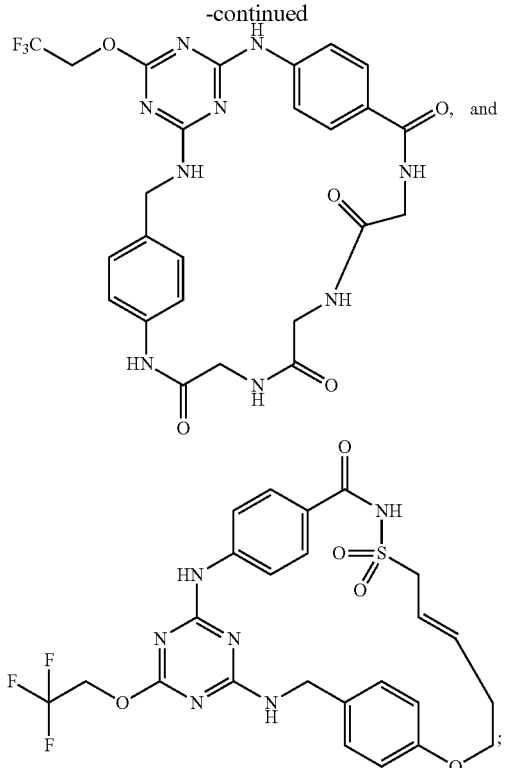

or a pharmaceutically acceptable salt thereof.

12. A composition comprising a compound of claim 1, or a pharmaceutically acceptable salt thereof, and a pharmaceutically acceptable carrier.

13. The composition of claim 12 further comprising at least one additional compound having therapeutic benefits for HCV wherein the compound is selected from the group consisting of interferons, cyclosporins, interleukins, HCV metalloprotease inhibitors, HCV serine protease inhibitors, HCV polymerase inhibitors, HCV helicase inhibitors, HCV NS4B protein inhibitors, HCV entry inhibitors, HCV assembly inhibitors, HCV egress inhibitors, HCV NS5A protein inhibitors, HCV NS5B protein inhibitors, and HCV replicon inhibitors.

14. A method of treating hepatitis C infection comprising administering a therapeutically effective amount of a compound of claim 1 to a patient in need thereof.

15. The method of claim 14 further comprising administering at least one additional compound having therapeutic benefits for HCV wherein the compound is selected from the group consisting of interferons, cyclosporins, interleukins, HCV metalloprotease inhibitors, HCV serine protease inhibitors, HCV polymerase inhibitors, HCV helicase inhibitors, HCV NS4B protein inhibitors, HCV entry inhibitors, HCV assembly inhibitors, HCV egress inhibitors, HCV NS5A protein inhibitors, HCV NS5B protein inhibitors, and HCV replicon inhibitors.

* * * * *

UNITED STATES PATENT AND TRADEMARK OFFICE
CERTIFICATE OF CORRECTION

PATENT NO. : 8,586,584 B2  
APPLICATION NO. : 12/904264  
DATED : November 19, 2013  
INVENTOR(S) : Tao Wang et al.

Page 1 of 1

It is certified that error appears in the above-identified patent and that said Letters Patent is hereby corrected as shown below:

In the Claims:

Claim 1:

Column 154, line 32, change "dialkyaminocarbonyl;" to -- dialkylaminocarbonyl; --.

Column 154, line 42, before "NR$^3$", change "0," to -- O, --.

Claim 2:

Column 154, lines 65 and 66, change "dialkyaminocarbonyl;" to -- dialkylaminocarbonyl; --.

Column 155, line 4, before "NR$^3$", change "0," to -- O, --.

Column 155, line 6, after "that", change "0," to -- O, --.

Claim 3:

Column 155, line 21, change "alkeneylene" to -- alkenylene --.

Column 155, line 22, before "NR$^3$", change "0," to -- O, --.

Claim 5:

Column 155, line 27, change "CONN." to -- CONH. --.

Claim 7:

Column 155, line 30, change "$C_{1-2}$." to -- $CH_2$. --.

Signed and Sealed this  
Third Day of June, 2014

Michelle K. Lee  
*Deputy Director of the United States Patent and Trademark Office*